(12) United States Patent
Straten et al.

(10) Patent No.: US 7,687,465 B2
(45) Date of Patent: Mar. 30, 2010

(54) THERAPEUTIC CANCER VACCINE

(75) Inventors: Per Thor Straten, Hvidovre (DK); Mads Hald Andersen, Hellerup (DK)

(73) Assignee: Kraeftens Bekaempelse (DK)

( * ) Notice: Subject to any disclaimer, the term of this patent is extended or adjusted under 35 U.S.C. 154(b) by 0 days.

(21) Appl. No.: 10/553,078

(22) PCT Filed: Apr. 7, 2004

(86) PCT No.: PCT/DK2004/000259
§ 371 (c)(1),
(2), (4) Date: Jun. 23, 2006

(87) PCT Pub. No.: WO2004/089980
PCT Pub. Date: Oct. 21, 2004

(65) Prior Publication Data
US 2007/0036811 A1  Feb. 15, 2007

Related U.S. Application Data

(60) Provisional application No. 60/461,803, filed on Apr. 11, 2003.

(30) Foreign Application Priority Data
Apr. 11, 2003  (DK) ............................... 2003 00572

(51) Int. Cl.
*A61K 38/00* (2006.01)
(52) U.S. Cl. ..................................................... 514/16
(58) Field of Classification Search ...................... None
See application file for complete search history.

(56) References Cited

U.S. PATENT DOCUMENTS 6,514,942 B1 * 2/2003 Ioannides et al. ............. 514/15

FOREIGN PATENT DOCUMENTS

| JP | 2002 284797 A | | 2/2003 |
|---|---|---|---|
| WO | WO 00/77201 A | | 12/2000 |
| WO | WO 00/03693 A | | 1/2001 |
| WO | WO 01/44282 A2 | | 6/2001 |
| WO | WO 02/033071 | | 4/2002 |
| WO | WO 02/072627 A2 | | 9/2002 |
| WO | WO03084467 | * | 10/2003 |

OTHER PUBLICATIONS

World Net online dictionary. Princeton University. Definition of peptide and polypeptide. 2006.*
Apostolopoulos, V., Osinski, C., and Mckenzie, I.F.C. Muc 1 cross-reactive Gal a(1,3)Gal antibodies in humans switch immune responses from cellular to humoral. Nature Medicine, 1998. vol. 4 No. 3, pp. 315-320.*
Jager, E., Gnjatic, S., Nagata, Y., Stockert, E., Jager, D., Karbach, J., Neumann, A., Rieckenberg, J., Chen, Y., Ritter, G., Hoffman, E., Arand, M., Old, L.J., and Knuth, A. Induction of primary NY-ESO-1 immunity: CD8+T lymphocyte and antibody responses in peptide-vaccinated patients with NY-ESO-1+cancers. PNAS, 2000. vol. 97, p. 12198-12203.*
Semino, Ferlazzo, Pietra, Pasquetti, Repetto, Rosso, Mariani, and Melioli. Heterogeneity of the alpha-interferon-mediated overexpression of class-I and class II major histocompatibility complex molecules in primary cultured cancer cells. Journal of Biological Regulators and Homeostatic Agents, 1993. vol. 7, pp. 99-105. Abstract only.*
Algarra, I., Collado, A., and Garrido, F. Altered MHC class I antigens in tumors. International Journal of Clinical and Laboratory Research, 1997. vol. 27, pp. 95-102. Abstract only.*
Bodey, B., Bodey, B., Siegel, S.E., and Kaiser, H.E. Failure of cancer vaccines: the significant limitations of this approach to immunotherapy. Anticancer Research, 2000. vol. 20, pp. 2665-2676. Abstract only.*
Ohlen, C., Kalos, M., Hong, D.J., Shur, A.C., and Greenberg, P.D. Expression of a tolerizing tumor antigen in peripheral tissue does not preclude recovery of high-affinity CD8+T cells or CTL Immunotherapy of tumors expressing the antigen. Journal of Immunology, 2001. vol. 166, pp. 2863-2870.*
Antonia, S.J., Geiger, T., Miller, J., and Flavell, R.A. Mechanisms of immune tolerance induction through the thymic expression of a peripheral tissue-specific protein. International Immunology, 1995. vol. 7, pp. 715-725.*
Yu, Z., and.Restifo, N.P. Cancer vaccines: progress reveals new complexities. Journal of Clinical Investigation, 2002. vol. 110, pp. 289-294.*
Roitt, I., Delves, P.J., and Rabson, A., eds. "Lymphocyte Activiation" in Really Essential Medical Immunology. Blackwell Publishing, 2004. pp. 75-79.*
Hoffmann, P., Hofmeister, R., Brischwein, K., Brandl, C., Crommer, S., Bargou, R., Itin, C., Prang, N., and Baeuerle, P.A. Serial killing of tumor cells by cytotoxic T cells redirected with a CD19/CD3 bispecific single-chain antibody construct. International Journal of Cancer, 2005. vol. 115, pp. 98-104.*
Burgess, Shaheen, Ravera, Jaye, Donohue, and Winkles. Possible dissociation of the heparin-binding and mitogenic activities of heparin-binding (acidic fibroblast) growth factor-1 from its receptor-binding activities by site-directed mutagenesis of a single lysine residue. Journal of Cell Biology, 1990. vol. 111, pp. 2129-2138.*
Lazar, E., Watanabe, S., Dalton, S. and Sporn, M.B. Transforming growth factor a: mutation of aspartic acid 47 and leucine 48 results in different biological activities. Molecular and Cellular Biology, 1988. vol. 8 No. 3, pp. 1247-1252.*
Schwartz, G.P., Burke, G.T., and Katsoyannis, P.G. A superactive insulin: [B10-aspartic acid] insulin (human). Proceedings of the National Academy of Sciences, 1987. Vol. 84, pp. 6408-6411.*

(Continued)

*Primary Examiner*—Christopher H Yaen
(74) *Attorney, Agent, or Firm*—Davis Wright Tremaine LLP

(57) ABSTRACT

The present invention relates to polypeptides capable of raising a specific T-cell response, wherein the polypeptide comprises a peptide consisting of at least 9 consecutive amino acid residues of ML-IAP, as well as to the use of such polypeptides as medicaments. The invention furthermore relates to use of such polypeptides for treatment of a clinical condition, such as cancer. The invention also relates to methods of selecting a peptide comprising a peptide fragment of ML-IAP for use in a vaccine compositions as well as to vaccine compositions comprising isolated ML-IAP (SEQ ID NO:1) and/or one or more polypeptide fragments thereof.

9 Claims, 5 Drawing Sheets

OTHER PUBLICATIONS

Lin, M.C., Wright, D.W., Hruby, V.J., and Rodbell, M. Structure-function relationships in glucagon: properties of highly purified Des-His1-, Monoiodo-, and [Des-Asn28, Thr29] (homoserine lactone 27)-glucagon. Biochemistry, 1975. vol. 14 No. 8, pp. 1559-1563.*

Skolnick, J. And Fetrow, J.S. From genes to protein structure and function: novel applications of computational approaches in the genomic era. Trends in Biotechnology, 2000. vol. 18, pp. 34-39.*

Andersen et al., "Identification of a Cytotoxic T Lymphocyte Response to the Apoptose Inhibitor Polypeptide Survivin in Cancer Patients," *Cancer Res.* 61, 869-872 (2001).

Anderson et al., "Spontaneous cytotoxic T-cell responses against survivin-derived MHC class l-restricted T-cell epitopes in situ as well as ex vivo in cancer patients," *Cancer Research*, American Association for Cancer Research, Baltimore, MD, USA, vol. 61, No. 16 (Aug. 15, 2001).

Anderson et al., "The melanoma inhibitor of apoptosis protein: A target for spontaneous cytotoxic T cell responses" *Journal of Investigative Dermatology*, vol. 122, No. 2, (Feb. 2004).

Ashhab et al., "Two splicing variants of a new inhibitor of apoptosis gene with different biological properties and tissue distribution pattern" *FEBS Lett.* 20, 56-60 (2001).

Battegay et al., "Impairment and delay of neutralizing antiviral antibody responses by virus-specific cytotoxic T cells," J. Immunol. 15, 5408-15 (1993).

Becker et al., "Lesion-specific activation of cloned human tumor-infiltrating lymphocytes by autologous tumor cells: induction of proliferation and cytokine production," *J. Invest. Dermatol.* 101, 15-21 (1993).

Cormier et al., "Comparative analysis of the in vivo expression of tyrosinase, Mart-1/Melan-A, and gp100 in metastatic melanoma lesions: implications for immunotherapy," *J. Immunother.* 21, 27-31 (1998).

Ennis et al., "Antibody and cytotoxic T lymphocyte responses of humans to live and inactivated influenza vaccines" *J. Gen. Virol.* 58, 5408-15 (1982).

Herr et al., "Identification of naturally processed and HLA-presented Epstein-Barr virus peptides recognized by CD4(+) or CD8(+) T lymphocytes from human blood," *Proc. Natl. Acad, Sci. U.S.A.* 96, 12033-12038 (1999).

Heslop et al., "Adoptive cellular immunotherapy for EBV lymphoproliferative disease," *Immunol. Rev.*, 157, 217-222 (1997).

Jaattela, M., "Escaping cell death: survival polypeptides in cancer," *Exp. Cell Res.* 248, 30-43 (1999).

Jager et al., "Immunoselection in vivo: independent loss of MHC class I and melanocyte differentiation antigen expression in metastatic melanoma" *Int. J. Cancer* 71, 142-147 (1997).

Anderson, Mads Hald et al., *Cancer Research*, 61:869-872: Feb. 1, 2000. "Identification of a cytotoxic T lymphocyte response to the apoptosis inhibitor protein survivin in cancer patients.".

Wobser, M. et al., *Cancer Immunol Immunother.*, 55(10):1294-8, Nov. 2005, "Complete remission of liver metastasis of pancreatic cancer under vaccination with a HLA-A2 restricted peptide derived from the universal tumor antigen survivin.".

Otto, K. et al., *Vaccine*, 23(7):884-9, Jan. 4, 2005. Lack of toxicity of therapy-induced T cell responses against the universal tumour antigen survivin.

Kasof et al.. "Livin. A novel inhibitor of apoptosis polypeptide family member," *J. Biol. Chem.* 276, 3238-3246 (2001).

Kessler et al., "Competition-based cellular peptide binding assays for 13 prevalent HLA class I alleles using fluorescein-labeled synthetic peptides," Hum. Immunol. 64, 245-255 (2003).

Kubo et al., "Definition of specific peptide motifs for four major HLA-A alleles," J. lmmunol. 152, 3913-3924 (1994).

Marchand et al., "Tumor regressions observed in patients with metastic melanoma treated with an antigenic peptide encoded by gene MAGE-3 and presented by HLA-A1 " *Int. J. Cancer* 80, 219-230 (1999).

Moudgil et al., "Can antitumor immune responses discriminate between self and nonself?" *Immunol. Today* 15, 353-355 (1994).

Nestle et al., "Vaccination of melanoma patients with peptide- or tumor lysate-pulsed dendritic cells," *Nat. Med.* 4, 328-332 (1998).

Parkhurst et al., "Improved induction of melanoma-reactive CTL with peptides from the melanoma antigen gp 100 modified at HLA-A*0201-binding residues" *J. Immunol.* 157, 2539-2548. (1996).

Rosenberg et al., "Immunological and therapeutic evaluation of a synthetic peptide vaccine for the treatment of patients with metastatic melanoma," *Nat. Med.* 4, 321-327 (1998).

Rosenberg, S.A., "Development of cancer immunotherapies based on identification of the genes encoding cancer regression antigens," *J. Natl. Cancer Inst.* 20, 1635-1644 (1996).

Scheibenbogen et al., "Identification of known and novel immunogenic T-cell epitopes from tumor antigens recognized by peripheral blood T cells from patients responding to IL-2-based treatment," *Int. J. Cancer* 20, 409-414 (2002).

Schmollinger et al. "Melanoma inhibitor of apoptosis protein (ML-IAP) is a target for immune- mediated tumor destruction," *Proceedings of the National Academy of Sciences of the U.S.A.*, vol. 100, No. 6 (Mar. 18, 2003).

Thurner et al., "Vaccination with mage-3A1 peptide-pulsed mature, monocyte-derived dendritic cells expands specific cytotoxic T cells and induces regression of some metastases in advanced stage IV melanoma," *J. Exp. Med.* 190, 1669-1678 (1999).

Van Den Eynde et al., "Tumor recognized by T lymphocytes," *Int. J. Clin. Lab. Res.* 27, 81-86 (1997).

Vucic et al., "ML-IAP, a novel inhibitor of apoptosis that is preferentially expressed in human melanomas," *Curr. Biol.* 10 1359-1366 (2000).

Yee et al., "Melanocyte destruction after antigen-specific immunotherapy of melanoma: direct evidence of t cell-mediated vitiligo" *J. Exp. Med.* 192, 1637-1644 (2000).

Yewdell et al., "Immunodominance in major histocompatibility complex class I-restricted T lymphocyte responses," *Annu. Rev. Immunol.* 17, 51-88 (1999).

Zeh et al., "High avidity CTLs for two self-antigens demonstrate superior in vitro and in vivo antitumor efficacy" J. Immunol., 162, 989-94 (1999).

* cited by examiner

No peptide     ML-IAP$_{280}$

No peptide     ML-IAP$_{280}$

No peptide     ML-IAP$_{280}$

No peptide     ML-IAP$_{280}$

THERAPEUTIC CANCER VACCINE

RELATED APPLICATIONS

The present application is a U.S. national phase application under 35 U.S.C. §371, based on PCT/DK2004/000259, filed Apr. 7, 2004, which claims priority to both PA200300572, filed Apr. 11, 2003 and U.S. Application No. 60/461,803, filed Apr. 11, 2003, the entireties of all of which are incorporated herein by reference.

All patent and non-patent references cited in this patent application are hereby incorporated by reference in their entirety.

FIELD OF THE INVENTION

The present invention relates to fragments of ML-IAP (livin) and a therapeutic vaccine comprising one or more ML-IAP polypeptide fragments. The vaccine can be used for prophylactic, ameliorating and/or curative treatment of e.g. cancers and auto-immune diseases.

BACKGROUND OF THE INVENTION

It is well established that peptide epitopes derived from human tumor-associated antigens (TAA) can be recognized by cytotoxic T lymphocytes (CTL) in the context of MHC molecules[1] and that most—if not all—tumors express such antigens. Consequently, exciting clinical efforts are ongoing to target these TAA in strategies such as vaccination and adoptive T cell therapy in order to generate effective anti-tumor CTL responses in patients[2-5].

For melanoma, the tumor for which the largest number of CTL defined TAA have been characterized, powerful CTL responses against antigens have been induced by vaccination and some patients have experienced a complete remission of their disease[6-7].

However, immunoselection of antigen loss variants can be a serious obstacle for the curative potential of most of the known CTL epitopes in clinical oncology, and the selection of antigen deficient mutant tumors is a well-recognized limitation in therapeutic strategies when targeting antigens that do not have a role in cancer growth[5,27,28]. The reason is that most characterized peptides are derived from polypeptides, which are not essential for the survival of the tumor cell. Thus, if powerful CTL responses are induced against these peptide antigens by therapeutical measures such as vaccinations, tumor cells lacking the expression of the targeted antigen are very likely to escape the raised immune responses[8,9].

There is a need for more efficient therapeutical vaccines and improved methods of treatment of cancer and autoimmune diseases.

SUMMARY OF THE INVENTION

The therapeutical application of tumor antigens the expression of which is essential for the survival of tumor cells represents a strategy for cancer treatment by preventing antigen loss variants from emerging due to immunoselection, particularly during immune therapy. However, the identification of specific fragments, which comprise good antigenic properties is difficult.

The inhibitor of apoptosis protein (IAP) family[12] represents one example of tumor antigens the expression of which is essential for the survival of tumor cells. Inhibition of apoptosis both enhances the survival of cancer cells and prevents the cancer cells from escaping from immune surveillance and cytotoxic therapies.

A number of different IAPs have been described. Their different expression patterns suggest an organ-specific role in promoting cell survival during development and tissue homeostasis. While X-IAP, C-IAP1 and C-IAP2 are relatively ubiquitously expressed, survivin is expressed only in fetal and tumor tissues.

The inhibitor of apoptosis polypeptide ML-IAP has a rather selective expression pattern, as it is predominantly detected in melanomas and a few other tissues[13,14]. The only other IAP with well-documented expression in melanoma is survivin.

ML-IAP can be detected in the majority of melanoma cell lines tested but not in normal melanocytes[14]. Melanoma cell lines with high levels of ML-IAP are more resistant to drug-induced apoptosis than are normal primary melanocytes. Thus, ML-IAP might be a critical cellular factor and increased expression levels of ML-IAP confer resistance to apoptotic stimuli, thereby contributing to the pathogenesis and progression of malignant melanomas.

The polypeptide ML-IAP inhibits apoptosis and cell death induced by death receptors and chemotherapeutic agents can thus be expected to be hampered by expression of ML-IAP.

Accordingly, elevated expression of ML-IAP renders melanoma cells resistant to apoptotic stimuli and thereby potentially contributes to the pathogenesis of this malignancy.

The present invention demonstrates that T-cells infiltrating the tumor environment or circulating in the peripheral blood of melanoma patients specifically recognize ML-IAP derived peptides. Thus, ML-IAP is on the one hand important for the survival of the cancer cell and on the other hand a target for immunological effector cells.

The present invention is in one aspect directed to fragments of ML-IAP (SEQ ID NO:1) capable of eliciting a specific T-cell response.

In another preferred aspect the present invention is directed to a therapeutic vaccine comprising ML-IAP (SEQ ID NO:1), and/or one or more fragments of ML-IAP (SEQ ID NO:1) capable of eliciting a specific T-cell response, including a response involving the activation of cytotoxic T-cells and/or T helper (Th) cells. The vaccine composition preferably further comprises an adjuvant and/or a carrier.

In yet another aspect there is provided a pharmaceutical composition comprising ML-IAP (SEQ ID NO:1), and/or one or more fragments of ML-IAP (SEQ ID NO:1) capable of eliciting a specific T-cell response, including a response involving the activation of cytotoxic T-cells and/or T helper (Th) cells, and a bioactive compound selected from the group consisting of a chemotherapeutic agent, an immunotherapeutic agent, and a second cancer vaccine composition. The pharmaceutical composition can further comprise an adjuvant and/or a carrier.

In a still further aspect of the invention there is provided a kit-of-parts comprising ML-IAP (SEQ ID NO:1), and/or one or more fragments of ML-IAP (SEQ ID NO:1) capable of eliciting a specific T-cell response, including a response involving the activation of cytotoxic T-cells and/or T helper (Th) cells, and a bioactive compound selected from the group consisting of a chemotherapeutic agent, an immunotherapeutic agent, and a second cancer vaccine composition, wherein the one or more fragments of ML-IAP (SEQ ID NO:1) capable of eliciting a specific T-cell response and the bioactive compound selected from the group consisting of a chemotherapeutic agent, an immunotherapeutic agent, and a cancer vaccine can be administered simultaneously, or sequentially in any order. The kit-of-parts can optionally comprise a manual comprising information on the dosage regime or the administration of the ML-IAP fragment and the bioactive compound.

In yet another aspect of the invention there is provided a method for treatment of a human or animal body, wherein said method comprises the step of administering to an individual in need of said treatment the pharmaceutical composition or the components of the kit-of-parts according to the invention.

In a still further aspect of the invention there is provided the use of a fragment of ML-IAP in the manufacture of a vaccine composition capable of raising a specific T-cell response in an individual to which the vaccine composition has been administered.

In yet another aspect of the invention there is provided the use of a fragment of ML-IAP in combination with a bioactive agent in the manufacture of a pharmaceutical composition for treatment of a cancer and/or an auto-immune disease in an individual in need of said treatment.

In a still further aspect of the invention there is provided a method for activating and expanding T-cells specific for ML-IAP or fragments thereof, said method comprising the steps of co-cultivating T-cells and ML-IAP, and/or at least one fragment thereof, thereby activating the T-cells, and isolating activated ML-IAP specific T-cells and/or ML-IAP fragment specific T-cells.

In yet another aspect of the invention there is provided a method for treating an individual diagnosed with a cancer, or at risk of developing a cancer, said method comprising the steps of administering to said individual at least one isolated and activated ML-IAP specific T-cell, and/or at least one isolated and activated ML-IAP fragment specific T-cell.

Figure 1A:
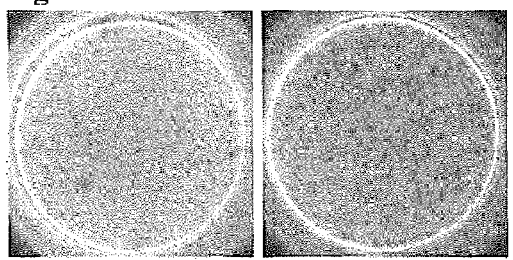
FIG. 1
Figure 1B:
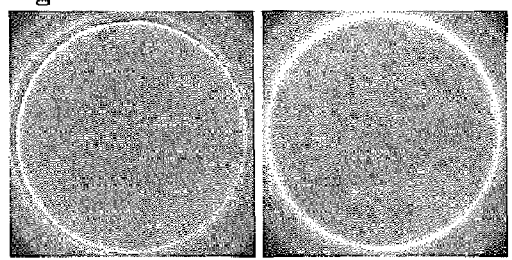
Figure 1C:
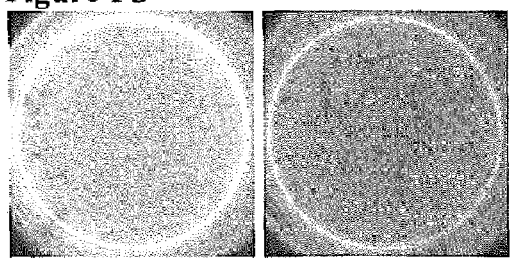
Figure 1D:
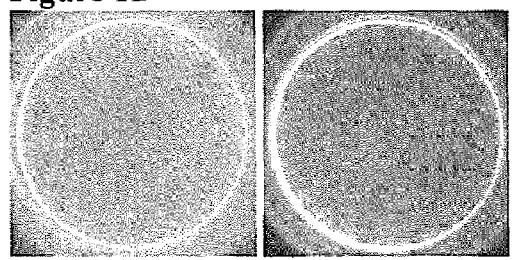
Figure 1E:
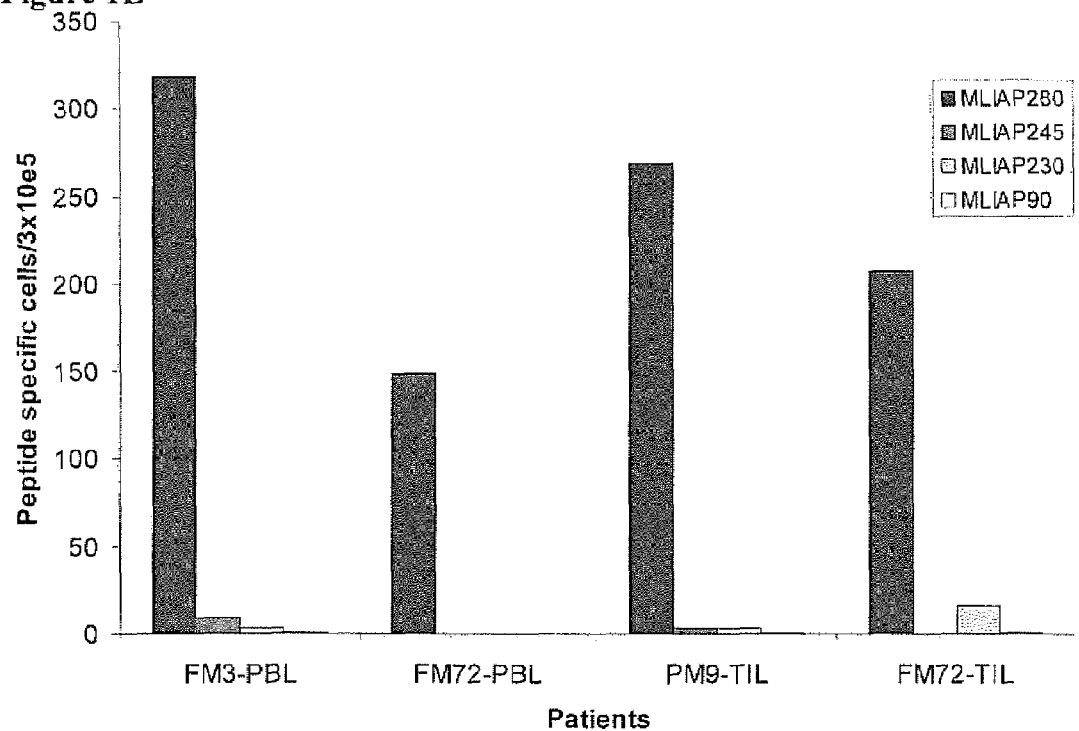

T-cell response against the ML-IAP$_{280}$ (QLCPICRAPV) peptide as measured in an ELISPOT in PBL from the melanoma patient FM3 (FIG. 1A) or FM72 (FIG. 1B) and in TIL from the melanoma patient PM9 (FIG. 1C) or FM72 (FIG. 1D). T-lymphocytes were stimulated once with peptide before plated at 3×10$^5$ cells per well in duplicates either without or with peptide. The average number of peptide specific spots (after subtraction of spots without added peptide) was calculated for each patient using a CCD scanning device and a computer system (FIG. 1E).

FIG. 2

T-cell response as measured in ELISPOT against the peptides ML-IAP$_{280}$ (QLCPICRAPV), ML-IAP$_{245}$ (RLQEERTCKV), ML-IAP$_{230}$ (VLEPPGARDV), and ML-IAP$_{90}$ (RLASFYDWPL) in TIL samples from nine patients and in PBL from two patients. T-lymphocytes were stimulated once with peptide before plated at 3×10$^5$ cells per well in duplicates either without or with peptide. The average number of peptide specific spots (after subtraction of spots without added peptide) was calculated for each patient using a CCD scanning device and a computer system.

FIG. 3

T-cell response against the ML-IAP$_{245-253}$ (RLQEERTCK) peptide as measured in an ELISPOT in PBL from 14 melanoma patients. T-lymphocytes were stimulated once with peptide before plated in triplicates either without or with peptide. The average number of peptide specific cells (after subtraction of spots without added peptide) was calculated for each patient as the number of spot forming cells per 10$^5$ CD8 positive cells after subtraction of the number of background spots formed without addition of peptide using the ImmunoSpot® Series 2.0 Analyzer (CTL Analyzers, LLC, Cleveland, US).

FIG. 4

In situ detection of ML-IAP-reactive CTL. Confocal laser scanning microscopy was used to detect CTL reacting with a Cy3-conjugated anti-CD8 antibody (red channel) and a fluorescein isothiocyanate-conjugated multimeric HLA-A2/ML-IAP$_{280}$ construct (green channel) (first and second columns) or with a fluorescein isothiocyanate conjugated multimeric HLA-A2/ML-IAP$_{245}$ construct (last column) in primary tumors from two HLA-A2-positive melanoma patients.

FIG. 5

Figure 5A:
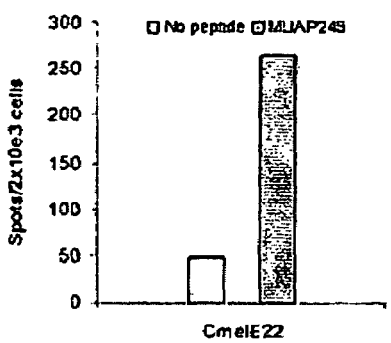
Figure 5B:
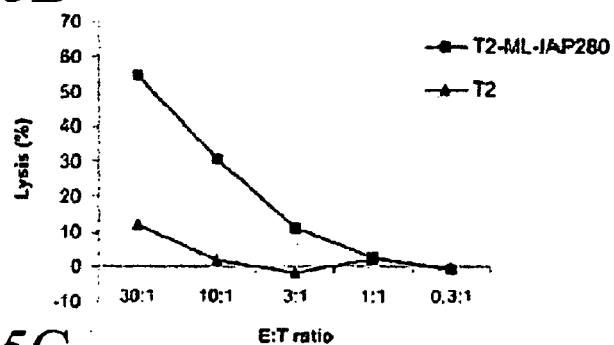
Figure 5C:
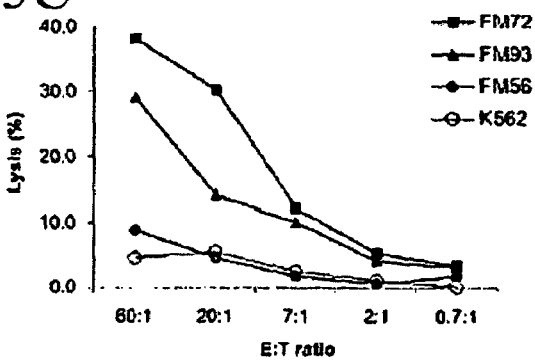

Cytolytic capacity of ML-IAP-specific CTL. ML-IAP$_{245}$-reactive CTL were isolated from PBL from the melanoma patients CmelE22 using peptide-coated magnetic beads before being plated at 2×10$^3$ cells per well in duplicates either with T2 cells without or pulsed with ML-IAP$_{245}$ (RLQEERTCKV) (FIG. 5A). ML-IAP$_{280}$-reactive CTL were isolated from a melanoma-infiltrated lymph node from patient Cmel72 using peptide-coated magnetic beads. These cells were analyzed for specific lysis of T2 cells with (square) or without (triangle) ML-IAP$_{280}$ peptide (QLCPICRAPV) (FIG. 5B). Lysis by ML-IAP$_{280}$-isolated T cells of the autologous melanoma cell line FM93 (triangle), the HLA-A2 negative cell line FM56 (black circle) and the natural killer target cell line K562 (white circle) (FIG. 5C).

DETAILED DESCRIPTION OF THE INVENTION

Preferred embodiments of the present invention is disclosed herein below.

Fragments of Ml-IAP and Therapeutical Vaccine Compositions Comprising Such Fragments or Full-Length ML-IAP In preferred embodiments the present invention is directed to fragments of ML-IAP and therapeutical vaccine compositions comprising one or more fragments of ML-IAP, and a pharmaceutically acceptable carrier. The vaccine composition can further comprise a carrier and/or an adjuvant compound. A vaccine composition comprising full-length ML-IAP (SEQ ID NO:1) is also provided.

Preferred fragments of consecutive ML-IAP amino acid residues according to the present invention are listed herein below. The fragments can be selected from the sequence of amino acid residues of full-length ML-IAP listed herein below as SEQ ID NO:1:

```
mgpkdsakcl hrgpqpshwa agdgptqerc gprslgspvl gldtcrawdh vdgqilgqlr plteeeeeeg agatlsrgpa fpgmgseelr lasfydwplt aevppellaa agffhtghqd kvrcffcygg lqswkrgddp wthakwfpsc qfllrskgrd fvhsvqeths qllgswdpwe epedaapvap svpasgypel ptprrevqse saqepggvsp aeaqrawwvl eppgardvea qirriqeert ckvcldravs ivfvpcghlv caecapglql cpicrapvrs rvrtfls (SEQ ID NO:1).
```

It is not possible to readily predict which fragments of a given polypeptide, such as ML-IAP will constitute good antigens or efficient targets for spontaneous CTL responses. Thus, it is critical to identify peptides, which are suitable as antigens. The present invention provides methods for testing fragments of ML-IAP, i.e. tests for binding affinity to HLA molecules, elicited CTL response and/or any other antigenic properties to identify those fragments of ML-IAP which constitute good antigens. Furthermore, the invention provides useful ML-IAP peptides.

The binding of peptides to the MHC is a crucial step in the generation of a T cell response. Thus, a commonly used way of identifying CTL epitopes is the use of sophisticated algorithms, which incorporate information about the contribution of all peptide side-chains to the overall binding of a particular peptide in an attempt to improve the prediction of CTL epitopes. However, firstly it has been described that there is no strong correlation between actual and predicted peptide binding to MHC from computer algorithms (20). Secondly, peptide binding to MHC is one of a number of different factors which determine the immunogenicity of a given peptide. These include expression level of the relevant source protein, processing, TAP-transport, expression level of the class I MHC on the cell surface, TCR repertoire, CTL sensitivity, immuno-suppression and cytokines (23). Thus, there are many factors, which determine a CTL response against a given peptide. Furthermore, many immunodominant epitopes in CTL responses to self proteins may frequently be subdominant or cryptic, rather than dominant determinants. The identification of CTL epitopes from a given protein is therefore a complicated manner.

Fragments Comprising a Sequence of 9 Consecutive Amino Acid Residues of ML-IAP

The present invention in one preferred embodiment is directed to fragments of ML-IAP comprising at least 9 consecutive amino acid residues and vaccine compositions comprising fragments of ML-IAP comprising at least 9 consecutive amino acid residues, including the fragments listed herein below:

mgpkdsakc (SEQ ID NO:2); gpkdsakcl (SEQ ID NO:3); pkdsakclh (SEQ ID NO:4); kdsakclhr (SEQ ID NO:5); dsakclhrg (SEQ ID NO:6); sakclhrgp (SEQ ID NO:7); akclhrgpq (SEQ ID NO:8); kclhrgpqp (SEQ ID NO:9); clhrgpqps (SEQ ID NO:10); lhrgpqpsh (SEQ ID NO:11); hrgpqpshw (SEQ ID NO:12); rgpqpshwa (SEQ ID NO:13); gpqpshwaa (SEQ ID NO:14); pqpshwaag (SEQ ID NO:15); qpshwaagd (SEQ ID NO:16); pshwaagdg (SEQ ID NO:17); shwaagdgp (SEQ ID NO:18); hwaagdgpt (SEQ ID NO:19); waagdgptq (SEQ ID NO:20); aagdgptqe (SEQ ID NO:21); agdgptqer (SEQ ID NO:22); gdgptqerc (SEQ ID NO:23); dgptqercg (SEQ ID NO:24); gptqercgp (SEQ ID NO:25); ptqercgpr (SEQ ID NO:26); tqercgprs (SEQ ID NO:27); qercgprsl (SEQ ID NO:28); ercgprslg (SEQ ID NO:29); rcgprslgs (SEQ ID NO:30); cgprslgsp (SEQ ID NO:31); gprslgspv (SEQ ID NO:32); prslgspvl (SEQ ID NO:33); rslgspvlg (SEQ ID NO:34); slgspvlgl (SEQ ID NO:35); lgspvlgld (SEQ ID NO:36); gspvlgldt (SEQ ID NO:37); spvlgldtc (SEQ ID NO:38); pvlgldtcr (SEQ ID NO:39); vlgldtcra (SEQ ID NO:40); lgldtcraw (SEQ ID NO:41); gldtcrawd (SEQ ID NO:42); ldtcrawdh (SEQ ID NO:43); dtcrawdhv (SEQ ID NO:44); tcrawdhvd (SEQ ID NO:45); crawdhvdg (SEQ ID NO:46); rawdhvdgq (SEQ ID NO:47); awdhvdgqi (SEQ ID NO:48); wdhvdgqil (SEQ ID NO:49); dhvdgqilg (SEQ ID NO:50); hvdgqilgq (SEQ ID NO:51); vdgqilgql (SEQ ID NO:52); dgqilgqlr (SEQ ID NO:53); gqilgqlrp (SEQ ID NO:54); qilgqlrpl (SEQ ID NO:55); ilgqlrplt (SEQ ID NO:56); lgqlrplte (SEQ ID NO:57); gqlrpltee (SEQ ID NO:58); qlrplteee (SEQ ID NO:59); lrplteeee (SEQ ID NO:60); rplteeeee (SEQ ID NO:61); plteeeeee (SEQ ID NO:62); lteeeeeeg (SEQ ID NO:63); teeeeeega (SEQ ID NO:64); eeeeeegag (SEQ ID NO:65); eeeeegaga (SEQ ID NO:66); eeeegagat (SEQ ID NO:67); eeegagatl (SEQ ID NO:68); eegagatls (SEQ ID NO:69); egagatlsr (SEQ ID NO:70); gagatlsrg (SEQ ID NO:71); agatlsrgp (SEQ ID NO:72); gatlsrgpa (SEQ ID NO:73); atlsrgpaf (SEQ ID NO:74); tlsrgpafp (SEQ ID NO:75); lsrgpafpg (SEQ ID NO:76); srgpafpgm (SEQ ID NO:77); rgpafpgmg (SEQ ID NO:78); gpafpgmgs (SEQ ID NO:79); pafpgmgse (SEQ ID NO:80); afpgmgsee (SEQ ID NO:81); fpgmgseel (SEQ ID NO:82); pgmgseelr (SEQ ID NO:83); gmgseelrl (SEQ ID NO:84); mgseelrla (SEQ ID NO:85); gseelrlas (SEQ ID NO:86); seelrlasf (SEQ ID NO:87); eelrlasfy (SEQ ID NO:88); elrlasfyd (SEQ ID NO:89); lrlasfydw (SEQ ID NO:90); rlasfydwp (SEQ ID NO:91); lasfydwpl (SEQ ID NO:92); asfydwplt (SEQ ID NO:93); sfydwplta (SEQ ID NO:94); fydwpltae (SEQ ID NO:95); ydwpltaev (SEQ ID NO:96); dwpltaevp (SEQ ID NO:97); wpltaevpp (SEQ ID NO:98); pltaevppe (SEQ ID NO:99); ltaevppel (SEQ ID NO:100); taevppell (SEQ ID NO:101); aevppella (SEQ ID NO:102); evppellaa (SEQ ID NO:103); vppellaaa (SEQ ID NO:104); ppellaaag (SEQ ID NO:105); pelaaagf (SEQ ID NO:106); ellaaagff (SEQ ID NO:107); llaaagffh (SEQ ID NO:108); laaagffht (SEQ ID NO:109); aaagffhtg (SEQ ID NO: 110); aagffhtgh (SEQ ID NO:111); agffhtghq (SEQ ID NO:112); gffhtghqd (SEQ ID NO:113); ffhtghqdk (SEQ ID NO:114); fhtghqdkv (SEQ ID NO:115); htghqdkvr (SEQ ID NO:116); tghqdkvrc (SEQ ID NO:117); ghqdkvrcf (SEQ ID NO:118); hqdkvrcff (SEQ ID NO:119); qdkvrcffc (SEQ ID NO:120); dkvrcffcy (SEQ ID NO:121); kvrcffcyg (SEQ ID NO:122); vrcffcygg (SEQ ID NO:123); rcffcyggl (SEQ ID NO:124); cffcygglq (SEQ ID NO:125); ffcygglqs (SEQ ID NO:126); fcygglqsw (SEQ ID NO:127); cygglqswk (SEQ ID NO:128); ygglqswkr (SEQ ID NO:129); gglqswkrg (SEQ ID NO:130); glqswkrgd (SEQ ID NO:131); lqswkrgdd (SEQ ID NO:132); qswkrgddp (SEQ ID NO:133); swkrgddpw (SEQ ID NO:134); wkrgddpwt (SEQ ID NO:135); krgddpwth (SEQ ID NO:136); rgddpwtha (SEQ ID NO:137); gddpwthak (SEQ ID NO:138); ddpwthakw (SEQ ID NO:139); dpwthakwf (SEQ ID NO:140); pwthakwfp (SEQ ID NO:141); wthakwfps (SEQ ID NO:142); thakwfpsc (SEQ ID NO:143); hakwfpscq (SEQ ID NO:144); akwfpscqf (SEQ ID NO:145); kwfpscqfl (SEQ ID NO:146); wfpscqfll (SEQ ID NO:147); fpscqfllr (SEQ ID NO:148); pscqfllrs (SEQ ID NO:149); scqfllrsk (SEQ ID NO:150); cqfllrskg (SEQ ID NO:151); qfllrskgr (SEQ ID NO:152); fllrskgrd (SEQ ID NO:153); llrskgrdf (SEQ ID NO:154); lrskgrdfv (SEQ ID NO:155); rskgrdfvh (SEQ ID NO:156); skgrdfvhs (SEQ ID NO:157); kgrdfvhsv (SEQ ID NO:158); grdfvhsvq (SEQ ID NO:159); rdfvhsvqe (SEQ ID NO:160); dfvhsvqet (SEQ ID NO:161); fvhsvqeth (SEQ ID NO:162); vhsvqeths (SEQ ID NO:163); hsvqethsq (SEQ ID NO:164); svqethsql (SEQ ID NO:165); vqethsqll (SEQ ID NO:166); qethsqllg (SEQ ID NO:167); ethsqllgs (SEQ ID NO:168); thsqllgsw (SEQ ID NO:169); hsqllgswd (SEQ ID NO:170); sqllgswdp (SEQ ID NO:171); qllgswdpw (SEQ ID NO:172); llgswdpwe (SEQ ID NO:173); lgswdpwee (SEQ ID NO:174); gswdpweep (SEQ ID NO:175); swdpweepe (SEQ ID NO:176); wdpweeped (SEQ ID NO:177); dpweepeda (SEQ ID NO:178); pweepedaa (SEQ ID NO:179); weepedaap (SEQ ID NO:180); eepedaapv (SEQ ID NO:181); epedaapva (SEQ ID NO:182); pedaapvap (SEQ ID NO:183); edaapvaps (SEQ ID NO:184); daapvapsv (SEQ ID NO:185); aapvapsvp (SEQ ID NO:186); apvapsvpa (SEQ ID NO:187); pvapsvpas (SEQ ID NO:188); vapsvpasg (SEQ ID NO:189); apsvpasgy (SEQ ID NO:190); psvpasgyp (SEQ ID NO:191); svpasgype (SEQ ID NO:192); vpasgypel (SEQ ID NO:193); pasgypelp (SEQ ID NO:194); asgypelpt (SEQ ID NO:195); sgypelptp (SEQ ID NO:196); gypelptpr (SEQ ID NO:197); ypelptprr (SEQ ID NO:198); pelptprre (SEQ ID NO:199); elptprrev (SEQ ID NO:200); lptprrevq (SEQ ID NO:201); ptprrevqs (SEQ ID NO:202); tprrevqse (SEQ ID NO:203); prrevqses (SEQ ID NO:204); rrevqsesa (SEQ ID NO:205); revqsesaq (SEQ ID NO:206); evqsesaqe (SEQ ID NO:207); vqsesaqep (SEQ ID NO:208); qsesaqepg (SEQ ID NO:209); sesaqepgg (SEQ ID NO:210); esaqepggv (SEQ ID NO:211); saqepggvs (SEQ ID NO:212); aqepggvsp (SEQ ID NO:213); qepggvspa (SEQ ID NO:214); epggvspae (SEQ ID NO:215); pggvspaea (SEQ ID NO:216); ggvspaeaq (SEQ ID NO:217); gvspaeaqr (SEQ ID NO:218); vspaeaqra (SEQ ID NO:219); spaeaqraw (SEQ ID NO:220); paeaqraww (SEQ ID NO:221); aeaqrawwv (SEQ ID NO:222); eaqrawwvl (SEQ ID NO:223); aqrawwvle (SEQ ID NO:224); qrawwvlep (SEQ ID NO:225); rawwvlepp (SEQ ID NO:226); awwvleppg (SEQ ID NO:227); wwvleppga (SEQ ID NO:228); wvleppgar (SEQ ID NO:229); vleppgard (SEQ ID NO:230); leppgardv (SEQ ID NO:231); eppgardve (SEQ ID NO:232); ppgardvea (SEQ ID NO:233); pgardveaq (SEQ ID NO:234); gardveaql (SEQ ID NO:235); ardveaqlr (SEQ ID NO:236); rdveaqlrr (SEQ ID NO:237); dveaqlrrl (SEQ ID NO:238); veaqlrrlq (SEQ ID NO:239); eaqlrriqe (SEQ ID NO:240); aqlrriqee (SEQ ID NO:241); qlrriqeer (SEQ ID NO:242); lrriqeert (SEQ ID NO:243); rrlqeertc (SEQ ID NO:244); rlqeertck (SEQ ID NO:245); lqeertckv (SEQ ID NO:246); qeertckvc (SEQ ID NO:247); eertckvcl (SEQ ID NO:248); ertckvcld (SEQ ID NO:249); rtckvcldr (SEQ ID NO:250); tckvcldra (SEQ ID NO:251); ckvcldrav (SEQ ID NO:252); kvcldravs (SEQ ID NO:253); vcldravsi (SEQ ID NO:254); cldravsiv (SEQ ID NO:255); ldravsivf (SEQ ID NO:256); dravsivfv (SEQ ID NO:257); ravsivfvp (SEQ ID NO:258); avsivfvpc (SEQ ID NO:259); vsivfvpcg (SEQ ID NO:260); sivfvpcgh (SEQ ID NO:261); ivfvpcghl (SEQ ID NO:262); vfvpcghlv (SEQ ID NO:263); fvpcghlvc (SEQ ID NO:264); vpcghlvca (SEQ ID NO:265); pcghlvcae (SEQ ID NO:266); cghlvcaec (SEQ ID NO:267); ghlvcaeca (SEQ ID NO:268); hlvcaecap (SEQ ID NO:269); lvcaecapg (SEQ ID NO:270); vcaecapgl (SEQ ID NO:271); caecapglq (SEQ ID NO:272); aecapglql (SEQ ID NO:273); ecapglqlc (SEQ ID NO:274); capglqlcp (SEQ ID NO:275); apglqlcpi (SEQ ID NO:276); pglqlcpic (SEQ ID NO:277); glqlcpicr (SEQ ID NO:278); lqlcpicra (SEQ ID NO:279); qlcpicrap (SEQ ID NO:280); lcpicrapv (SEQ ID NO:281); cpicrapvr (SEQ ID NO:282); picrapvrs (SEQ ID NO:283); icrapvrsr (SEQ ID NO:284); crapvrsrv (SEQ ID NO:285); rapvrsrvr (SEQ ID NO:286); apvrsrvrt (SEQ ID NO:287); pvrsrvrtf (SEQ ID NO:288); vrsrvrtfl (SEQ ID NO:289); rsrvrtfls (SEQ ID NO:290).

In one embodiment of the present invention the fragment is preferably not SEQ ID NO:35.

Fragments Comprising a Sequence of 10 Consecutive Amino Acid Residues of ML-IAP

The present invention also relates to fragments comprising or consisting of 10 consecutive amino acid residues of ML-IAP (SEQ ID NO:1), such as e.g. the 10 most N-terminal amino acid residues of SEQ ID NO:1, i.e. mgpkdsakcl (SEQ ID NO:291), as well as vaccine compositions comprising such fragments. Additional fragments comprising or consisting of 10 consecutive amino acid residues of ML-IAP can thus be obtained in the following way: selecting any one of the above fragments defined by SEQ ID NO:3 to SEQ ID NO:289 (i.e. a fragment listed above defined by SEQ ID NO:N, wherein N is an integer larger than 2 and smaller than 290), and adding the C-terminal amino acid residue of SEQ ID NO:N+1 to the C-terminal amino acid residue of the fragment selected in step i).

In one embodiment of the present invention the fragment is preferably not SEQ ID NO:299.

Fragments Comprising a Sequence of 11 Consecutive Amino Acid Residues of ML-IAP

The present invention also relates to fragments comprising or consisting of 11 consecutive amino acid residues of ML-IAP (SEQ ID NO:1), such as e.g. the 11 most N-terminal amino acid residues of SEQ ID NO:1, i.e. mgpkdsakclh (SEQ ID NO:292), as well as vaccine compositions comprising such fragments. Additional fragments comprising or consisting of 11 consecutive amino acid residues of ML-IAP can thus be obtained in the following way:

selecting any one of the above fragments defined by SEQ ID NO:3 to SEQ ID NO:288 (i.e. a fragment listed above defined by SEQ ID NO:N, wherein N is an integer larger than 2 and smaller than 289), and adding the 2 most C-terminal amino acid residues of SEQ ID NO:N+2 to the C-terminal amino acid residue of the fragment selected in step i).

Fragments Comprising a Sequence of 12 Consecutive Amino Acid Residues of ML-IAP

The present invention also relates to fragments comprising or consisting of 12 consecutive amino acid residues of ML-IAP (SEQ ID NO:1), such as e.g. the 12 most N-terminal amino acid residues of SEQ ID NO:1, i.e. mgpkdsakclhr (SEQ ID NO:293), as well as vaccine compositions comprising such fragments. Additional fragments comprising or consisting of 12 consecutive amino acid residues of ML-IAP can thus be obtained in the following way:

selecting any one of the above fragments defined by SEQ ID NO:3 to SEQ ID NO:287 (i.e. a fragment listed above defined by SEQ ID NO:N, wherein N is an integer larger than 2 and smaller than 288), and adding the 3 most C-terminal amino acid residues of SEQ ID NO:N+3 to the C-terminal amino acid residue of the fragment selected in step i).

Fragments Comprising a Sequence of 13 Consecutive Amino Acid Residues of ML-IAP

The present invention also relates to fragments comprising or consisting of 13 consecutive amino acid residues of ML-IAP (SEQ ID NO:1), such as e.g. the 13 most N-terminal amino acid residues of SEQ ID NO:1, i.e. mgpkdsakclhrg (SEQ ID NO:294), as well as vaccine compositions comprising such fragments. Additional fragments comprising or consisting of 13 consecutive amino acid residues of ML-IAP can thus generally be obtained in the following way:

selecting any one of the above fragments defined by SEQ ID NO:3 to SEQ ID NO:286 (i.e. a fragment listed above defined by SEQ ID NO:N, wherein N is an integer larger than 2 and smaller than 287), and adding the 4 most C-terminal amino acid residues of SEQ ID NO:N+4 to the C-terminal amino acid residue of the fragment selected in step i).

Fragments Comprising a Sequence of 14 Consecutive Amino Acid Residues of ML-IAP

The present invention also relates to fragments comprising or consisting of 14 consecutive amino acid residues of ML-IAP (SEQ ID NO:1), such as e.g. the 14 most N-terminal amino acid residues of SEQ ID NO:1, i.e. mgpkdsakclhrgp (SEQ ID NO:295), as well as vaccine compositions comprising such fragments. Additional fragments comprising or consisting of 14 consecutive amino acid residues of ML-IAP can thus generally be obtained in the following way:

selecting any one of the above fragments defined by SEQ ID NO:3 to SEQ ID NO:285 (i.e. a fragment listed above defined by SEQ ID NO:N, wherein N is an integer larger than 2 and smaller than 286), and adding the 5 most C-terminal amino acid residues of SEQ ID NO:N+5 to the C-terminal amino acid residue of the fragment selected in step i).

Fragments Comprising a Sequence of 15 Consecutive Amino Acid Residues of ML-IAP

The present invention also relates to fragments comprising or consisting of 15 consecutive amino acid residues of ML-IAP (SEQ ID NO:1), such as e.g. the 15 most N-terminal amino acid residues of SEQ ID NO:1, i.e. mgpkdsakclhrgpq (SEQ ID NO:296), as well as vaccine compositions comprising such fragments. Additional fragments comprising or consisting of 15 consecutive amino acid residues of ML-IAP can thus generally be obtained in the following way:

selecting any one of the above fragments defined by SEQ ID NO:3 to SEQ ID NO:284 (i.e. a fragment listed above defined by SEQ ID NO:N, wherein N is an integer larger than 2 and smaller than 285), and adding the 6 most C-terminal amino acid residues of SEQ ID NO:N+6 to the C-terminal amino acid residue of the fragment selected in step i).

Accordingly, for any of the above fragments of ML-IAP comprising or consisting of from 10 to 15 consecutive amino acid residues of ML-IAP, N is an integer of from 3 to preferably less than 290, such as 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284 (fragments comprising or consisting of 15 or less consecutive amino acid residues of ML-IAP), 285 (fragments comprising or consisting of 14 or less consecutive amino acid residues of ML-IAP), 286 (fragments comprising or consisting of 13 or less consecutive amino acid residues of ML-IAP), 287 (fragments comprising or consisting of 12 or less consecutive amino acid residues of ML-IAP), 288 (fragments comprising or consisting of 11 or less consecutive amino acid residues of ML-IAP), 289 (fragments comprising or consisting of 10 or less consecutive amino acid residues of ML-IAP).

Accordingly, in preferred embodiments the present invention is directed to fragments of ML-IAP comprising or consisting of more than 9 consecutive amino acid residues. Such fragments can comprise for example 10 amino acid residues, such as 11 amino acid residues, for example 12 amino acid residues, such as 13 amino acid residues, for example 14 amino acid residues, such as 15 amino acid residues, for example 16 amino acid residues, such as 17 amino acid residues, for example 18 amino acid residues, such as 19 amino acid residues, for example 20 amino acid residues, such as 21 amino acid residues, for example 22 amino acid residues, such as 23 amino acid residues, for example 24 amino acid residues, such as 25 amino acid residues, for example 26 amino acid residues, such as 27 amino acid residues, for example 28 amino acid residues, such as 29 amino acid residues, for example 30 amino acid residues, such as 31 amino acid residues, for example 32 amino acid residues, such as 33 amino acid residues, for example 34 amino acid residues, such as 35 amino acid residues, for example 36 amino acid residues, such as 37 amino acid residues, for example 38 amino acid residues, such as 39 amino acid residues, for example 40 amino acid residues, such as 41 amino acid residues, for example 42 amino acid residues, such as 43 amino acid residues, for example 44 amino acid residues, such as 45 amino acid residues, for example 46 amino acid residues, such as 47 amino acid residues, for example 48 amino acid residues, such as 49 amino acid residues, for example 50 amino acid residues, such as 51 amino acid residues, for example 52 amino acid residues, such as 53 amino acid residues, for example 54 amino acid residues, such as 55 amino acid residues, for example 56 amino acid residues, such as 57 amino acid residues, for example 58 amino acid residues, such as 59 amino acid residues, for example 60 amino acid residues, such as 61 amino acid residues, for example 62 amino acid residues, such as 63 amino acid residues, for example 64 amino acid residues, such as 65 amino acid residues, for example 66 amino acid residues, such as 67 amino acid residues, for example 68 amino acid residues, such as 69 amino acid residues, for example 70 amino acid residues, such as 71 amino acid residues, for example 72 amino acid residues, such as 73 amino acid residues, for example 74 amino acid residues, such as 75 amino acid residues, for example 76 amino acid residues, such as 77 amino acid residues, for example 78 amino acid residues, such as 79 amino acid residues, for example 80 amino acid residues, such as 81 amino acid residues, for example 82 amino acid residues, such as 83 amino acid residues, for example 84 amino acid residues, such as 85 amino acid residues, for example 86 amino acid residues, such as 87 amino acid residues, for example 88 amino acid residues, such as 89 amino acid residues, for example 90 amino acid residues, such as 91 amino acid residues, for example 92 amino acid residues, such as 93 amino acid residues, for example 94 amino acid residues, such as 95 amino acid residues, for example 96 amino acid residues, such as 97 amino acid residues, for example 98 amino acid residues, such as 99 amino acid residues, for example 100 amino acid residues, such as 101 amino acid residues, for example 102 amino acid residues, such as 103 amino acid residues, for example 104 amino acid residues, such as 105 amino acid residues, for example 106 amino acid residues, such as 107 amino acid residues, for example 108 amino acid residues, such as 109 amino acid residues, for example 110 amino acid residues, such as 111 amino acid residues, for example 112 amino acid residues, such as 113 amino acid residues, for example 114 amino acid residues, such as 115 amino acid residues, for example 116 amino acid residues, such as 117 amino acid residues, for example 118 amino acid residues, such as 119 amino acid residues, for example 120 amino acid residues, such as 121 amino acid residues, for example 122 amino acid residues, such as 123 amino acid residues, for example 124 amino acid residues, such as 125 amino acid residues, for example 126 amino acid residues, such as 127 amino acid residues, for example 128 amino acid residues, such as 129 amino acid residues, for example 130 amino acid residues, such as 131 amino acid residues, for example 132 amino acid residues, such as 133 amino acid residues, for example 134 amino acid residues, such as 135 amino acid residues, for example 136 amino acid residues, such as 137 amino acid residues, for example 138 amino acid residues, such as 139 amino acid residues, for example 140 amino acid residues, such as 141 amino acid residues, for example 142 amino acid residues, such as 143 amino acid residues, for example 144 amino acid residues, such as 145 amino acid residues, for example 146 amino acid residues, such as 147 amino acid residues, for example 148 amino acid residues, such as 149 amino acid residues, for example 150 amino acid residues, such as 151 amino acid residues, for example 152 amino acid residues, such as 153 amino acid residues, for example 154 amino acid residues, such as 155 amino acid residues, for example 156 amino acid residues, such as 157 amino acid residues, for example 158 amino acid residues, such as 159 amino acid residues, for example 160 amino acid residues, such as 161 amino acid residues, for example 162 amino acid residues, such as 163 amino acid residues, for example 164 amino acid residues, such as 165 amino acid residues, for example 166 amino acid residues, such as 167 amino acid residues, for example 168 amino acid residues, such as 169 amino acid residues, for example 170 amino acid residues, such as 171 amino acid residues, for example 172 amino acid residues, such as 173 amino acid residues, for example 174 amino acid residues, such as 175 amino acid residues, for example 176 amino acid residues, such as 177 amino acid residues, for example 178 amino acid residues, such as 179 amino acid residues, for example 180 amino acid residues, such as 181 amino acid residues, for example 182 amino acid residues, such as 183 amino acid residues, for example 184 amino acid residues, such as 185 amino acid residues, for example 186 amino acid residues, such as 187 amino acid residues, for example 188 amino acid residues, such as 189 amino acid residues, for example 190 amino acid residues, such as 191 amino acid residues, for example 192 amino acid residues, such as 193 amino acid residues, for example 194 amino acid residues, such as 195 amino acid residues, for example 196 amino acid residues, such as 197 amino acid residues, for example 198 amino acid residues, such as 199 amino acid residues, for example 200 amino acid residues, such as 201 amino acid residues, for example 202 amino acid residues, such as 203 amino acid residues, for example 204 amino acid residues, such as 205 amino acid residues, for example 206 amino acid residues, such as 207 amino acid residues, for example 208 amino acid residues, such as 209 amino acid residues, for example 210 amino acid residues, such as 211 amino acid residues, for example 212 amino acid residues, such as 213 amino acid residues, for example 214 amino acid residues, such as 215 amino acid residues, for example 216 amino acid residues, such as 217 amino acid residues, for example 218 amino acid residues, such as 219 amino acid residues, for example 220 amino acid residues, such as 221 amino acid residues, for example 222 amino acid residues, such as 223 amino acid residues, for example 224 amino acid residues, such as 225 amino acid residues, for example 226 amino acid residues, such as 227 amino acid residues, for example 228 amino acid residues, such as 229 amino acid residues, for example 230 amino acid residues, such as 231 amino acid residues, for example 232 amino acid residues, such as 233 amino acid residues, for example 234 amino acid residues, such as 235 amino acid residues, for example 236 amino acid residues, such as 237 amino acid residues, for example 238 amino acid residues, such as 239 amino acid residues, for example 240 amino acid residues, such as 241 amino acid residues, for example 242 amino acid residues, such as 243 amino acid residues, for example 244 amino acid residues, such as 245 amino acid residues, for example 246 amino acid residues, such as 247 amino acid residues, for example 248 amino acid residues, such as 249 amino acid residues, for example 250 amino acid residues, such as 251 amino acid residues, for example 252 amino acid residues, such as 253 amino acid residues, for example 254 amino acid residues, such as 255 amino acid residues, for example 256 amino acid residues, such as 257 amino acid residues, for example 258 amino acid residues, such as 259 amino acid residues, for example 260 amino acid residues, such as 261 amino acid residues, for example 262 amino acid residues, such as 263 amino acid residues, for example 264 amino acid residues, such as 265 amino acid residues, for example 266 amino acid residues, such as 267 amino acid residues, for example 268 amino acid residues, such as 269 amino acid residues, for example 270 amino acid residues, such as 271 amino acid residues, for example 272 amino acid residues, such as 273 amino acid residues, for example 274 amino acid residues, such as 275 amino acid residues, for example 276 amino acid residues, such as 277 amino acid residues, for example 278 amino acid residues, such as 279 amino acid residues, for example 280 amino acid residues, such as 281 amino acid residues, for example 282 amino acid residues, such as 283 amino acid residues, for example 284 amino acid residues, such as 285 amino acid residues, for example 286 amino acid residues, such as 287 amino acid residues, for example 288 amino acid residues, such as 289 amino acid residues, for example 290 amino acid residues, such as 291 amino acid residues, for example 292 amino acid residues, such as 293 amino acid residues, for example 294 amino acid residues, such as 295 amino acid residues, for example 296 amino acid residues, wherein the most N-terminal amino acid residue of each of the above fragments is for example residue 1 of SEQ ID NO:1, such as residue 2 of SEQ ID NO:1, for example residue 3 of SEQ ID NO:1, such as residue 4 of SEQ ID NO:1, for example residue 5 of SEQ ID NO:1, such as residue 6 of SEQ ID NO:1, for example residue 7 of SEQ ID NO:1, such as residue 8 of SEQ ID NO:1, for example residue 9 of SEQ ID NO:1, such as residue 10 of SEQ ID NO:1, for example residue 11 of SEQ ID NO:1, such as residue 12 of SEQ ID NO:1, for example residue 13 of SEQ ID NO:1, such as residue 14 of SEQ ID NO:1, for example residue 15 of SEQ ID NO:1, such as residue 16 of SEQ ID NO:1, for example residue 17 of SEQ ID NO:1, such as residue 18 of SEQ ID NO:1, for example residue 19 of SEQ ID NO:1, such as residue 20 of SEQ ID NO:1, for example residue 21 of SEQ ID NO:1, such as residue 22 of SEQ ID NO:1, for example residue 23 of SEQ ID NO:1, such as residue 24 of SEQ ID NO:1, for example residue 25 of SEQ ID NO:1, such as residue 26 of SEQ ID NO:1, for example residue 27 of SEQ ID NO:1, such as residue 28 of SEQ ID NO:1, for example residue 29 of SEQ ID NO:1, such as residue 30 of SEQ ID NO:1, for example residue 31 of SEQ ID NO:1, such as residue 32 of SEQ ID NO:1, for example residue 33 of SEQ ID NO:1, such as residue 34 of SEQ ID NO:1, for example residue 35 of SEQ ID NO:1, such as residue 36 of SEQ ID NO:1, for example residue 37 of SEQ ID NO:1, such as residue 38 of SEQ ID NO:1, for example residue 39 of SEQ ID NO:1, such as residue 40 of SEQ ID NO:1, for example residue 41 of SEQ ID NO:1, such as residue 42 of SEQ ID NO:1, for example residue 43 of SEQ ID NO:1, such as residue 44 of SEQ ID NO:1, for example residue 45 of SEQ ID NO:1, such as residue 46 of SEQ ID NO:1, for example residue 47 of SEQ ID NO:1, such as residue 48 of SEQ ID NO:1, for example residue 49 of SEQ ID NO:1, such as residue 50 of SEQ ID NO:1, for example residue 51 of SEQ ID NO:1, such as residue 52 of SEQ ID NO:1, for example residue 53 of SEQ ID NO:1, such as residue 54 of SEQ ID NO:1, for example residue 55 of SEQ ID NO:1, such as residue 56 of SEQ ID NO:1, for example residue 57 of SEQ ID NO:1, such as residue 58 of SEQ ID NO:1, for example residue 59 of SEQ ID NO:1, such as residue 60 of SEQ ID NO:1, for example residue 61 of SEQ ID NO:1, such as residue 62 of SEQ ID NO:1, for example residue 63 of SEQ ID NO:1, such as residue 64 of SEQ ID NO:1, for example residue 65 of SEQ ID NO:1, such as residue 66 of SEQ ID NO:1, for example residue 67 of SEQ ID NO:1, such as residue 68 of SEQ ID NO:1, for example residue 69 of SEQ ID NO:1, such as residue 70 of SEQ ID NO:1, for example residue 71 of SEQ ID NO:1, such as residue 72 of SEQ ID NO:1, for example residue 73 of SEQ ID NO:1, such as residue 74 of SEQ ID NO:1, for example residue 75 of SEQ ID NO:1, such as residue 76 of SEQ ID NO:1, for example residue 77 of SEQ ID NO:1, such as residue 78 of SEQ ID NO:1, for example residue 79 of SEQ ID NO:1, such as residue 80 of SEQ ID NO:1, for example residue 81 of SEQ ID NO:1, such as residue 82 of SEQ ID NO:1, for example residue 83 of SEQ ID NO:1, such as residue 84 of SEQ ID NO:1, for example residue 85 of SEQ ID NO:1, such as residue 86 of SEQ ID NO:1, for example residue 87 of SEQ ID NO:1, such as residue 88 of SEQ ID NO:1, for example residue 89 of SEQ ID NO:1, such as residue 90 of SEQ ID NO:1, for example residue 91 of SEQ ID NO:1, such as residue 92 of SEQ ID NO:1, for example residue 93 of SEQ ID NO:1, such as residue 94 of SEQ ID NO:1, for example residue 95 of SEQ ID NO:1, such as residue 96 of SEQ ID NO:1, for example residue 97 of SEQ ID NO:1, such as residue 98 of SEQ ID NO:1, for example residue 99 of SEQ ID NO:1, such as residue 100 of SEQ ID NO:1, for example residue 101 of SEQ ID NO:1, such as residue 102 of SEQ ID NO:1, for example residue 103 of SEQ ID NO:1, such as residue 104 of SEQ ID NO:1, for example residue 105 of SEQ ID NO:1, such as residue 106 of SEQ ID NO:1, for example residue 107 of SEQ ID NO:1, such as residue 108 of SEQ ID NO:1, for example residue 109 of SEQ ID NO:1, such as residue 110 of SEQ ID NO:1, for example residue 111 of SEQ ID NO:1, such as residue 112 of SEQ ID NO:1, for example residue 113 of SEQ ID NO:1, such as residue 114 of SEQ ID NO:1, for example residue 115 of SEQ ID NO:1, such as residue 116 of SEQ ID NO:1, for example residue 117 of SEQ ID NO:1, such as residue 118 of SEQ ID NO:1, for example residue 119 of SEQ ID NO:1, such as residue 120 of SEQ ID NO:1, for example residue 121 of SEQ ID NO:1, such as residue 122 of SEQ ID NO:1, for example residue 123 of SEQ ID NO:1, such as residue 124 of SEQ ID NO:1, for example residue 125 of SEQ ID NO:1, such as residue 126 of SEQ ID NO:1, for example residue 127 of SEQ ID NO:1, such as residue 128 of SEQ ID NO:1, for example residue 129 of SEQ ID NO:1, such as residue 130 of SEQ ID NO:1, for example residue 131 of SEQ ID NO:1, such as residue 132 of SEQ ID NO:1, for example residue 133 of SEQ ID NO:1, such as residue 134 of SEQ ID NO:1, for example residue 135 of SEQ ID NO:1, such as residue 136 of SEQ ID NO:1, for example residue 137 of SEQ ID NO:1, such as residue 138 of SEQ ID NO:1, for example residue 139 of SEQ ID NO:1, such as residue 140 of SEQ ID NO:1, for example residue 141 of SEQ ID NO:1, such as residue 142 of SEQ ID NO:1, for example residue 143 of SEQ ID NO:1, such as residue 144 of SEQ ID NO:1, for example residue 145 of SEQ ID NO:1, such as residue 146 of SEQ ID NO:1, for example residue 147 of SEQ ID NO:1, such as residue 148 of SEQ ID NO:1, for example residue 149 of SEQ ID NO:1, such as residue 150 of SEQ ID NO:1, for example residue 151 of SEQ ID NO:1, such as residue 152 of SEQ ID NO:1, for example residue 153 of SEQ ID NO:1, such as residue 154 of SEQ ID NO:1, for example residue 155 of SEQ ID NO:1, such as residue 156 of SEQ ID NO:1, for example residue 157 of SEQ ID NO:1, such as residue 158 of SEQ ID NO:1, for example residue 159 of SEQ ID NO:1, such as residue 160 of SEQ ID NO:1, for example residue 161 of SEQ ID NO:1, such as residue 162 of SEQ ID NO:1, for example residue 163 of SEQ ID NO:1, such as residue 164 of SEQ ID NO:1, for example residue 165 of SEQ ID NO:1, such as residue 166 of SEQ ID NO:1, for example residue 167 of SEQ ID NO:1, such as residue 168 of SEQ ID NO:1, for example residue 169 of SEQ ID NO:1, such as residue 170 of SEQ ID NO:1, for example residue 171 of SEQ ID NO:1, such as residue 172 of SEQ ID NO:1, for example residue 173 of SEQ ID NO:1, such as residue 174 of SEQ ID NO:1, for example residue 175 of SEQ ID NO:1, such as residue 176 of SEQ ID NO:1, for example residue 177 of SEQ ID NO:1, such as residue 178 of SEQ ID NO:1, for example residue 179 of SEQ ID NO:1, such as residue 180 of SEQ ID NO:1, for example residue 181 of SEQ ID NO:1, such as residue 182 of SEQ ID NO:1, for example residue 183 of SEQ ID NO:1, such as residue 184 of SEQ ID NO:1, for example residue 185 of SEQ ID NO:1, such as residue 186 of SEQ ID NO:1, for example residue 187 of SEQ ID NO:1, such as residue 188 of SEQ ID NO:1, for example residue 189 of SEQ ID NO:1, such as residue 190 of SEQ ID NO:1, for example residue 191 of SEQ ID NO:1, such as residue 192 of SEQ ID NO:1, for example residue 193 of SEQ ID NO:1, such as residue 194 of SEQ ID NO:1, for example residue 195 of SEQ ID NO:1, such as residue 196 of SEQ ID NO:1, for example residue 197 of SEQ ID NO:1, such as residue 198 of SEQ ID NO:1, for example residue 199 of SEQ ID NO:1, such as residue 200 of SEQ ID NO:1, for example residue 201 of SEQ ID NO:1, such as residue 202 of SEQ ID NO:1, for example residue 203 of SEQ ID NO:1, such as residue 204 of SEQ ID NO:1, for example residue 205 of SEQ ID NO:1, such as residue 206 of SEQ ID NO:1, for example residue 207 of SEQ ID NO:1, such as residue 208 of SEQ ID NO:1, for example residue 209 of SEQ ID NO:1, such as residue 210 of SEQ ID NO:1, for example residue 211 of SEQ ID NO:1, such as residue 212 of SEQ ID NO:1, for example residue 213 of SEQ ID NO:1, such as residue 214 of SEQ ID NO:1, for example residue 215 of SEQ ID NO:1, such as residue 216 of SEQ ID NO:1, for example residue 217 of SEQ ID NO:1, such as residue 218 of SEQ ID NO:1, for example residue 219 of SEQ ID NO:1, such as residue 220 of SEQ ID NO:1, for example residue 221 of SEQ ID NO:1, such as residue 222 of SEQ ID NO:1, for example residue 223 of SEQ ID NO:1, such as residue 224 of SEQ ID NO:1, for example residue 225 of SEQ ID NO:1, such as residue 226 of SEQ ID NO:1, for example residue 227 of SEQ ID NO:1, such as residue 228 of SEQ ID NO:1, for example residue 229 of SEQ ID NO:1, such as residue 230 of SEQ ID NO:1, for example residue 231 of SEQ ID NO:1, such as residue 232 of SEQ ID NO:1, for example residue 233 of SEQ ID NO:1, such as residue 234 of SEQ ID NO:1, for example residue 235 of SEQ ID NO:1, such as residue 236 of SEQ ID NO:1, for example residue 237 of SEQ ID NO:1, such as residue 238 of SEQ ID NO:1, for example residue 239 of SEQ ID NO:1, such as residue 240 of SEQ ID NO:1, for example residue 241 of SEQ ID NO:1, such as residue 242 of SEQ ID NO:1, for example residue 243 of SEQ ID NO:1, such as residue 244 of SEQ ID NO:1, for example residue 245 of SEQ ID NO:1, such as residue 246 of SEQ ID NO:1, for example residue 247 of SEQ ID NO:1, such as residue 248 of SEQ ID NO:1, for example residue 249 of SEQ ID NO:1, such as residue 250 of SEQ ID NO:1, for example residue 251 of SEQ ID NO:1, such as residue 252 of SEQ ID NO:1, for example residue 253 of SEQ ID NO:1, such as residue 254 of SEQ ID NO:1, for example residue 255 of SEQ ID NO:1, such as residue 256 of SEQ ID NO:1, for example residue 257 of SEQ ID NO:1, such as residue 258 of SEQ ID NO:1, for example residue 259 of SEQ ID NO:1, such as residue 260 of SEQ ID NO:1, for example residue 261 of SEQ ID NO:1, such as residue 262 of SEQ ID NO:1, for example residue 263 of SEQ ID NO:1, such as residue 264 of SEQ ID NO:1, for example residue 265 of SEQ ID NO:1, such as residue 266 of SEQ ID NO:1, for example residue 267 of SEQ ID NO:1, such as residue 268 of SEQ ID NO:1, for example residue 269 of SEQ ID NO:1, such as residue 270 of SEQ ID NO:1, for example residue 271 of SEQ ID NO:1, such as residue 272 of SEQ ID NO:1, for example residue 273 of SEQ ID NO:1, such as residue 274 of SEQ ID NO:1, for example residue 275 of SEQ ID NO:1, such as residue 276 of SEQ ID NO:1, for example residue 277 of SEQ ID NO:1, such as residue 278 of SEQ ID NO:1, for example residue 279 of SEQ ID NO:1, such as residue 280 of SEQ ID NO:1, for example residue 281 of SEQ ID NO:1, such as residue 282 of SEQ ID NO:1, for example residue 283 of SEQ ID NO:1, such as residue 284 of SEQ ID NO:1, for example residue 285 of SEQ ID NO:1, such as residue 286 of SEQ ID NO:1, for example residue 287 of SEQ ID NO:1, such as residue 288 of SEQ ID NO:1, for example residue 289 of SEQ ID NO:1, such as residue 290 of SEQ ID NO:1, for example residue 291 of SEQ ID NO:1, such as residue 292 of SEQ ID NO:1, for example residue 293 of SEQ ID NO:1, such as residue 294 of SEQ ID NO:1, for example residue 295 of SEQ ID NO:1, such as residue 296 of SEQ ID NO:1, for example residue 297 of SEQ ID NO:1, with the proviso that the length of a given fragment, measured as the number of amino acid residues, is shorter than or equal to the result obtained by subtracting from 297 (the number of residues in the full-length ML-IAP sequence) the position (number) in SEQ ID NO:1 of the N-terminal amino acid residue of the fragment in question.

Much preferred fragments of ML-IAP are listed herein below in Table 1 and characterised by their $C_{50}$ value (μM) as the concentration of the peptide required for half maximal binding to HLA-A2. The value range listed in subscript indicates the position of the first amino acid in the sequence.

TABLE 1

| ML-IAP fragment | Sequence | | | $C_{50}$ (μM) |
|---|---|---|---|---|
| ML-IAP$_{245}$ | RLQEERTCKV | (SEQ ID NO:297) | | 1 |
| ML-IAP$_{280}$ | QLCPICRAPV | (SEQ ID NO:298) | | 20 |
| ML-IAP$_{90}$ | RLASFYDWPL | (SEQ ID NO:299) | | 0.2 |
| ML-IAP$_{154}$ | LLRSKGRDFV | (SEQ ID NO:300) | | 10 |
| ML-IAP$_{230}$ | VLEPPGARDV | (SEQ ID NO:301) | | >100 |
| ML-IAP$_{98}$ | PLTAEVPPEL | (SEQ ID NO:302) | | >100 |
| ML-IAP$_{261}$ | SIVFVPCG | | | Not binding |
| ML-IAP$_{34}$ | SLGSPVLGL | (SEQ ID NO:35) | | 1 |
| ML-IAP$_{54}$ | QILGQLRPL | (SEQ ID NO:55) | | 1 |
| ML-IAP$_{99}$ | LTAEVPPEL | (SEQ ID NO:100) | | 0.9 |
| ML-IAP$_{83}$ | GMGSEELRL | (SEQ ID NO:84) | | 30 |
| ML-IAP$_{200}$ | ELPTPRREV | (SEQ ID NO:200) | | Not binding |

Very Preferred ML-IAP Polypeptide Fragments

In one aspect the present invention relates to a polypeptide fragment capable of raising a specific T-cell response, said fragment comprising a peptide consisting of at least 9 consecutive amino acid residues of ML-IAP (SEQ ID NO:1), wherein said peptide is selected from the group consisting rlqeertck (SEQ ID NO:245), qilgqlrpl (SEQ ID NO:55), ltaevppel (SEQ ID NO:100), gmgseelrl (SEQ ID NO:84), elptprrev (SEQ ID NO:200), rlqeertckv (SEQ ID NO:297), qlcpicrapv (SEQ ID NO:298), llrskgrdfv (SEQ ID NO:300), vleppgardv (SEQ ID NO:301) and pltaevppel (SEQ ID NO:302); and wherein said polypeptide fragment comprises at the most 100 amino acids.

Preferably the polypeptide fragment comprises at the most 90, more preferably at the most 80, even more preferably at the most 70, yet more preferably at the most 60 even more preferably at the most 70, yet more preferably at the most 60, even more preferably at the most 50, yet more preferably at the most 40, even more preferably at the most 30, yet more preferably at the most 20, even more preferably at the most 18, yet more preferably at the most 16, even more preferably at the most 15, yet more preferably at the most 14, even more preferably at the most 13, yet more preferably at the most 12, such as at the most 11, for example at the most 10, such as at the most 9 amino acids.

It is preferred that the polypeptide fragment comprises at least 9, such as at least 10, for example at least 11, such as at least 12, for example at least 13, such as at least 14, for example at least 15 consecutive amino acids of ML-IAP (SEQ ID:1). Thus the polypeptide fragment may consist of 9, such as 10, for example 11, such as 12, for example 13, such as 14, for example 15 consecutive amino acids of SEQ ID:1, comprising (SEQ ID NO:245), (SEQ ID NO:55), (SEQ ID NO:100), (SEQ ID NO:84), (SEQ ID NO:200), (SEQ ID NO:297), (SEQ ID NO:298), (SEQ ID NO:300), (SEQ ID NO:301) or (SEQ ID NO:302).

Functional Characterisation of Preferred ML-IAP Fragments

Very preferred fragments of ML-IAP according to the present invention are fragments of ML-IAP capable of eliciting a specific T-cell response, which may be either a cytotoxic T-cell response or a helper T-cell response, but which preferably is a cytotoxic T-cell response. Several different state-of-the-art methods may be used to identify peptide fragments capable of eliciting a specific T-cell response. However, it is difficult to predict whether a given peptide will be capable of eliciting a specific T-cell response. Even though computer models may predict functional epitopes, experimental evidence is usually required in order to verify whether a predicted epitope indeed is a functional epitope. Even fragments that associate with MHC molecules with high affinity will not necessarily give rise to a T-cell response as determined by for example ELISPOT assay (see herein below) or in an individual.

Hence, in one embodiment of the present invention it is preferred that the ML-IAP fragments are capable of association with an MHC molecule, even more preferred that the fragment is capable of association with a class I MHC molecule. Preferred MHC class I molecules are frequently occurring MHC class I molecules, for example the MHC class I molecules described herein below. Association between ML-IAP and an MHC molecule may for example be determined using the assembly assay described herein below.

Preferred, ML-IAP fragment according to the invention may be characterised by having a $C_{50}$ value, measured as the concentration (μM) of the polypeptide fragment required for half maximal binding to an MHC molecule, preferably to an MHC class I molecule, in the range of from 500 to 1000, such as in the range of 200 to 500, for example in the range of 100 to 200, such as in the range of 50 to 100, for example in range of 25 to 50, such as in the range of 10 to 25, for example in range of 5 to 10 such as in the range of 1 to 5, for example in range of 0.1 to 1 such as in the range of 0.05 to 0.1, for example less than 0.05. Said MHC class I molecule may be any MHC class I molecule, for example an HLA-A molecule, such as HLA-A2. Preferred MHC class I molecules are frequently occurring MHC class I molecules, for example the MHC class I molecules described herein below.

More preferred fragments of ML-IAP includes fragments of ML-IAP wherein the $C_{50}$ value is less than 1000 µM, even more preferably less than 200 µM, yet more preferably less than 100 µM, yet even more preferably less than 75 µM, even more preferably less than 50 µM, yet more preferably less than 40 µM, even more preferably less than 31 µM, yet more preferably less than 25 µM, even more preferably less than 10 µM, yet more preferably less than 5 µM, even more preferably less than 1 µM, yet more preferably less than 0.5 µM, even more preferably less than 0.2 µM, yet more preferably less than 0.1 µM, even more preferably less than 0.05 µM, wherein the $C_{50}$ value is the concentration of the peptide required for half maximal binding to an MHC molecule, preferably to an MHC class I molecule. Said MHC class I molecule may be any MHC class I molecule, such as an HLA-A molecule, for example HLA-A2. Preferred MHC class I molecules are frequently occurring MHC class I molecules, for example the MHC class I molecules described herein below.

It is preferred that the $C_{50}$ value is determined according to the assembly assay described herein below.

Accordingly, in one embodiment of the present invention preferred fragments of ML-IAP may be selected from the group consisting of ML-IAP$_{280}$, ML-IAP$_{83}$, ML-IAP$_{154}$, ML-IAP$_{245}$, ML-IAP$_{54}$ and ML-IAP$_{99}$. More preferred fragments of ML-IAP may be selected from the group consisting of ML-IAP$_{245}$, ML-IAP$_{54}$ and ML-IAP$_{99}$.

Assembly Assay

Assembly assays for binding of the synthetic peptides to class I MHC molecules metabolically labeled with [$^{35}$S]-methionine can be carried out as described below. It will be appreciated by the person skilled in the art that the protocol may be adopted for any peptide and any class I MHC molecule. Previously, it has been demonstrated that the peptide concentration resulting in half-maximal binding in an assembly assay for peptide binding to class I MHC is a good approximation of Ka[15].

Briefly, TAP deficient cells were metabolically labeled with [$^{35}$S]-methionine (Amersham, Freiburg, Germany). The cells were lyzed in 0.5 ml lysis buffer (150 mM NaCl, 50 mM TrisHCl, 0.5% NP-40 (Fluka, Buchs, Switzerland), 5 mM EDTA, pH 7.5) with 0.5% Mega-9 (Sigma, St. Louis, USA) in the presence of protease inhibitors (2 mM PMSF, 5 mM iodoacetamide, 2 µg/ml pepstatin, 2 µg/ml leupeptin) with or without synthetic peptide (for a list of positive control peptides, see Table 2).

After 20 min of incubation, the cell nuclei were removed by centrifugation (5 min, 10,000 g) and 50 µl (10% v/v) freshly washed *Staphylococcus aureus* organisms (Pansorbin, Calbiochem, Nottingham, UK). The next day Pansorbin was removed by centrifugation (12 min, 16,000 g) and the appropriate monoclonal antibody was added at a final concentration of 10 µg/ml, incubated for 90 min, followed by addition of protein A-Sepharose (75 µl, 10% v/v) and incubation for 1 h. The beads were washed 4 times and stored at −20° C. until analysis by electrophoresis.

For peptide binding to HLA-B*2705 and H-2K$^k$ a modified assembly assay was used as described previously by us[39]. When transfected into T2 cells B*2705 and K$^k$ are unusually stable in the absence of added peptide. To circumvent this, a mild heating step was introduced in order to preferentially destabilize MHC molecules which remain empty after peptide incubation. Briefly, the cell lysates are incubated with peptide for 2 h at 4° C., allowing the binding of peptide to empty class I molecules. Next, the cell lysates were heated (60° C. for 5 min for T2-B*2705 or 55° C. for 2 min for T2-K$^k$). Pansorbin was then added to the samples as in the conventional assembly assay.

Electrophoresis

In the case of an assembly assay with the HLA class I-specific conformation-dependent monoclonal antibody W6/32, samples were eluted in reducing buffer (9.5 M urea, 2% NP-40, 5% 2-mercaptoethanol, 2% Ampholines, pH range 3.5-9.5 (Pharmacia Biotech, Uppsala, Sweden)) and focused for 16 h at 880 V on 5.5% polyacrylamide isoelectric focusing (IEF) gels[20,39].

Samples from assembly assays with allele-specific antibodies were eluted by boiling (5 min) in SDS reducing buffer (50 mM TrisHCl pH 6.8, 2% SDS, 5% 2-mercaptoethanol, 10% glycerol, 2.5% bromophenol blue) and electrophorezed on 12% SDS-PAGE gels (1 h at 200 V). All gels were fixed in 10% acetic acid with 5% methanol and dried onto 3 MM paper (Whatman, Maidstone, UK). MHC heavy chain bands were quantified using the Imagequant Phosphorimager program (Molecular Dynamics, Sunnyvale, Calif., USA). The intensity of the band is directly related to the amount of peptide-bound class I MHC complex recovered during the assay. $C_{50}$ value (µM) as the concentration of the peptide required for half maximal binding to MHC may thus be determined. The binding affinities of the analysed peptides are determined according to their efficiency of stabilising the HLA class I molecules. The binding affinity is represented as the peptide concentration required to reach half-maximal stabilisation of appropriate HLA-molecule. Previous analyses have shown that the C50 values measured in this assay fits well with the dissociation constant (Kd) of the complex[31].

Epitope prediction may be performed using a suitable algorithm, preferably an algorithmus based on the book "MHC Ligands and Peptide Motifs" by H. G. Rammensee, J. Bachmanna and S. Stevanovic. However, such epitope prediction is not reliable, and thus it is preferred within the present invention that ML-IAP fragments are identified using ELISPOT assays and/or binding assays as described herein elsewhere. One method of predicting epitopes is using the SYFPEITHI epitope prediction algorithm. Further explanations on the algorithm can be found in H G Rammensee, J Bachmann, N P N Emmerich, O A Bachor and S Stevanovic (1999) SYFPEITHI: database for MHC ligands and peptide motifs. Immunogenetics 50: 213-219. SYFPEITHI database can be found on the internet site: http://syfpeithi.bmiheidelberg.com/scripts/MHCServer.dll/home.htm The algorithm calculates the predicted ligation strength to a defined HLA type for a sequence of aminoacids. Preferred ML-IAP has a predicted ligation strength to a given HLA molecule as calculated using said algorithm of at least 10, preferably at least 12, more preferably at least 15, even more preferably at least 16, such as at least 18, for example at least 20.

However, even more preferred fragments according to the present invention are ML-IAP fragments capable of raising a specific T-cell response as determined by an ELISPOT assay, for example the ELISPOT assay described herein below.

Some fragments of ML-IAP although not binding MHC with high affinity still may give rise to a T-cell response as determined by ELISPOT. Other fragments of ML-IAP may be capable of binding MHC with high affinity and gives rise to a T-cell response as determined by ELISPOT. Both kinds of fragments are preferred fragments according to the invention.

Hence, preferred fragments according to the present invention are ML-IAP fragments capable of raising a specific T-cell response as measured by an ELISPOT assay, wherein more than 50 fragment specific spots per $10^8$ cells, more preferably per $10^7$ cells, even more preferably per $10^6$ cells, yet more preferably per $10^5$ cells, for example per $10^4$ cells are measured Hence, in one embodiment of the present invention preferred ML-IAP fragments may be selected from the group consisting of ML-IAP$_{245}$ (SEQ ID NO:297), ML-IAP$_{280}$ (SEQ ID NO:298) and ML-IAP$_{230}$, (SEQ ID NO:301). Further preferred fragments peptides comprising or even more preferably consisting of SEQ ID NO:245.

ELISPOT

Antigen Stimulation of PBL

Peripheral blood was obtained from melanoma patients before vaccination and subsequent to a series of vaccinations. In order to identify peptide-specific T-cell precursors, peripheral blood lymphocytes (PBL) were used directly in the ELISPOT (designated direct ELISPOT). However, to extend the sensitivity of the ELISPOT assay, PBL were stimulated once in vitro prior to analysis[17,18]. At day 0, PBL or crushed lymph nodes were thawed and plated in 2 ml/well at a concentration of $2\times10^6$ cells in 24-well plates (Nunc, Denmark) in X-vivo medium (Bio Whittaker, Walkersville, Md.), 5% heat-inactivated human serum, and 2 mM of L-glutamine in the presence of 10 μM of peptide. Two days later 20 IU/ml recombinant interleukin-2 (IL-2) (Chiron, Ratingen, Germany) was added to the cultures. The cultured cells were tested for reactivity in the ELISPOT on day 8.

ELISPOT Assay

The ELISPOT assay used to quantify peptide epitope specific interferon-7 releasing effector cells was adapted from Lalvani et al.[37], and Scheibenbogen et al.[38]. Briefly, nitrocellulose bottomed 96-well plates (MultiScreen MAIP N45, Millipore) were coated overnight at 4° C. with 7.5 μg/ml of anti-IFN-γ antibody (1-D1K, Mabtech, Sweden) in 75 μl sterile PBS. Subsequently, the wells were washed six times with PBS, and non-specific binding were blocked by X-vivo medium for 2 hours at 37° C. Freshly isolated PBL or cells, which had been stimulated once in vitro, were added in duplicates at different cell concentrations (from $10^6$ to $10^5$ cells per well for non-stimulated PBL, and from $3\times10^5$-$3\times10^4$ cells per well for PBL which had been stimulated once in vitro), in 100 μl X-vivo medium. Peptides were then added to each well to a final concentration of 2 μM and incubated overnight at 37° C.

The following day, media was discarded and the wells were washed (six times) with PBS containing 0.05% Tween (PBS/Tw) before the addition of biotinylated secondary antibody (7-B6-1-Biotin, Mabtech) at 0.5 μg/ml in 75 μl PBS containing 1% BSA and 0.02% NaN$_3$ (PBS/BSA). The plates were incubated at room temperature for 2 hours. The wells were washed (six times) with PBS/Tw. Then 75 μl of Avidin-enzyme conjugate (AP-Avidin, Calbiochem) diluted 1:2000 in PBS/BSA were added to each well and incubated for 1 hour. The enzyme substrate NBT/BCIP was prepared freshly according to the manufacturers' instructions (Gibco, code 18280-016) and 75 μl were added to each well and incubated for 5-10 min. The reaction was terminated by washing with tap-water upon the emergence of dark purple spots. The spots were then counted using the AlphaImager System (Alpha Innotech, San Leandro, Calif., USA) and the peptide specific CTL frequency could be calculated as the number of spot-forming cells.

It is preferred that the ELISPOT assay is performed using PBL derived from an individual that has not previously been immunised with ML-IAP or a fragment thereof. More preferably, said individual has not been subjected to any kind of immune therapy against a neoplastic disease. Hence it is for example preferred that the individual has not been immunised with tumour cells previously. PBL from individuals that have been subjected to immune therapy, in particular immune therapy comprising ML-IAP, may give a positive result against a given peptide in an ELISPOT assay, even though PBL from a naive person would not have given a positive result.

In yet another embodiment of the present invention, preferred ML-IAP fragments are fragments capable of activating T-cell growth in vitro. In particular, preferred ML-IAP fragments induce expansion of antigen-specific CTL using DC loaded with said fragments. A method of expanding antigen-specific CTLs is described herein below. Accordingly, very preferred ML-IAP fragments includes fragments, wherein more than $10^5$ antigen specific CTLs, more preferably $10^6$, even more preferably $10^7$ antigen specific CTLs may be harvested after 4 stimulation cycles starting with $10^4$ PBMC as described herein below.

Expansion of Antigen-Specific CTL Using Antigen-Loaded DC

The generation of dendritic cells (DC) was performed as described[40]. PBMC were plated in 85 mm dishes (either bacteriological, Primaria or Tissue culture dishes, Falcon, Cat. No. 1005, 3038 or 3003; Becton Dickinson, Hershey, USA) at a density of $50\times10^6$ cells per dish in 10 ml of complete culture medium and incubated at 37° C. and 5% CO$_2$ for 1 h. After a microscopic control of adherence, the non-adherent fraction was removed and 10 ml of fresh, warm complete medium (RPMI 1640 (Prod. Nr. 12-167, Bio Whittaker, Walkersville, USA) supplemented with gentamicin (Refobacin 10, Merck, Darmstadt, Germany) at 20 μg/ml final concentration, glutamine at 2 mM final concentration (Prod. Nr. 17-605, Bio Whittaker) and 1% heat inactivated (56° for 30 min) human plasma) were added (day 0). The non-adherent fractions were centrifuged and plated once more in new 85 mm tissue-culture-dishes for readherence. The non-adherent fraction from these replate' dishes was discarded after 1 h adherence. All adherent fractions were cultured until day 1, then culture medium was taken off carefully so that loosely adherent cells were not removed, and new culture medium containing GM-CSF (800 U/ml final concentration) and IL-4 (1000 U/ml final concentration) was added. Cytokines were added again on day 3 in 3 ml fresh medium (containing 8000 U GM-CSF and 10,000 U IL-4) per dish. On day 5 all non-adherent cells were harvested, counted and replated in fresh complete medium (containing cytokines in the same dosage as described above) in 6 well plates at a density of $5\times10^5$ cells/well in 3 ml medium. On day 6 750 μl monocyte conditioned medium (MCM) were added) to induce maturation of DC, and on day 7 or 8 cells were harvested.

All DC preparations were highly enriched in mature DC with >90% showing a characteristic phenotype by flow cytometry (HLA-DR+++, CD86+++, CD40+, CD25', CD14−). More than 80% of the cells expressed the CD83 antigen as marker for mature DC.

MCM was prepared in the following way: Ig coated bacteriological plates (85 mm, Falcon 1005) were prepared immediately prior to use. As immunoglobulin we used Sandoglobin™ (Novartis). Coating was performed with 10 ml of diluted (with PBS without calcium or magnesium, Bio Whittaker) immunoglobulin (10 µg/ml) for 10 min at room temperature. After the coating procedure plates were rinsed twice with PBS without calcium or magnesium (Bio Whittaker). 50×10⁶ PBMC were plated on these dishes in complete medium without cytokines and incubated at 37° C., 5% $CO_2$ for 20 h. Then the monocyte conditioned medium was harvested, centrifuged at 1360 g for 10 min (22° C.), sterile filtered (0.22 µm filters, Millipore, Molsheim, France) and frozen down in aliquots at −20° C. 5×10⁶ cells/well DC were pulsed with 50 µg/ml HLA-restricted peptide for example an ML-IAP fragment for 2 h at 37° C. peptide. About 10⁴ PBMC/well and 5×10³ antigen-loaded autologous DC/well were co-cultured in a 96-well round-bottom plates in 200 µl MCM medium/well supplemented with 5% autologous plasma. On day 7, PBMC were restimulated either with antigen-loaded DC. After a total of 4 to 5 stimulation cycles CD8⁺ T lymphocytes were enriched from PBMC by depletion of CD4⁺, CD11b⁺, CD16⁺, CD19⁺, CD36⁺ and CD56⁺ cells with magnetic cell sorting using a midiMACS device (Miltenyi Biotec GmbH, Bergisch Gladbach, Germany). The resulting population consisted of >90% CD8+ T cells.

For expansion of specific CTLs, such as tumour specific CTLs, the CD8-enriched T cells were transferred to 25-cm² flasks coated with anti-CD3/anti-CD28 mAbs, as described previously 41. Briefly, 25-cm² flasks (Falcon, Heidelberg, Germany) were coated with anti-human CD3 mAb (OKT3, Ortho Pharmaceutical Corp., Raritan, N.J.) and anti-human CD28 mAb (L293, Becton Dickinson) at a concentration of 1 µg/ml in PBS/100 mM HEPES buffer (pH 9). After incubation overnight at 4° C., coated flasks were washed twice with PBS. CD8+ T cells were placed on the precoated and washed flasks at 5×10⁵ cells/ml in 10 ml MCM medium supplemented with 10% human AB serum (PAA Laboratories GmbH, Coelbe, Germany) and 100 IU IL-2/ml (EuroCetus, Amsterdam, Netherlands). Cells were restimulated with anti-CD3/anti-CD28 mAbs once a week, culture medium and IL-2 (100 IU/ml) was changed twice a week. Part of CD8-purified CTL were expanded by weekly restimulation with antigen-loaded DC or PBL.

In some embodiments of the present invention preferred ML-IAP fragments are fragments capable of being presented by a specific MHC molecule. Hence, very preferred ML-IAP fragments may be fragments capable of raising a specific T-cell response in an individual with a specific tissue type. Preferred MHC molecules according to the invention are listed herein below.

In particular the peptides listed herein below, are preferred peptides for use in an individual of the specified tissue type:

```
HLA-A1
MLIAP85     G S E E L R L A S       (SEQ ID NO:86)

MLIAP50     H V D G Q I L G Q       (SEQ ID NO:51)

MLIAP120    D K V R C F F C Y       (SEQ ID NO:121)

MLIAP213    A Q E P G G V S P       (SEQ ID NO:213)

MLIAP230    V L E P P G A R D       (SEQ ID NO:230)

MLIAP86     S E E L R L A S F Y     (SEQ ID NO:303)
```

```
                    -continued
MLIAP166    V Q E T H S Q L L G     (SEQ ID NO:304)

MLIAP100    T A E V P P E L L A     (SEQ ID NO:305)

MLIAP119    Q D K V R C F F C Y     (SEQ ID NO:306)

HLA-A3
MLIAP245    R L Q E E R T C K       (SEQ ID NO:245)

MLIAP218    G V S P A E A Q R       (SEQ ID NO:218)

MLIAP288    P V R S R V R T F       (SEQ ID NO:288)

MLIAP106    E L L A A A G F F       (SEQ ID NO:107)

MLIAP242    Q L R R L Q E E R       (SEQ ID NO:242)

MLIAP253    K V C L D R A V S       (SEQ ID NO:253)

MLIAP253    K V C L D R A V S I     (SEQ ID NO:307)

MLIAP244    R R L Q E E R T C K     (SEQ ID NO:308)

MLIAP153    F L L R S K G R D F     (SEQ ID NO:309)

MLIAP106    E L L A A A G F F H     (SEQ ID NO:310)

MLIAP255    C L D R A V S I V F     (SEQ ID NO:311)

MLIAP55     I L G Q L R P L T E     (SEQ ID NO:312)

MLIAP126    F C Y G G L Q S W K     (SEQ ID NO:313)

HLA-A24
MLIAP80     A F P G M G S E E L     (SEQ ID NO:314)

MLIAP147    W F P S C Q F L L       (SEQ ID NO:147)

HLA-B7/HLA-B35
MLIAP193    V P A S G Y P E L       (SEQ ID NO:193)

MLIAP81     F P G M G S E E L       (SEQ ID NO:82)

MLIAP2      G P K D S A K C L       (SEQ ID NO:3)

MLIAP31     G P R S L G S P V       (SEQ ID NO:32)

MLIAP276    A P G L Q L C P I       (SEQ ID NO:276)

MLIAP31     G P R S L G S P V L     (SEQ ID NO:315)

MLIAP190    A P S V P A S G Y       (SEQ ID NO:190)

HLA-B27
MLIAP32     P R S L G S P V L       (SEQ ID NO:33)

MLIAP236    A R D V E A Q L R       (SEQ ID NO:236)

MLIAP289    V R S R V R T F L       (SEQ ID NO:289)

MLIAP237    R D V E A Q L R R       (SEQ ID NO:237)

MLIAP76     S R G P A F P G M       (SEQ ID NO:77)

MLIAP122    V R C F F C Y G G L     (SEQ ID NO:316)

MLIAP244    R R L Q E E R T C K     (SEQ ID NO:317)

MLIAP249    E R T C K V C L D R     (SEQ ID NO:318)
```

A very preferred peptide is MLIAP245 R L Q E E R T C K (SEQ ID NO:245).

In another embodiment of the present invention preferred fragments of ML-IAP are fragments which may give rise to a specific T-cell response without leading to anti-body production. Epitopes only leading to a T-cell response, but not an IgG response have been described in the prior art 29,30.

Methods of Identifying Fragments

In one aspect the present invention also relates to methods of selecting a peptide comprising a fragment of ML-IAP for use in a vaccine composition comprising the steps of
i) Providing an individual who has not been subjected to immune therapy
ii) Providing fragments of ML-IAP
iii) Testing specific T-cell responses against fragments of ML-IAP in said individual
iv) Selecting fragments of ML-IAP wherein said T-cell response corresponds to or is better than a predetermined selection criterium.

The T-cell response may be tested according to any suitable method, it is however preferred that testing said T-cell response comprises an ELISPOT assay. The ELISPOT assay is preferably the assay described herein above.

Preferably, fragments giving rise to more than 50 peptide specific spots per $10^6$ cells in an ELISPOT assay, preferably the ELISPOT assay described herein above, are selected.

Vaccine Compositions and Uses Thereof

The present invention in one embodiment is directed to an immunogenic composition such as a vaccine composition capable of raising e.g. a specific T-cell response. The vaccine composition comprises ML-IAP (SEQ ID NO:1), and/or one or more fragments thereof. Preferably, the vaccine compositions comprise isolated ML-IAP and/or one or more isolated fragments thereof. The terms "ML-IAP peptide" as used herein below refers to ML-IAP (SEQ ID NO:1) and fragments thereof as described herein elsewhere. Any of the ML-IAP fragments described herein above may be comprised within said vaccine, in particular the preferred ML-IAP fragments described above may be comprised within a vaccine.

Hence, the vaccine compositions according to the invention may comprise more than one different ML-IAP fragment, such as 2, for example 3, such as 4, for example 5, such as 6, for example 7, such as 8, for example 9, such as 10, such as a number of fragments in the range of from 5 to 10, for example in the range of from 10 to 15, such as in the range of from 15 to 20, for example in the range of from 20 to 30, such as in the range of from 30 to 40, for example in the range of from 40 to 60, such as in the range of from 60 to 100, for example in the range of from 100 to 200 different ML-IAP fragments.

The vaccine composition may comprise at least 1, more preferably at least 2, even more preferably at least 3, yet more preferably at least 4, for example at least 5, such as at least 6, for example 7 different ML-IAP fragments each capable of associating with a different HLA molecule selected from the group consisting of HLA-A2, HLA-A1, HLA-A3, HLA-A24, HLA-B7, HLA-B27 and HLA-B44.

In one embodiment of the present invention the different ML-IAP fragments are selected so that one vaccine composition comprises fragments capable of associating with different MHC molecules, such as different MHC class I molecule, i.e. the ML-IAP fragments are restricted to specific HLA's. Preferably, one vaccine composition comprises fragments capable of associating with the most frequently occurring MHC class I molecules. Preferred MHC class I molecules are listed herein elsewhere. Hence preferred vaccine compositions comprises different fragments capable of associating with at least 2 preferred, more preferably at least 3 preferred, even more preferably at least 4 preferred MHC class I molecules.

In another embodiment of the invention, the vaccine composition comprises one or more fragments capable of associating to an MHC class I molecule and one or more fragments capable of associating with an MHC class II molecule. Peptide vaccine preparations capable of being used in accordance with the present invention may thus comprise a class I-restricted ML-IAP peptide and/or a class II-restricted ML-IAP peptide and/or fusion peptides comprising both peptides. Hence, such a vaccine composition is preferably capable of raising a specific cytotoxic T-cells response and/or a specific helper T-cell response.

The vaccine composition can further comprise an adjuvant and/or a carrier. Examples of useful adjuvants and carriers are given herein below. Thus ML-IAP, or the fragment thereof, present in the composition can be associated with a carrier such as e.g. a protein or an antigen-presenting cell such as e.g. a dendritic cell (DC) capable of presenting ML-IAP or a fragment thereof to a T-cell.

Adjuvants are any substance whose admixture into the vaccine composition increases or otherwise modifies the immune response to ML-IAP or a fragment. Carriers are scaffold structures, for example a polypeptide or a polysaccharide, to which ML-IAP, or the fragment thereof is capable of being associated.

Adjuvants could for example be selected from the group consisting of: $AlK(SO_4)_2$, $AlNa(SO_4)_2$, $AlNH_4(SO_4)$, silica, alum, $Al(OH)_3$, $Ca_3(PO_4)_2$, kaolin, carbon, aluminum hydroxide, muramyl dipeptides, N-acetyl-muramyl-L-threonyl-D-isoglutamine (thr-DMP), N-acetyl-nornuramyl-L-alanyl-D-isoglutamine (CGP 11687, also referred to as nor-MDP), N-acetylmuramyul-L-alanyl-D-isoglutaminyl-L-alanine-2-(1'2'-dipalmitoyl-sn-glycero-3-hydroxphosphoryloxy)-ethylamine (CGP 19835A, also referred to as MTP-PE), RIBI (MPL+TDM+CWS) in a 2% squalene/Tween-80® emulsion, lipopolysaccharides and its various derivatives, including lipid A, Freund's Complete Adjuvant (FCA), Freund's Incomplete Adjuvants, Merck Adjuvant 65, polynucleotides (for example, poly IC and poly AU acids), wax D from Mycobacterium, tuberculosis, substances found in *Corynebacterium parvum, Bordetella pertussis*, and members of the genus *Brucella*, liposomes or other lipid emulsions, Titermax, ISCOMS, QuilA, ALUN (see U.S. Pat. Nos. 5,876,724 and 5,554,372), Lipid A derivatives, choleratoxin derivatives, HSP derivatives, LPS derivatives, synthetic peptide matrixes or GMDP, Interleukin 1, Interleukin 2, Montanide ISA-51 and QS-21. Preferred adjuvants to be used with the invention include Montanide ISA-51 and QS-21.

Montanide ISA-51 (Seppic, Inc.) is a mineral oil-based adjuvant analogous to incomplete Freund's adjuvant, which must be administered as an emulsion. QS-21 (Antigenics; Aquila Biopharmaceuticals, Framingham, Mass.) is a highly purified, water-soluble saponin that handles as an aqueous solution. QS-21 and Montanide ISA-51 adjuvants can be provided in sterile, single-use vials.

Additional preferred adjuvants capable of being used in vaccine compositions comprising ML-IAP, and/or one or more fragments thereof, are e.g. any substance which promote an immune responses. Frequently, the adjuvant of choice is Freund's complete or incomplete adjuvant, or killed *B. pertussis* organisms, used e.g. in combination with alum precipitated antigen. A general discussion of adjuvants is provided in Goding, Monoclonal Antibodies: Principles & Practice (2nd edition, 1986) at pages 61-63. Goding notes, however, that when the antigen of interest is of low molecular weight, or is poorly immunogenic, coupling to an immunogenic carrier is recommended. Examples of such carrier molecules include keyhole limpet haemocyanin, bovine serum albumin, ovalbumin and fowl immunoglobulin. Various saponin extracts have also been suggested to be useful as adjuvants in immunogenic compositions. Recently, it has been proposed to use granulocyte-macrophage colony stimulating factor (GM-CSF), a well known cytokine, as an adjuvant (WO 97/28816).

Desirable functionalities of adjuvants capable of being used in accordance with the present invention are listed in the below table.

ments of ML-IAP described herein, in particular preferred fragments of ML-IAP described herein.

DC-Based Vaccines and Therapeutic Procedures Using DC

Cancer patients such as e.g. stage IV metastatic melanoma patients with progressive disease were entered into a DC-based vaccination trial e.g. after having failed to respond to

TABLE 1

Modes of adjuvant action

| Action | Adjuvant type | Benefit |
| --- | --- | --- |
| 1. Immunomodulation | Generally small molecules or proteins which modify the cytokine network | Upregulation of immune response. Selection of Th1 or Th2 |
| 2. Presentation | Generally amphipathic molecules or complexes which interact with immunogen in its native conformation | Increased neutralizing antibody response. Greater duration of response |
| 3. CTL induction | Particles which can bind or enclose immunogen and which can fuse with or disrupt cell membranes | Cytosolic processing of protein yielding correct class 1 restricted peptides |
|  | w/o emulsions for direct attachment of peptide to cell surface MHC-1 | Simple process if promiscuous peptide(s) known |
| 4. Targeting | Particulate adjuvants which bind immunogen. Adjuvants which saturate Kupffer cells | Efficient use of adjuvant and immunogen |
|  | Carbohydrate adjuvants which target lectin receptors on macrophages and DCs | As above. May also determine type of response if targeting selective |
| 5. Depot Generation | w/o emulsion for short term | Efficiency |
|  | Microspheres or nanospheres for long term | Potential for single-dose vaccine |

Source: Cox, J.C., and Coulter, A.R. (1997). Vaccine 15, 248-56.

A vaccine composition according to the present invention may comprise more than one different adjuvant. Furthermore, the invention encompasses a therapeutic composition further comprising any adjuvant substance including any of the above or combinations thereof. It is also contemplated that ML-IAP, or one or more fragments thereof, and the adjuvant can be administered separately in any appropriate sequence.

A carrier may be present independently of an adjuvant. The function of a carrier can for example be to increase the molecular weight of in particular ML-IAP fragments in order to increase their activity or immunogenicity, to confer stability, to increase the biological activity, or to increase serum half-life. Furthermore, a carrier may aid presenting ML-IAP, or the fragments thereof to T-cells. The carrier may be any suitable carrier known to the person skilled in the art, for example a protein or an antigen presenting cell. A carrier protein could be but is not limited to keyhole limpet hemocyanin, serum proteins such as transferrin, bovine serum albumin, human serum albumin, thyroglobulin or ovalbumin, immunoglobulins, or hormones, such as insulin or palmitic acid. For immunization of humans, the carrier must be a physiologically acceptable carrier acceptable to humans and safe. However, tetanus toxoid and/or diphtheria toxoid are suitable carriers in one embodiment of the invention. Alternatively, the carrier may be dextrans for example sepharose.

In one embodiment, the vaccine composition may comprise dendritic cells. The dendritic cells (DC) may be prepared and used in therapeutic procedure according to any suitable protocol, for example as described herein below. It will be appreciated by the person skilled in the art that the protocol may be adopted to use with patients with different HLA type and different diseases. The peptide in the below procedure can be any fragment of ML-IAP such as e.g. fragchemotherapy. All patients provided informed consent to participate in the experimental vaccination and to donate blood for immunological monitoring.

Serological HLA typing revealed that the patients were HLA-A2. Dendritic cells (DC) were pulsed with 50 µg/ml HLA-restricted peptide for 1 h at 37° C. peptide and $5\times10^6$ cells were administered subcutaneously at day 1 and 14, subsequently every 4 weeks, additional leukopheresis after 5 vaccinations.

All vaccine preparations were highly enriched in mature DC with >90% showing a characteristic phenotype by flow cytometry (HLA-DR+++, CD86+++, CD40+, CD25+, CD14−). More than 80% of the cells expressed the CD83 antigen as marker for mature DC. The peptide used in the vaccination trial were synthesized at a GMP quality by Clinalfa (purity>98%).

The generation of DC for clinical use and quality control was performed as described[40]. PBMC were plated in 85 mm dishes (either bacteriological, Primaria or Tissue culture dishes, Falcon, Cat. No. 1005, 3038 or 3003; Becton Dickinson, Hershey, USA) at a density of $50\times10^6$ cells per dish in 10 ml of complete culture medium and incubated at 37° C. and 5% CO2 for 1 h. After a microscopic control of adherence, the non-adherent fraction was removed and 10 ml of fresh, warm complete medium (RPMI 1640 (Prod. Nr. 12-167, Bio Whittaker, Walkersville, USA) supplemented with gentamicin (Refobacin 10, Merck, Darmstadt, Germany) at 20 µg/ml final concentration, glutamine at 2 mM final concentration (Prod. Nr. 17-605, Bio Whittaker) and 1% heat inactivated (56° for 30 min) human plasma) were added (day 0).

The non-adherent fractions were centrifuged and plated once more in new 85 mm tissue-culture-dishes for readherence. The non-adherent fraction from these 'replate' dishes was discarded after 1 h adherence. All adherent fractions were cultured until day 1, then culture medium was taken off carefully so that loosely adherent cells were not removed, and new culture medium containing GM-CSF (800 U/ml final concentration) and IL-4 (1000 U/ml final concentration) was added. Cytokines were added again on day 3 in 3 ml fresh medium (containing 8000 U GM-CSF and 10,000 U IL-4) per dish. On day 5 all non-adherent cells were harvested, counted and replated in fresh complete medium (containing cytokines in the same dosage as described above) in 6 well plates at a density of $5\times10^5$ cells/well in 3 ml medium. On day 6 750 µl monocyte conditioned medium (MCM) were added) to induce maturation of DC, and on day 7 or 8 cells were harvested.

MCM (monocyte conditioned medium) was prepared in the following way: Ig coated bacteriological plates (85 mm, Falcon 1005) were prepared immediately prior to use. As immunoglobin we used Sandoglobin™ (Novartis). Coating was performed with 10 ml of diluted (with PBS without calcium or magnesium, Bio Whittaker) immunoglobulin (10 µg/ml) for 10 min at room temperature. After the coating procedure plates were rinsed twice with PBS without calcium or magnesium (Bio Whittaker). $50\times10^6$ PBMC were plated on these dishes in complete medium without cytokines and incubated at 37° C., 5% $CO_2$ for 20 h. Then the monocyte conditioned medium was harvested, centrifuged at 1360 g for 10 min (22° C.), sterile filtered (0.22 µm filters, Millipore, Molsheim, France) and frozen down in aliquots at $-20°$ C.[18,38,42]

Peptide Vaccines

Vaccine compositions may be prepared and administered using any conventional protocol known by a person skilled in the art. Below a non-limiting example of preparation of a vaccine composition according to the invention is given as well as a non-limiting example of administration of such as a vaccine. It will be appreciated by the person skilled in the art that the protocol may be easily adapted to any of the vaccine compositions described herein.

ML-IAP peptides can e.g. be synthesized e.g. at the UVA Biomolecular Core Facility with a free amide $NH_2$ terminus and free acid COOH terminus. Each was provided as a lyophilized peptide, which was then reconstituted in sterile water and diluted with Lactated Ringer's solution (LR, Baxter Healthcare, Deerfield, Ill.) as a buffer for a final concentration of 67-80% Lactated Ringer's in water. These solutions were then sterile-filtered, placed in borosilicate glass vials, and submitted to a series of quality assurance studies including confirmation of identity, sterility, general safety, and purity, in accordance with FDA guidelines, as defined in IND 6453. Tests of peptide stability demonstrated no decrease in purity or in the peptide concentration, when these peptide solutions were stored at −20° C. for 3 years.

In practical circumstances, patients will receive a vaccine comprising about 100 µg of a class I HLA-restricted ML-IAP peptide with or without a class II HLA-restricted ML-IAP helper peptide. The patients are vaccinated with e.g. about 100 µg of the class I HLA peptide in adjuvant alone, or were vaccinated with e.g. about 100 µg of the HLA class I-restricted peptide plus 190 µg of the class II-restricted helper peptide. The higher dose of the helper peptide was calculated to provide equimolar quantities of the helper and cytotoxic epitopes. Additionally, patients can be vaccinated with a longer peptide comprising the amino acid sequences of both peptides.

The above peptides, in 1-ml aqueous solution, can be administered either as a solution/suspension with about 100 µg of QS-21, or as an emulsion with about 1 ml of Montanide ISA-51 adjuvant.

Patients are immunized e.g. at day 0 and months 1, 2, 3, 6, 9, and 12, with the peptides plus adjuvant, for a total of seven immunizations. With rare exceptions, the vaccinations are administered to the same arm with each vaccine. The peptides were administered s.c.[43,44]

MHC Molecules

In one embodiment of the present invention preferred ML-IAP fragments are fragments capable of associating with an MHC molecule. Because different MHC molecules have different affinities for a given peptide, different ML-IAP fragments may be preferred with different embodiments of the invention. The invention also relates to compositions comprising different ML-IAP fragments, which preferably have affinity for different MHC molecules.

Preferred MHC molecules according to the present invention are MHC class I molecules and MHC class II molecules, more preferably MHC class I molecules. Preferred MHC class I molecules are the most commonly occurring MHC class I molecules. In one embodiment of the present invention the preferred MHC class I molecules may be selected from the group consisting of HLA-A2, HLA-A1, HLA-A3, HLA-A24, HLA-B7, HLA-B27 and HLA-B44.

Preferred compositions according to the present invention comprises at least 1, more preferably at least 2, even more preferably at least 3, yet more preferably at least 4, for example at least 5, such as at least 6, for example 7 different ML-IAP fragments each capable of associating with a different HLA molecule selected from the group consisting of HLA-A2, HLA-A1, HLA-A3, HLA-A24, HLA-B7, HLA-B27 and HLA-B44.

By way of example, a preferred composition may comprise one ML-IAP peptide capable of associating with HLA-A2 and an ML-IAP peptide capable of associating with HLA-A1 and an ML-IAP peptide capable of associating with HLA-A3 and an ML-IAP peptide capable of associating with HLA-A24.

Ex Vivo Methods for Obtaining and Cultivating T-Cells

In one embodiment, the present invention relates to a method for activating and expanding T-cells specific for ML-IAP or fragments thereof as well as to T-cells obtained by such methods. Preferably, the methods related to cytotoxic T-cells specific for ML-IAP fragments. The methods preferably comprise the steps of co-cultivating T-cells and ML-IAP, or at least one fragment thereof, thereby activating the T-cells, and optionally isolating activated ML-IAP specific T-cells or ML-IAP fragment specific T-cells.

Co-cultivating T-cells and ML-IAP or fragments thereof may be done by any conventional method. For example methods involving antigen presenting cells, such as dendritic cells (DC) may be used. The method may thus comprise generating and loading monocyte-derived dendritic cells (DC) with ML-IAP fragment(s) and co-cultivating said DC and peripheral blood monocytes (PBMC) comprising T-cells or T-cells purified from PBMC. Optionally the ML-IAP specific T-cells may then be isolated. Preferably, the ML-IAP specific T-cells are cytotoxic T-cells.

One preferred method for generating and loading of monocyte-derived DC and for co-cultivating DC and peripheral blood monocytes (PBMC) is described herein above in the section "Expansion of antigen specific CTL using antigen-loaded CD":

However, different kinds of antigen presenting cells (APC) may be used with the invention.

In one example, there is provided a method for in vitro immunization with Drosophila Cells as APCs. Hence, the method may comprise generating Drosphila melanogaster cells expressing one or more different HLA molecules, loading said Drosophila melanogaster cells with ML-IAP fragment(s) and co-cultivating said Drosophila cells with peripheral blood monocytes (PBMC) comprising T-cells or T-cells purified from PBMC. Thereby, ML-IAP specific T-cells may be generated. Preferably, said T-cells are cytotoxic T-cells. Optionally, T-cells may subsequently be isolated. One advantage of using Drosophila melanogaster cells is that they are non-viable at 37° C.

Drosophila melanogaster cells were used as APCs[45,46]. These cells are efficient vehicles for the presentation of peptides in the context of HLA class I, especially for de novo immunization of CD8+ CTL. The Schneider S2 Drosophila cell line (American Type Culture Collection CRL 10974, Rockville, Md.) was transduced with HLA-A2.1, CD80 (B7-1) and CD54 (intracellular adhesion molecule-1) with a pRmHa-3 plasmid vector. Drosophila cells were grown in Schneider's medium ($10^6$ cells/mL) with 10% fetal bovine serum and $CuSO_4$ at 27° C., the optimal temperature for these insect cells. They were harvested, washed, and resuspended in X-press medium (Bio Whittaker, Walkersville, Md.) containing 100 pg/mL of the HLA-restricted peptide epitope.

CD8+ T cells were obtained from peripheral blood mononuclear cells (PBMCs) by positive selection with a novel anti-CD8 monoclonal antibody (mAb) captured with a sheep anti-mouse magnetic bead (Dynal, Lake Success, N.Y.) 47.

After incubation at 27° C. with the HLA-restricted peptide epitope for 3 hours, the Drosophila cells were incubated with the CD8+ T cells at 37° C. at a ratio of 1:10 in RPMI 1640 medium containing 10% autologous serum. Two days later, 20 IU of IL-2 and 30 IU of IL-7 were added to the growth medium. Incubation was continued for 1 week, after when the Drosophila cells were replaced with autologous irradiated PBMCs (30 Gy) and the HLA-restricted peptide. This was repeated for one additional round of stimulation, after when the CD8+ T cells were tested for cytotoxicity by a 4-hour[51] Cr release assay. The final preparation contained at least 92% CD8+ T cells, with 4% or less CD16+ (natural killer) cells and 4% or less CD4+ T cells.

The present invention also relates to methods of treating a clinical condition in an individual in need thereof, comprising (re)infusing ML-IAP specific T-cells into. Furthermore the invention relates to use of ML-IAP specific T-cells for the preparation of a medicament for treatment of a clinical condition in an individual in need thereof and to medicaments for treating a clinical condition comprising ML-IAP specific T-cells as active ingredient.

Methods of (re)infusing T-cells to an individual are known in the art. One example of a suitable method is outlined herein below.

In yet another embodiment there is provided a method for obtaining T cells from an individual and reinfusing the T cells after immunization ex vivo. Leukapheresis was performed to obtain approximately $1 \times 10^{10}$ peripheral-blood mononuclear cells (PBMCs). After three rounds (3 weeks) of in vitro immunization, formal mycologic and bacteriologic testing was performed to verify sterility before the cells were administered.

No Drosophila cells remained in the CTL preparation after the immunization procedure. Drosophila cells are viable at 27° C. but are nonviable at 37° C. Furthermore, two rounds of immunization with changes of medium each time were performed subsequent to the initial immunization with the fly cells. Finally, the polymerase chain reaction was used in order to detect residual Drosophila DNA in the final preparation of CTL before reinfusion. Drosophila DNA was uniformly absent by this sensitive method.

For infusion into the patient, the CTLs were resuspended in 200 mL of 0.9% saline with 5% human serum albumin in a transfer pack (Baxter [McGaw Park, IL] catalog no. 4R-2014 plastic blood cell infusion bag) and were administered intravenously over a period of 1 hour on the stem-cell transplantation unit. Experienced nurses took vital signs every 15 minutes and monitored the patients for signs of toxicity or immediate hypersensitivity reactions.

Combination Therapy

The present invention furthermore relates to pharmaceutical compositions and kit-of-parts for use in combination therapy.

Combination therapy as used herein denotes treatment an individual in need thereof with more than one different method. Hence combination therapy may in one aspect involve administration of a pharmaceutical composition or a kit of parts comprising a vaccine composition as described herein above and an anti-cancer medicament. Anti-cancer medicaments may be any of the medicaments described herein below, for example a chemotherapeutic agent or a immunotherapeutic agent.

In particular combination therapy may involve administration to an individual of a chemotherapeutic agent and/or an immunotherapeutic agent in combination with one or more of i) ML-IAP, or a fragment thereof, ii) an antigen presenting cell presenting ML-IAP, and iii) an activated, ML-IAP peptide specific T-cell. However, combination therapy may also involve radiation therapy, gene therapy and/or surgery.

Combination therapy thus may include administration, simultaneously, or sequentially in any order, of e.g.:
i) ML-IAP and/or fragments thereof+at least one chemotherapeutic agent
ii) ML-IAP and/or fragments thereof+at least one immunotherapeutic agent
iii) Antigen presenting cell presenting ML-IAP and/or fragments thereof+at least one chemotherapeutic agent
iv) Antigen presenting cell presenting ML-IAP and/or fragments thereof+at least one immunotherapeutic agent
v) Activated T-cells+at least one chemotherapeutic agent
vi) Activated T-cells+at least one immunotherapeutic agent Further combinations include i) and ii); iii) and iv); v) and vi); i) and iii); i) and iv), i) and v); i) and vi); ii) and iii); ii) and iv); ii) and v); ii) and vi); iii) and v); iii) and vi); iv) and v); iv) and vi); i) and iv) and any of v) and vi).

The chemotherapeutic agent can be e.g. methotrexate, vincristine, adriamycin, cisplatin, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MM1270, BAY 12-9566, RAS farnesyl transferase inhibitor, farnesyl transferase inhibitor, MMP, MTA/LY231514, LY264618/Lometexol, Glamolec, CI-994, TNP-470, Hycamtin/Topotecan, PKC412, Valspodar/PSC833, Novantrone/Mitroxantrone, Metaret/Suramin, Batimastat, E7070, BCH-4556, CS-682, 9-AC, AG3340, AG3433, Incel/VX-710, VX-853, ZD0101, ISI641, ODN 698, TA 2516/Marmistat, BB2516/Marmistat, CDP 845, D2163, PD183805, DX8951f, Lemonal DP 2202, FK 317, Picibanil/OK-432, AD 32/Valrubicin, Metastron/strontium derivative, Temodal/Temozolomide, Evacet/liposomal doxorubicin, Yewtaxan/Paclitaxel, Taxol/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT(Tegafur/Uracil), Ergamisol/Levamisole, Eniluracil/776C85/5FU enhancer, Campto/Levamisole, Camptosar/Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/Epirubicin, DepoCyt, ZD1839, LU 79553/Bis-Naphthalimide, LU 103793/Dolastain, Caetyx/liposomal doxorubicin, Gemzar/Gemcitabine, ZD 0473/Anormed, YM 116, Iodine seeds, CDK4 and CDK2 inhibitors, PARP inhibitors, D4809/Dexifosamide, Ifes/Mesnex/Ifosamide, Vumon/Teniposide, Paraplatin/Carboplatin, Plantinol/cisplatin, Vepeside/Etoposide, ZD 9331, Taxotere/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bisguanylhydrazone; MGBG), Pentostatin (2'deoxycoformycin), Semustine (methyl-CCNU), Teniposide (VM-26) and Vindesine sulfate. Furthermore, the chemotherapeutic agent may be any of the chemotherapeutic agents mentioned in table 3 of U.S. Pat. No. 6,482,843 column 13 to 18.

The immunotherapeutic agent can be e.g. Ributaxin, Herceptin™ (Trastuzumab, a humanized monoclonal antibody that acts on the HER2/neu [erbB2] receptor), Quadramet™ (Samarium-153-ethylene diamine tetramethylene phosphonate), Panorex, IDEC-Y2B8, BEC2, C225, Oncolym, SMART MI 95, ATRAGEN, Ovarex, Bexxar, LDP-03, ior t6, MDX-210, MDX-11, MDX-22, OV103, 3622W94, anti-VEGF, Zenapax, MDX-220, MDX-447, MELIMMUNE-2, MELIMMUNE-1, CEACIDE, Pre-target, NovoMAb-G2, TNT, Gliomab-H, GNI-250, EMD-72000, LymphoCide™ (Epratuzumab, a humanized monoclonal antibody that acts on CD22), CMA 676, Monopharm-C, 4B5, ior egf.r3, ior c5, BABS, anti-FLK-2, MDX-260, ANA Ab, SMART 1D10 Ab, SMART ABL 364 Ab and ImmuRAIT-CEA. Furthermore the immunotherapeutic agent may be any cytokine or interferon.

The therapeutic compositions or vaccine compositions of the invention can also be used in combination with other anti-cancer strategies, and such combination therapies are effective in inhibiting and/or eliminating tumor growth and metastasis. The methods of the present invention can advantageously be used with other treatment modalities, including, without limitation, radiation, surgery, gene therapy and chemotherapy.

"Combination therapy" can include the introduction of heterologous nucleic acids into suitable cells, generally known as gene therapy. For example gene therapy may involve introduction of tumour suppressor genes or apoptosis promoting genes into tumour cells. Alternatively, nucleic acid sequences inhibiting expression of oncogenes or apoptosis inhibiting genes may be introduced to tumour cells. Furthermore, genes that encode enzymes capable of conferring to tumor cells sensitivity to chemotherapeutic agents may be introduced. Accordingly, the present invention in one embodiment provides a method comprising the step of treating cancer by introducing a gene vector, encoding a protein capable of enzymatically converting a prodrug, i.e., a non-toxic compound, into a toxic compound. In the method of the present invention, the therapeutic nucleic acid sequence is a nucleic acid coding for a product, wherein the product causes cell death by itself or in the presence of other drugs. A representative example of such a therapeutic nucleic acid is one, which codes for thymidine kinase of herpes simplex virus. Additional examples are thymidine kinase of varicella zoster virus and the bacterial gene cytosine deaminase, which can convert 5-fluorocytosine to the highly toxic compound 5-fluorouracil.

Clinical Indications Capable of being Treated with the Present Invention

The vaccine compositions or the therapeutic/pharmaceutical compositions disclosed herein may be used to treat a number of different clinical conditions. Furthermore, the present invention relates to methods of treatment of said clinical conditions in an individual in need thereof, methods of diagnosing said clinical conditions and use of ML-IAP or fragments thereof for preparation of a medicament for treatment of a clinical condition in an individual in need thereof as well as to medicaments for treating a clinical condition comprising ML-IAP or fragments thereof as active ingredient.

In a preferred embodiment of the invention, the clinical condition is a cancer. The term "cancer" as used herein is meant to encompass any cancer, neoplastic and preneoplastic disease. Said cancer may for example be selected from the group consisting of colon carcinoma, breast cancer, pancreatic cancer, ovarian cancer, prostate cancer, fibrosarcoma, myxosarcoma, liposarcoma, chondrosarcoma, osteogenic sarcoma, chordoma, angiosarcoma, endotheliosarcoma, lymphangiosarcoma, lymphangioendothelia sarcoma, synovioma, mesothelioma, Ewing's sarcoma, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystandeocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioblastomas, neuronomas, craniopharingiomas, schwannomas, glioma, astrocytoma, medulloblastoma, craniopharyngioma, ependymoma, pinealoma, hemangioblastoma, acoustic neuroama, oligodendroglioma, meningioma, melanoma, neuroblastoma, retinoblastoma, leukemias and lymphomas, acute lymphocytic leukemia and acute myelocytic polycythemia vera, multiple myeloma, Waldenstrom's macroglobulinemia, and heavy chain disease, acute nonlymphocytic leukemias, chronic lymphocytic leukemia, chronic myelogenous leukemia, Hodgkin's Disease, non-Hodgkin's lymphomas, rectum cancer, urinary cancers, uterine cancers, oral cancers, skin cancers, stomach cancer, brain tumors, liver cancer, laryngeal cancer, esophageal cancer, mammary tumors, childhood-null acute lymphoid leukemia (ALL), thymic ALL, B-cell ALL, acute myeloid leukemia, myelomonocytoid leukemia, acute megakaryocytoid leukemia, Burkitt's lymphoma, acute myeloid leukemia, chronic myeloid leukemia, and T cell leukemia, small and large non-small cell lung carcinoma, acute granulocytic leukemia, germ cell tumors, endometrial cancer, gastric cancer, cancer of the head and neck, chronic lymphoid leukemia, hairy cell leukemia and thyroid cancer.

In preferred embodiments of the invention the clinical condition is a type of cancer frequently expressing ML-IAP or a type of cancer wherein cell lines derived from said type of cancer frequently expresses ML-IAP. For example cell lines derived from malignant melanomas frequently express ML-IAP[14,26], whereas cell lines derived from breast cancer often do not express ML-IAP[26]. It is very much preferred however, that the clinical condition is a cancer expressing ML-IAP.

In a preferred embodiment, the clinical condition is malignant melanoma.

In another embodiment of the invention the clinical condition is an auto-immune disease.

Autoimmune diseases may be loosely grouped into those primarily restricted to specific organs or tissues and those that affect the entire body. Examples of organ-specific disorders (with the organ affected) include multiple sclerosis (myelin coating on nerve processes), type I diabetes mellitus (pancreas), Hashimotos thyroiditis (thyroid gland), pernicious anemia (stomach), Addison's disease (adrenal glands), myasthenia gravis (acetylcholine receptors at neuromuscular junction), rheumatoid arthritis (joint lining), uveitis (eye), psoriasis (skin), Guillain-Barre Syndrome (nerve cells) and Grave's disease (thyroid). Systemic autoimmune diseases include systemic lupus erythematosus and dermatomyositis.

Other examples of hypersensitivity disorders include asthma, eczema, atopical dermatitis, contact dermatitis, other eczematous dermatitides, seborrheic dermatitis, rhinitis, Lichen planus, Pemplugus, bullous Pemphigoid, Epidermolysis bullosa, uritcaris, angioedemas, vasculitides, erythemas, cutaneous eosinophilias, Alopecia greata, atherosclerosis, primary biliary cirrhosis and nephrotic syndrome. Related diseases include intestinal inflammations, such as Coeliac disease, proctitis, eosinophilia gastroenteritis, mastocytosis, inflammatory bowel disease, Chrohn's disease and ulcerative colitis, as well as food-related allergies.

The individual in need of treatment may be any individual, preferably a human being. Peptides will in general have different affinities to different HLA molecules. Hence, in the embodiments of the present invention wherein the vaccine composition or the pharmaceutical composition comprises ML-IAP peptides, it is preferred that a vaccine composition or a pharmaceutical composition to be administered to a given individual will comprise at least one peptide capable of associating with HLA molecules of that particular individual.

The methods according to the present invention allows vaccination even of immunologically naive individuals, because the vaccine compositions according to the invention preferably comprises immunologically dominant ML-IAP fragments. Hence, in one embodiment of the present invention the individual in need of treatment has not previously been subjected to immune therapy against a neoplastic disease. In particular it is preferred that the individual has not previously been subjected to an immune therapy that comprised immunisation with a component comprising ML-IAP or a fragment thereof. Hence, for example it is preferred that said individual has not been immunised with a tumour cell expressing ML-IAP.

Pharmaceutical Compositions

Accordingly, the invention in preferred embodiments relates to pharmaceutical compositions which comprise ML-IAP (SEQ ID NO:1), and/or variants or fragments of these molecules as defined herein above for the treatment of pathological disorders related to or mediated by the ML-IAP.

Pharmaceutically and/or veterinary useful therapeutic compositions according to the invention can be formulated according to known methods such as by the admixture of one or more pharmaceutically or veterinary acceptable excipients or carriers. Examples of such excipients, carriers and methods of formulation may be found e.g. in Remington's Pharmaceutical Sciences (Maack Publishing Co, Easton, Pa.). To form a pharmaceutically or veterinary acceptable composition suitable for effective administration, such compositions will contain an effective amount of a polypeptide, nucleic acid, antibody or compound modulator.

Therapeutic or diagnostic compositions of the invention are administered to an individual (mammal-human or animal) or used in amounts sufficient to treat or diagnose apoptosis-related disorders. The effective amount may vary according to a variety of factors such as the individual's condition, weight, sex and age. Other factors include the mode of administration.

The term functional derivative includes a molecule that contains additional chemical moieties which are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Pharmaceutical and veterinary compositions suitable for use in the present invention include compositions wherein the active ingredients are contained in an effective amount to achieve the intended purpose. The determination of an effective dose is well within the capability of those skilled in the art. The therapeutically effective dose can be estimated initially either in cell culture assays, e.g., of neoplastic cells, or in animal models, usually mice, rabbits, dogs, or pigs. The animal model is also used to achieve a desirable concentration range and route of administration. Such information can then be used to determine useful doses and routes for administration in humans and other animals. A therapeutically effective dose refers to that amount of compound, peptide, antibody or nucleic acid which ameliorate or prevent a dysfunctional apoptotic condition. The exact dosage is chosen by the individual physician in view of the patient to be treated.

Compounds identified according to the methods disclosed herein as well as, therapeutic antibodies, therapeutic nucleic acids and peptides contemplated herein may be used alone at appropriate dosages defined by routine testing in order to obtain optimal modulation of livin activity. In addition, co-administration or sequential administration of these and other agents may be desirable.

The pharmaceutical or veterinary compositions may be provided to the individual by a variety of routes such as subcutaneous, topical, oral and intramuscular. Administration of pharmaceutical compositions is accomplished orally or parenterally. Methods of parenteral delivery include topical, intra-arterial (directly to the tissue), intramuscular, subcutaneous, intramedullary, intrathecal, intraventricular, intravenous, intraperitoneal, or intranasal administration. The present invention also has the objective of providing suitable topical, oral, systemic and parenteral pharmaceutical formulations for use in the novel methods of treatment of the present invention. The compositions containing compounds identified according to this invention as the active ingredient for use in the modulation of a protein which mediates apoptosis can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound, nucleic acid, or peptide desired can be employed as an apoptosis modulating agent.

The daily dosage of the products may be varied over a wide range from 0.001 to 1,000 mg per adult human/per day. For oral administration, the compositions are preferably provided in the form of scored or unscored tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0001 mg/kg to about 100 mg/kg of body weight per day. The range is more particularly from about 0.001 mg/kg to 10 mg/kg of body weight per day. Even more particularly, the range varies from about 0.05 to about 1 mg/kg.

Of course the dosage level will vary depending upon the potency of the particular compound. Certain compounds will be more potent than others. In addition, the dosage level will vary depending upon the bioavailability of the compound. The more bioavailable and potent the compound, the less compound will need to be administered through any delivery route, including but not limited to oral delivery.

The dosages of livin modulators are adjusted when combined to achieve desired effects. On the other hand, dosages of these various agents may be independently optimized and combined to achieve a synergistic result wherein the pathology is reduced more than it would be if either agent were used alone. Those skilled in the art will employ different formulations for nucleotides than for proteins or their inhibitors.

There is also provided combination therapies comprising the step of administering the vaccine compositions according to the invention in combination with a chemotherapeutic agent and/or an immunotherapeutic agent and/or a cancer vaccine.

Variants and Functional Equivalents of ML-IAP

The present invention is also directed to variants and functional equivalents of the above-listed fragments of ML-IAP.

The affinity of various HLA molecules towards a given peptide depends on the sequence of said peptide. In table 2 herein below the amino acids in a given position within a peptide that results in the highest affinity of said peptide to a given HLA molecule are described.

Hence, preferred variants of ML-IAP peptides with high affinity to a particular HLA molecule are listed herein below with an indication of the position in which a substitution preferably has occurred for each of the above-listed fragments. The preferred amino acid residue in the respective position of the variant is indicted in the table.

Accordingly, by way of example, a preferred ML-IAP peptide variant capable of binding to HLA-B54 has a proline at the second position.

TABLE 2

Primary anchor residue motifs employed

| HLA allele | Position 1 | Position 2 | Position 3 | Position 5 | Position 6 | Position 7 | C-terminal |
|---|---|---|---|---|---|---|---|
| HLA-A1 | | T,S | D,E | | | L | Y |
| HLA-A2 | | L,M | | | V | | L,V |
| HLA-A3 | | L,V,M | F,Y | | | | K,Y,F |
| HLA-A11 | | V,I,F,Y | M,L,F,Y,I | | | | K,R |
| HLA-A23 | | I,Y | | | | | W,I |
| HLA-A24 | | Y | | I,V | F | | I,L,F |
| HLA-A25 | | M,A,T | I | | | | W |
| HLA-A26 | E,D | V,T,I,L,F | | | I,L,V | | Y,F |
| HLA-A28 | E,D | V,A,L | | | | | A,R |
| HLA-A29 | | E | | | | | Y,L |
| HLA-A30 | | Y,L,F,V | | | | | Y |
| HLA-A31 | | | L,M,F,Y | | | | R |
| HLA-A32 | | I,L | | | | | W |
| HLA-A33 | | Y,I,L,V | | | | | R |
| HLA-A34 | | V,L | | | | | R |
| HLA-A66 | E,D | T,V | | | | | R,K |
| HLA-A68 | E,D | T,V | | | | | R,K |
| HLA-A69 | V,T,A | | | | | | V,L |
| HLA-A74 | | T | | | | | V,L |
| HLA-B5 | | A,P | F,Y | | | | I,L |
| HLA-B7 | | P | | | | | L,F |
| HLA-B8 | | | K | K,R | | | L |
| HLA-B14 | | R,K | | | | | L,V |
| HLA-B15 (B62) | | Q,L,K,P,H,V,I,M,S,T | | | | | F,Y,W |
| HLA-B17 | | | | | | | L,V |
| HLA-B27 | | R | | | | | Y,K,F,L |
| HLA-B35 | | P | | | | | I,L,M,Y |
| HLA-B37 | | D,E | | | | | I,L,M |
| HLA-B38 | | H | D,E | | | | F,L |
| HLA-B39 | | R,H | | | | | L,F |
| HLA-B40 (B60,61) | | E | F,I,V | | | | L,V,A,W,M,T,R |
| HLA-B42 | | L,P | | | | | Y,L |
| HLA-B44 | | E | | | | | F,Y,W |
| HLA-B46 | | M,I,L,V | | | | | Y,F |
| HLA-B48 | | Q,K | | | | | L |

TABLE 2-continued

Primary anchor residue motifs employed

| HLA allele | Position 1 | Position 2 | Position 3 | Position 5 | Position 6 | Position 7 | C-terminal |
|---|---|---|---|---|---|---|---|
| HLA-B51 | | A,P,G | | | | | F,Y,I,V |
| HLA-B52 | | Q | F,Y | | | | I,V |
| HLA-B53 | | P | | | | | W,F,L |
| HLA-B54 | | P | | | | | |
| HLA-B55 | | P | | | | | A,V |
| HLA-B56 | | P | | | | | A,V |
| HLA-B57 | | A,T,S | | | | | F,W,Y |
| HLA-B58 | | A,T,S | | | | | F,W,Y |
| HLA-B67 | | P | | | | | L |
| HLA-B73 | | R | | | | | P |
| HLA-Cw1 | | A,L | | | | | L |
| HLA-Cw2 | | A,L | | | | | F,Y |
| HLA-Cw3 | | A,L | | | | | L,M |
| HLA-Cw4 | | Y,P,F | | | | | L,M,F,Y |
| HLA-Cw6 | | | | | | | L,I,V,Y |
| HLA-Cw6 | | Y | | | | | L,Y,F |
| HLA-Cw8 | | Y | | | | | L,I, |
| HLA-Cw16 | | A,L | | | | | L,V |

Functional equivalents and variants are used interchangeably herein. When being polypeptides, variants are determined on the basis of their degree of identity or their degree of homology with any predetermined sequence of consecutive amino acid sequences of a fragment of ML-IAP, such as e.g. SEQ ID NO:2-SEQ ID NO:290.

One therefore initially define a sequence of consecutive ML-IAP amino acid residues and then define variants and functional equivalents in relation thereto.

Accordingly, variants preferably have at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with the predetermined ML-IAP sequence of consecutive amino acid residues.

Sequence identity is determined in one embodiment by utilising fragments of peptides comprising at least 9 contiguous amino acids and having an amino acid sequence which is at least 80%, such as 85%, for example 90%, such as 95%, for example 99% identical to the amino acid sequence of any of SEQ ID NO:2-SEQ ID NO:290, respectively, wherein the percent identity is determined with the algorithm GAP, BESTFIT, or FASTA in the Wisconsin Genetics Software Package Release 7.0, using default gap weights.

The following terms are used to describe the sequence relationships between two or more polynucleotides: "predetermined sequence", "comparison window", "sequence identity", "percentage of sequence identity", and "substantial identity". A "predetermined sequence" is a defined sequence used as a basis for a sequence comparison; a predetermined sequence may be a subset of a larger sequence.

Optimal alignment of sequences for aligning a comparison window may be conducted by the local homology algorithm of Smith and Waterman (1981) Adv. Appl. Math. 2: 482, by the homology alignment algorithm of Needleman and Wunsch (1970) J. Mol. Biol. 48: 443, by the search for similarity method of Pearson and Lipman (1988) Proc. Natl. Acad. Sci. (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two amino acid sequences are identical over the window of comparison.

The term "percentage of sequence identity" is calculated by comparing two optimally aligned sequences over the window of comparison, determining the number of positions at which identical amino acid residues occur in both sequences to yield the number of matched positions, dividing the number of matched positions by the total number of positions in the window of comparison (i.e., the window size), and multiplying the result by 100 to yield the percentage of sequence identity.

As applied to polypeptides, a degree of identity of amino acid sequences is a function of the number of identical amino acids at positions shared by the amino acid sequences. A degree of homology or similarity of amino acid sequences is a function of the number of amino acids, i.e. structurally related, at positions shared by the amino acid sequences.

The term "substantial identity" means that two peptide sequences, when optimally aligned, such as by the programs GAP or BESTFIT using default gap weights, share at least 75 percent sequence identity, such as at least 80 percent sequence identity, for example at least 85 percent sequence identity, such as e.g. at least 90 percent sequence identity, for example at least 95 percent sequence identity, such as at least 98 percent sequence identity, or even at least 99 percent sequence identity, compared to a predetermined sequence over a comparison window of at least 9 amino acid residues, such as 10 amino acid residues, for example 11 amino acid residues, such as 12 amino acid residues, for example 13 amino acid residues, such as 14 amino acid residues, for example 15 amino acid residues, such as 20 amino acid residues, for example 30 amino acid residues, such as 40 amino acid residues, for example 50 amino acid residues, such as 60 amino acid residues, for example 70 amino acid residues, such as 80 amino acid residues, for example 90 amino acid residues, such as 100 amino acid residues, for example 110 amino acid residues, such as 120 amino acid residues, for example 130 amino acid residues, such as 140 amino acid residues, for example 150 amino acid residues, such as 175 amino acid residues, for example 200 amino acid residues, such as 225 amino acid residues, for example 250 amino acid residues, such as 275 amino acid residues, for example 297 amino acid residues. Preferably, residue positions which are not identical differ by conservative amino acid substitutions.

An "unrelated" or "non-homologous" sequence shares less than 40% identity, though preferably less than 25% identity, with an ML-IAP amino acid sequence of the present invention.

Conservative amino acid substitutions refer in one embodiment to the interchangeability of residues having similar side chains. For example, a group of amino acids having aliphatic side chains is glycine, alanine, valine, leucine, and isoleucine; a group of amino acids having aliphatic-hydroxyl side chains is serine and threonine, a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

Additionally, variants are also determined based on a predetermined number of conservative amino acid substitutions as defined herein below. Conservative amino acid substitution as used herein relates to the substitution of one amino acid (within a predetermined group of amino acids) for another amino acid (within the same group), wherein the amino acids exhibit similar or substantially similar characteristics.

Within the meaning of the term "conservative amino acid substitution" as applied herein, one amino acid may be substituted for another within the groups of amino acids indicated herein below:

Amino acids having polar side chains (Asp, Glu, Lys, Arg, His, Asn, Gln, Ser, Thr, Tyr, and Cys)

Amino acids having non-polar side chains (Gly, Ala, Val, Leu, Ile, Phe, Trp, Pro, and Met)

Amino acids having aliphatic side chains (Gly, Ala Val, Leu, Ile)

Amino acids having cyclic side chains (Phe, Tyr, Trp, His, Pro)

Amino acids having aromatic side chains (Phe, Tyr, Trp)

Amino acids having acidic side chains (Asp, Glu)

Amino acids having basic side chains (Lys, Arg, His)

Amino acids having amide side chains (Asn, Gln)

Amino acids having hydroxy side chains (Ser, Thr)

Amino acids having sulphor-containing side chains (Cys, Met),

Neutral, weakly hydrophobic amino acids (Pro, Ala, Gly, Ser, Thr)

Hydrophilic, acidic amino acids (Gln, Asn, Glu, Asp), and

Hydrophobic amino acids (Leu, Ile, Val)

Accordingly, a variant or a fragment thereof according to the invention may comprise at least one substitution, such as a plurality of substitutions introduced independently of one another. It is clear from the above outline that the same variant or fragment thereof may comprise more than one conservative amino acid substitution from more than one group of conservative amino acids as defined herein above.

The addition or deletion of at least one amino acid may be an addition or deletion of from preferably 2 to 250 amino acids, such as from 10 to 20 amino acids, for example from 20 to 30 amino acids, such as from 40 to 50 amino acids. However, additions or deletions of more than 50 amino acids, such as additions from 50 to 100 amino acids, addition of 100 to 150 amino acids, addition of 150-250 amino acids, are also comprised within the present invention. The deletion and/or the addition may—independently of one another—be a deletion and/or an addition within a sequence and/or at the end of a sequence.

The polypeptide fragments according to the present invention, including any functional equivalents thereof, may in one embodiment comprise a sequence of consecutive ML-IAP amino acid residues of less than 250 amino acid residues, such as less than 240 amino acid residues, for example less than 225 amino acid residues, such as less than 200 amino acid residues, for example less than 180 amino acid residues, such as less than 160 amino acid residues, for example less than 150 amino acid residues, such as less than 140 amino acid residues, for example less than 130 amino acid residues, such as less than 120 amino acid residues, for example less than 110 amino acid residues, such as less than 100 amino acid residues, for example less than 90 amino acid residues, such as less than 85 amino acid residues, for example less than 80 amino acid residues, such as less than 75 amino acid residues, for example less than 70 amino acid residues, such as less than 65 amino acid residues, for example less than 60 amino acid residues, such as less than 55 amino acid residues, for example less than 50 amino acid residues, such as less than 45 amino acid residues, for example less than 30 amino acid residues, such as less than 25 amino acid residues, for example less than 20 amino acid residues, such as less than 15 amino acid residues, for example 14 consecutive amino acid residues, such as 13 consecutive amino acid residues, for example 12 consecutive amino acid residues, such as 11 consecutive amino acid residues, for example 10 consecutive amino acid residues, such as 9 consecutive amino acid residues of ML-IAP (SEQ ID NO:1).

"Functional equivalency" as used in the present invention is according to one preferred embodiment established by means of reference to the corresponding functionality of a predetermined fragment of the sequence.

Functional equivalency can be established by e.g. similar binding affinities to HLA class I molecules, or similar potency demonstrated by ELISPOT assays.

Functional equivalents or variants of a ML-IAP fragment as described herein will be understood to exhibit amino acid sequences gradually differing from preferred, predetermined sequences, as the number and scope of insertions, deletions and substitutions including conservative substitutions, increases. This difference is measured as a reduction in homology between a preferred, predetermined sequence and the ML-IAP variant fragment or ML-IAP functional equivalent.

All ML-IAP fragments comprising or consisting of consecutive ML-IAP amino acid residues as well as variants and functional equivalents thereof are included within the scope of this invention, regardless of the degree of homology they show to a predetermined sequence. The reason for this is that some regions of the ML-IAP fragments are most likely readily mutatable, or capable of being completely deleted, without any significant effect on e.g. the binding activity of the resulting fragment.

A functional variant obtained by substitution may well exhibit some form or degree of native binding activity, and yet be less homologous, if residues containing functionally similar amino acid side chains are substituted. Functionally similar in this respect refers to dominant characteristics of the side chains such as hydrophobic, basic, neutral or acidic, or the presence or absence of steric bulk. Accordingly, in one embodiment of the invention, the degree of identity is not a principal measure of a fragment being a variant or functional equivalent of a preferred predetermined fragment according to the present invention.

The homology between amino acid sequences may be calculated using well known algorithms such as any one of BLOSUM 30, BLOSUM 40, BLOSUM 45, BLOSUM 50, BLOSUM 55, BLOSUM 60, BLOSUM 62, BLOSUM 65, BLOSUM 70, BLOSUM 75, BLOSUM 80, BLOSUM 85, and BLOSUM 90.

Fragments sharing homology with fragments comprising or consisting of consecutive ML-IAP amino acid residues are to be considered as falling within the scope of the present invention when they are preferably at least about 90 percent homologous, for example at least 92 percent homologous, such as at least 94 percent homologous, for example at least 95 percent homologous, such as at least 96 percent homologous, for example at least 97 percent homologous, such as at least 98 percent homologous, for example at least 99 percent homologous with a predetermined ML-IAP fragment. According to one embodiment of the invention the homology percentages indicated above are identity percentages.

Additional factors that may be taken into consideration when determining functional equivalence according to the meaning used herein are i) the ability of antisera to detect a ML-IAP fragment according to the present invention, or ii) the ability of a functionally equivalent ML-IAP fragment to compete with a predetermined ML-IAP fragment in an assay. One method for determining a sequence of immunogenically active amino acids within a known amino acid sequence has been described by Geysen in U.S. Pat. No. 5,595,915 and is incorporated herein by reference.

A further suitably adaptable method for determining structure and function relationships of peptide fragments is described by U.S. Pat. No. 6,013,478, which is herein incorporated by reference. Also, methods of assaying the binding of an amino acid sequence to a receptor moiety such as e.g. a T-cell receptor are known to the skilled artisan.

In addition to conservative substitutions introduced into any position of a preferred ML-IAP fragments, it may also be desirable to introduce non-conservative substitutions in any one or more positions of such a fragment. A non-conservative substitution leading to the formation of a functionally equivalent fragment would for example i) differ substantially in polarity, for example a residue with a non-polar side chain (Ala, Leu, Pro, Trp, Val, Ile, Leu, Phe or Met) substituted for a residue with a polar side chain such as Gly, Ser, Thr, Cys, Tyr, Asn, or Gln or a charged amino acid such as Asp, Glu, Arg, or Lys, or substituting a charged or a polar residue for a non-polar one; and/or ii) differ substantially in its effect on polypeptide backbone orientation such as substitution of or for Pro or Gly by another residue; and/or iii) differ substantially in electric charge, for example substitution of a negatively charged residue such as Glu or Asp for a positively charged residue such as Lys, His or Arg (and vice versa); and/or iv) differ substantially in steric bulk, for example substitution of a bulky residue such as His, Trp, Phe or Tyr for one having a minor side chain, e.g. Ala, Gly or Ser (and vice versa).

Variants obtained by substitution of amino acids may in one preferred embodiment be made based upon the hydrophobicity and hydrophilicity values and the relative similarity of the amino acid side-chain substituents, including charge, size, and the like. Exemplary amino acid substitutions which take various of the foregoing characteristics into consideration are well known to those of skill in the art and include: arginine and lysine; glutamate and aspartate; serine and threonine; glutamine and asparagine; and valine, leucine and isoleucine.

In a further embodiment the present invention relates to functional variants comprising substituted amino acids having hydrophilic values or hydropathic indices that are within +/−4.9, for example within +/−4.7, such as within +/−4.5, for example within +/−4.3, such as within +/−4.1, for example within +/−3.9, such as within +/−3.7, for example within +/−3.5, such as within +/−3.3, for example within +/−3.1, such as within +/−2.9, for example within +/−2.7, such as within +/−2.5, for example within +/−2.3, such as within +/−2.1, for example within +/−2.0, such as within +/−1.8, for example within +/−1.6, such as within +/−1.5, for example within +/−1.4, such as within +/−1.3 for example within +/−1.2, such as within +/−1.1, for example within +/−1.0, such as within +/−0.9, for example within +/−0.8, such as within +/−0.7, for example within +/−0.6, such as within +/−0.5, for example within +/−0.4, such as within +/−0.3, for example within +/−0.25, such as within +/−0.2 of the value of the amino acid it has substituted.

The importance of the hydrophilic and hydropathic amino acid indices in conferring interactive biologic function on a protein is well understood in the art (Kyte & Doolittle, 1982 and Hopp, U.S. Pat. No. 4,554,101, each incorporated herein by reference).

The amino acid hydropathic index values as used herein are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5) (Kyte & Doolittle, 1982).

The amino acid hydrophilicity values are: arginine (+3.0); lysine (+3.0); aspartate (+3.0.+−.0.1); glutamate (+3.0.+−.0.1); serine (+0.3); asparagine (+0.2); glutamine (+0.2); glycine (0); threonine (−0.4); proline (−0.5.+−.0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4) (U.S. Pat. No. 4,554,101).

In addition to the peptidyl compounds described herein, sterically similar compounds may be formulated to mimic the key portions of the peptide structure and that such compounds may also be used in the same manner as the peptides of the invention.

This may be achieved by techniques of modelling and chemical designing known to those of skill in the art. For example, esterification and other alkylations may be employed to modify the amino terminus of, e.g., a di-arginine peptide backbone, to mimic a tetra peptide structure. It will be understood that all such sterically similar constructs fall within the scope of the present invention.

Variants and functional equivalents of ML-IAP also includes derivatives of ML-IAP or fragments thereof, for example ML-IAP or ML-IAP fragments substituted with one or more chemical moieties.

Peptides with N-terminal alkylations and C-terminal esterifications are also encompassed within the present invention. Functional equivalents also comprise glycosylated and covalent or aggregative conjugates formed with the same or other ML-IAP fragments, including dimers or unrelated chemical moieties. Such functional equivalents are prepared by linkage of functionalities to groups which are found in fragment including at any one or both of the N- and C-termini, by means known in the art.

Functional equivalents may thus comprise ML-IAP fragments conjugated to aliphatic or acyl esters or amides of the carboxyl terminus, alkylamines or residues containing carboxyl side chains, e.g., conjugates to alkylamines at aspartic acid residues; O-acyl derivatives of hydroxyl group-containing residues and N-acyl derivatives of the amino terminal amino acid or amino-group containing residues, e.g. conjugates with fMet-Leu-Phe or immunogenic proteins. Derivatives of the acyl groups are selected from the group of alkyl-moieties (including C3 to C10 normal alkyl), thereby forming alkanoyl species, and carbocyclic or heterocyclic compounds, thereby forming aroyl species. The reactive groups preferably are difunctional compounds known per se for use in cross-linking proteins to insoluble matrices through reactive side groups.

Covalent or aggregative functional equivalents and derivatives thereof are useful as reagents in immunoassays or for affinity purification procedures. For example, a ML-IAP fragment according to the present invention may be insolubilized by covalent bonding to cyanogen bromide-activated Sepharose by methods known per se or adsorbed to polyolefin surfaces, either with or without glutaraldehyde cross-linking, for use in an assay or purification of anti-ML-IAP fragment antibodies or cell surface receptors. Fragments may also be labelled with a detectable group, e.g., radioiodinated by the chloramine T procedure, covalently bound to rare earth chelates or conjugated to another fluorescent moiety for use in e.g. diagnostic assays.

ML-IAP fragments according to the invention may be synthesised both in vitro and in vivo. In one embodiment the ML-IAP fragments of the invention are synthesised by automated synthesis. Any of the commercially available solid-phase techniques may be employed, such as the Merrifield solid phase synthesis method, in which amino acids are sequentially added to a growing amino acid chain. (See Merrifield, J. Am. Chem. Soc. 85:2149-2146, 1963).

Equipment for automated synthesis of polypeptides is commercially available from suppliers such as Applied Biosystems, Inc. of Foster City, Calif., and may generally be operated according to the manufacturer's instructions. Solid phase synthesis will enable the incorporation of desirable amino acid substitutions into any ML-IAP fragment according to the present invention. It will be understood that substitutions, deletions, insertions or any subcombination thereof may be combined to arrive at a final sequence of a functional equivalent. Insertions shall be understood to include amino-terminal and/or carboxyl-terminal fusions, e.g. with a hydrophobic or immunogenic protein or a carrier such as any polypeptide or scaffold structure capable as serving as a carrier.

Oligomers including dimers including homodimers and heterodimers of ML-IAP fragments according to the invention are also provided and fall under the scope of the invention. Functional equivalents and variants of ML-IAP fragments can be produced as homodimers or heterodimers with other amino acid sequences or with native ML-IAP sequences. Heterodimers include dimers containing immunoreactive ML-IAP fragments as well as ML-IAP fragments that need not have or exert any biological activity.

EXAMPLES

The following section serves to more fully describe the manner of using the above-described invention, as well as to set forth the best modes contemplated for carrying out various aspects of the invention. It is understood that these examples in no way serve to limit the true scope of this invention, but rather are presented for illustrative purposes.

Example 1

Materials and Methods

Peptides

All peptides were purchased from Research Genetics (Huntsville, Ala., USA) and provided at >80% purity as verified by HPLC and MS analysis. All peptides used are listed in Table 1.

Assembly Assay for Peptide Binding to Class I MHC Molecules

Assembly assays for binding of the synthetic peptides to class I MHC molecules metabolically labeled with [$^{35}$S]-methionine were carried out as described[15,16]. The assembly assay is based on stabilization of the class 1 molecule after loading of peptide to the peptide transporter deficient cell line T2. Subsequently correctly folded stable MHC heavy chains are immunoprecipitated using conformation-dependent antibodies. After IEF electrophoresis, gels were exposed to phosphorImager screens, and peptide binding was quantitated using the Imagequant PhosphorImager program (Molecular Dynamics, Sunnyvale, Calif.).

Antigen Stimulation of PBL

To extend the sensitivity of the ELISPOT assay, PBL were stimulated once in vitro prior to analysis[17,18]. At day 0, PBL or crushed lymph nodes were thawed and plated in 2 ml/well at a concentration of 2×10$^6$ cells in 24-well plates (Nunc, Denmark) in X-vivo medium (Bio Whittaker, Walkersville, Md.), 5% heat-inactivated human serum, and 2 mM of L-glutamine in the presence of 10 μM of peptide. Two days later 20 IU/ml recombinant interleukin-2 (IL-2) (Chiron, Ratingen, Germany) was added to the cultures. The cultured cells were tested for reactivity in the ELISPOT on day 12.

ELISPOT Assay

The ELISPOT assay used to quantify peptide epitope-specific interferon-γ-releasing effector cells was performed as described previously[19]. Briefly, nitrocellulose bottomed 96-well plates (MultiScreen MAIP N45, Millipore, Hedehusene, Denmark) were coated with anti-IFN-γ antibody (1-D1K, Mabtech, Nacka, Sweden). The wells were washed, blocked by X-vivo medium, and cells were added in duplicates at different cell concentrations. Peptides were then added to each well and the plates were incubated overnight. The following day, media was discarded and the wells were washed prior to addition of biotinylated secondary antibody (7-B6-1-Biotin, Mabtech). The plates were incubated for 2 hours, washed and Avidin-enzyme conjugate (AP-Avidin, Calbiochem, Life Technologies) was added to each well. Plates were incubated at RT for 1 hour and the enzyme substrate NBT/BCIP (Gibco, Life Technologies) was added to each well and incubated at RT for 5-10 min. The reaction was terminated by washing with tap-water upon the emergency of dark purple spots. The spots were counted using the AlphaImager System (Alpha Innotech, San Leandro, Calif. USA) and the peptide specific CTL frequency could be calculated from the numbers of spot-forming cells. The assays were all performed in duplicates for each peptide antigen.

Example 2

The present example demonstrates that ML-IAP is recognized as a tumor antigen in cancer patients as ML-IAP is subjected to T-cell responses.

The amino acid sequence of the ML-IAP polypeptide was screened for conceivable HLA-A2 nonamer and HLA-A2 decamer peptide epitopes by using the main HLA-A2 specific anchor residues[20].

Twelve ML-IAP deduced peptides were synthesized and examined for binding to HLA-A2 by comparison with the HLA-A2 high affinity positive control epitope from HIV-1 $pol_{476-484}$ (ILKEPVHGV) (Table 1). The peptide concentration required for half maximal recovery of class I MHC($C_{50}$ value) were 0.2 µM for the positive control.

Five ML-IAP peptides bound with similar high affinity as the positive control; $MLIAP_{245}$, $MLIAP_{90}$, $MLIAP_{34}$, $MLIAP_{54}$, and $MLIAP_{99}$ ($C_{50}$=1, 0.2, 1, 1, and 0.9 µM, respectively) (Table 1). The peptides $MLIAP_{280}$, $MLIAP_{83}$, and $MLIAP_{154}$ bound in comparison with intermediate affinity ($C_{50}$=20, 30 and 10 µM, respectively), whereas the peptides $MLIAP_{230}$ and $MLIAP_{98}$ bound only weakly to HLA-A2 ($C_{50}$>100 µM). Two of the peptides examined ($MLIAP_{261}$, $MLIAP_{200}$) did not bind to HLA-A2 (Table 1).

Using the ELISPOT IFN-γ secretion assay, we examined the presence of specific T-cell responses against the ML-IAP deduced, HLA-A2 binding peptides in peripheral blood T cells (n=7) or TIL (n=22) from melanoma patients. The high sensitivity of this assay allows reliable detection of as few as 10-100 specific T cells/1 million. In addition, before analysis, the T-cells were stimulated once in vitro to extend the sensitivity. This method has previously been shown to be highly effective to identify peptide epitopes recognized by CTL in cancer patients[10,21,22]. In contrast, other ex vivo assays such as intracellular IFN-γ staining or tetramer analysis by flow cytometry require approximately 10-fold higher specific T-cell frequencies for their detection.

In the first series of experiments T-cell reactivity against all 12 deduced ML-IAP peptides was examined. Based on these preliminary results we also included the weak HLA-A2 binding peptide $ML-IAP_{230}$ besides the better binding peptides for further analysis. The strongest CTL responses were detected against the intermediate HLA-A2 binding peptide $ML-IAP_{280}$ (QLCPICRAPV), and such responses were detectable in both TIL and PBL.

Figure 2:
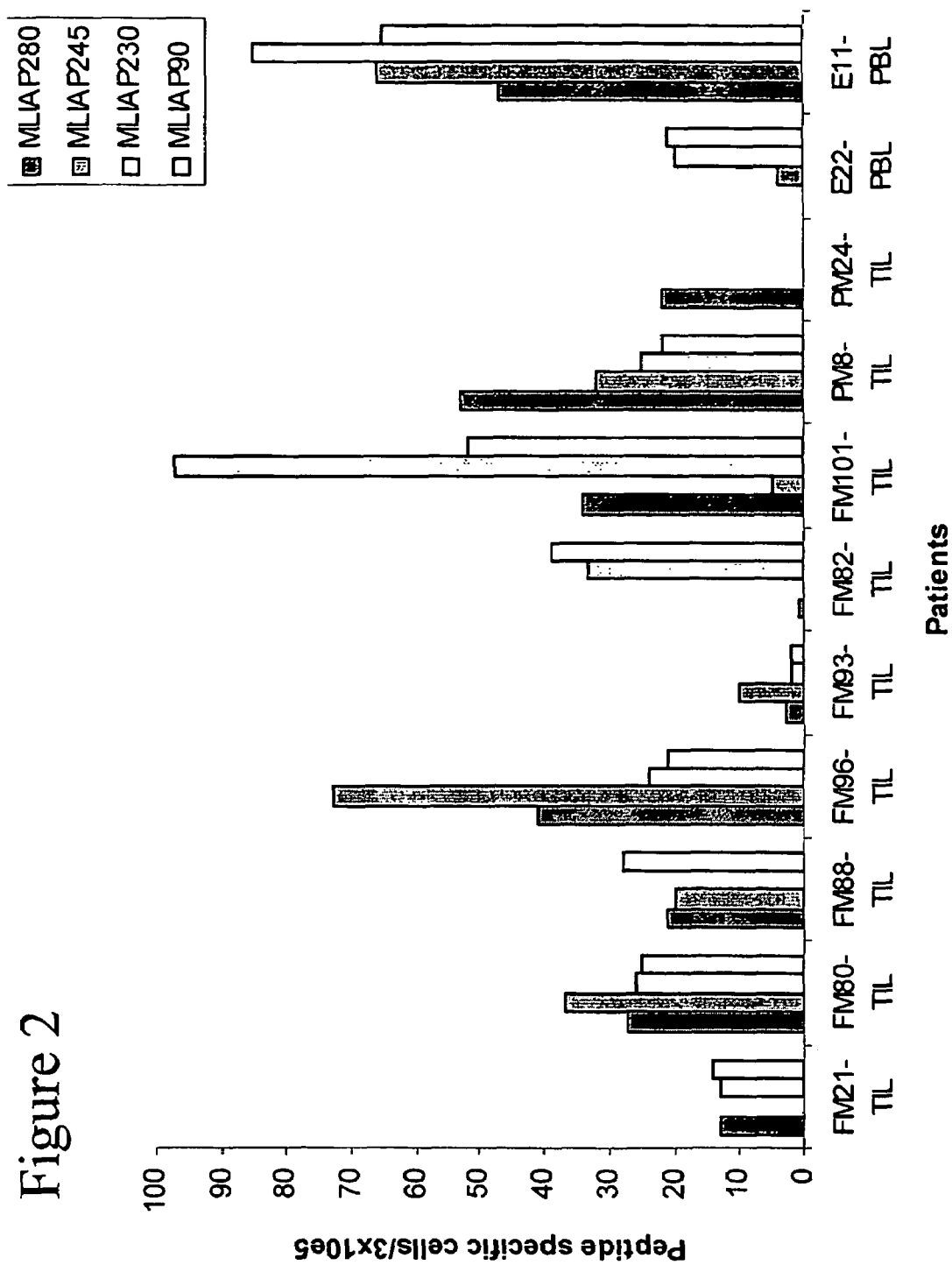

FIG. 1 illustrates these strong spontaneous responses detected in TIL and PBL from three melanoma patients (FIG. 1 A-D); each spot represents a peptide reactive, IFN-γ producing cell. The average number of spots per peptide was calculated using a CCD scanning device and a computer system (FIG. 1 E). In addition, we were able to detect a response against $ML-IAP_{280}$ in one of the PBL samples and in TIL from seven patients (FIG. 2). Moreover, a response was detected against the strong HLA-A2 binding peptide $ML-IAP_{245}$ (RLQEERTCKV) in five of the TIL and one of the PBL samples (FIG. 2). Further, we identified reactivity against the strong HLA-A2 binding peptide $ML-IAP_{90}$ (RLASFYDWPL) in seven TIL samples and in PBL from two patients (FIG. 2). Surprisingly, a response was detected against the weak HLA-A2 binding peptide $ML-IAP_{230}$ (VLEPPGARDV) in six TIL cultures and in two samples of PBL even though this peptide were not able to stabilize the HLA-A2 molecule (FIG. 2).

Eleven of the 22 TIL samples and three of the seven PBL samples did not display any ML-IAP specific response (data not shown). Thus, spontaneous T-cell responses against ML-IAP was detected in approximately half of the patients examined.

Accordingly, fragments of the ML-IAP polypeptide was analysed for the presence of HLA-A2 binding motifs and—after successful identification—the fragments were used to test for specific T-cell reactivity in melanoma patients by ELISPOT assay. Following this strategy, we successfully identified strong CTL responses against the intermediate HLA-A2 binding peptide $ML-IAP_{280}$.

Weaker spontaneous responses could be detected against three additional peptide epitopes, the strong HLA-A2 binding peptides $ML-IAP_{245}$ and $ML-IAP_{90}$ and the very weak binding peptide $ML-IAP_{230}$. In that respect, it is worth taking note that there are many factors, which determine a CTL response against a given peptide. These include expression level of the relevant source polypeptide, processing, TAP-transport, expression level of the class I MHC on the cell surface, TCR repertoire, CTL sensitivity, immuno-suppression and cytokines[23]. Thus, peptide binding to class I is one in a number of different factors which determine the immunogenicity of a given peptide. Additionally, in contrast to foreign peptides, when self-peptides are expressed on the cell surface at high density due to high MHC-binding affinity, tolerance seems to be induced, and reactive T cells are eliminated or inactivated[24].

Subsequently, many immunodominant epitopes in CTL responses to self polypeptides may frequently be subdominant or cryptic, rather than dominant determinants. This may explain the observation that many epitopes from human melanoma antigens, which are non-mutated self-polypeptides, such as gp100 and MART-1 have relatively low binding affinities to class I MHC[25]. Given that the efficacy of tumor immunotherapy most likely depends on the avidity of recruited CTL[32], low affinity tumor epitopes might be important TAA, provided that they are able to mobilize their specific CTL repertoire and that they are presented by tumor cells efficiently enough to be recognized by CTL.

Example 3

One of the HLA-A2 antigen restricted epitopes identified from ML-IAP was the decamer peptide $ML-IAP_{245}$ (RLQEERTCKV). The following example relates to the analogue nona-mer peptide $ML-IAP_{245-253}$ (RLQEERTCK).

Figure 3:
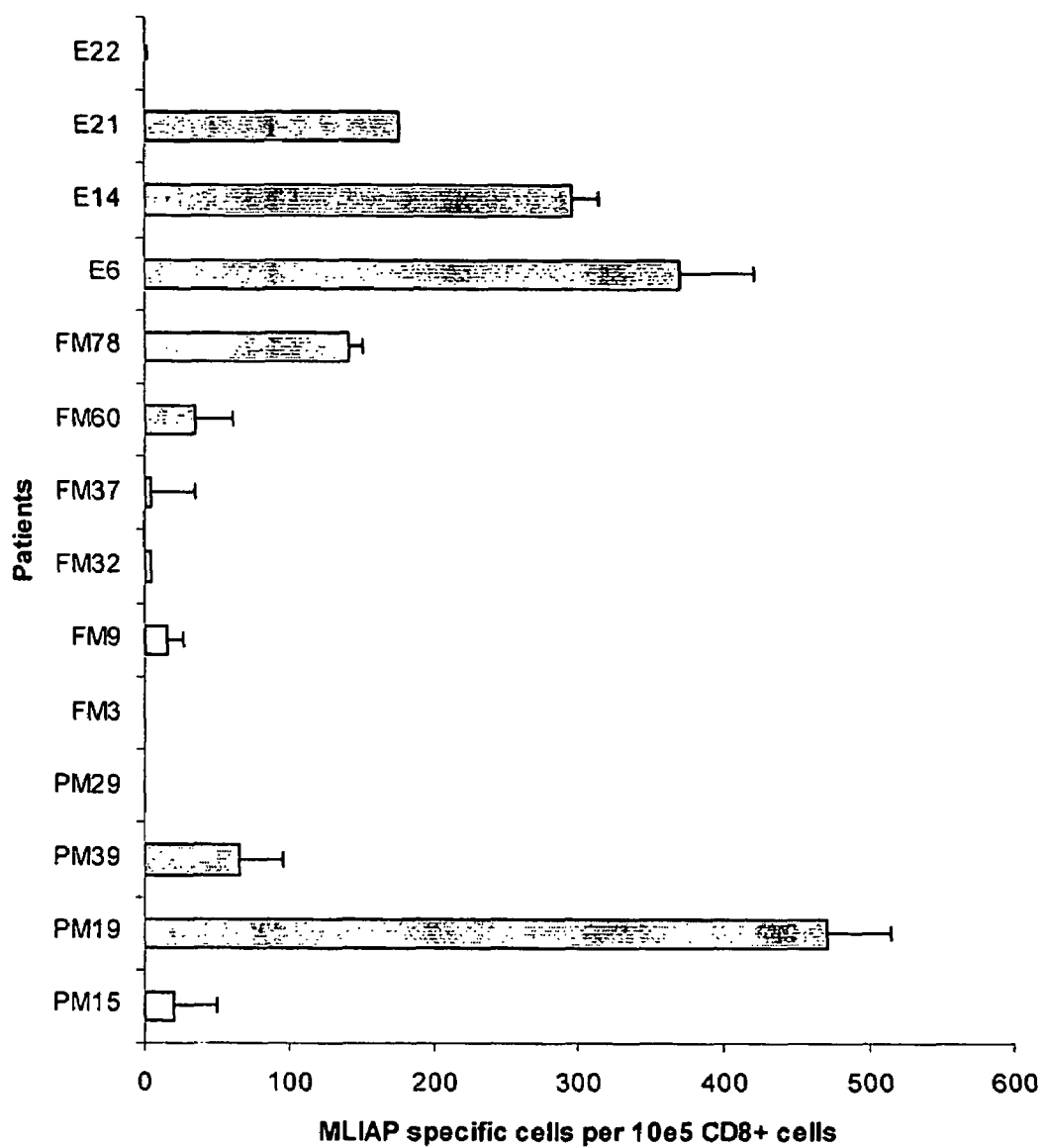

The deca-mer peptide is presented by melanoma-cells in the context of the HLA-A2 antigen. To investigate whether the nona-mer peptide likewise is generated by the antigen-processing machinery and subsequently is presented in the context of HLA-A3 antigen, we analyzed PBL from 14 HLA-A3 antigen positive melanoma patients for spontaneous immune responses by means of ELISPOT against this peptide. To this end, five of the melanoma patients hosted an immune response of more than 200 $mL-IAP_{245-253}$ (RLQEERTCK) specific T-cells per $10^5$ CD8+ cells (FIG. 3).

Thus, spontaneous immune responses against this epitope are present in around one third of the HLA-A3 antigen positive patients.

The characterization of multiple ML-IAP epitopes with different class I restriction elements broadens the clinical potential of this target antigen in two important ways: On one hand it increases the number of patients eligible for immunotherapy based on ML-IAP derived peptides, since although the HLA-A2 antigen is one of the most frequently expressed HLA class I molecules, it is still only expressed in around 50% of melanoma patients. The HLA-A3 antigen is expressed in by 30% of patients[34]. Co-expression is found in around 10% of patients. Thus, approximately 70% of the patients can be vaccinated with the ML-IAP epitopes identified.

On the other hand the collective targeting of several restriction elements, is likely to decrease the risk of immune escape by class I HLA-allele loss. Loss of a single class I HLA allele is a significant component of MHC alterations described in cancer cells, whereas total loss of class I HLA expression is a rather infrequent event. Although the percentage of patients expressing both HLA-A2 and HLA-A3 antigens is only 10%, the identification of epitopes for other class I HLA alleles does increase this percentage of patients with allelic overlap.

Example 4

ML-IAP-reactive T cells were detected in situ in the following way.

Figure 4:
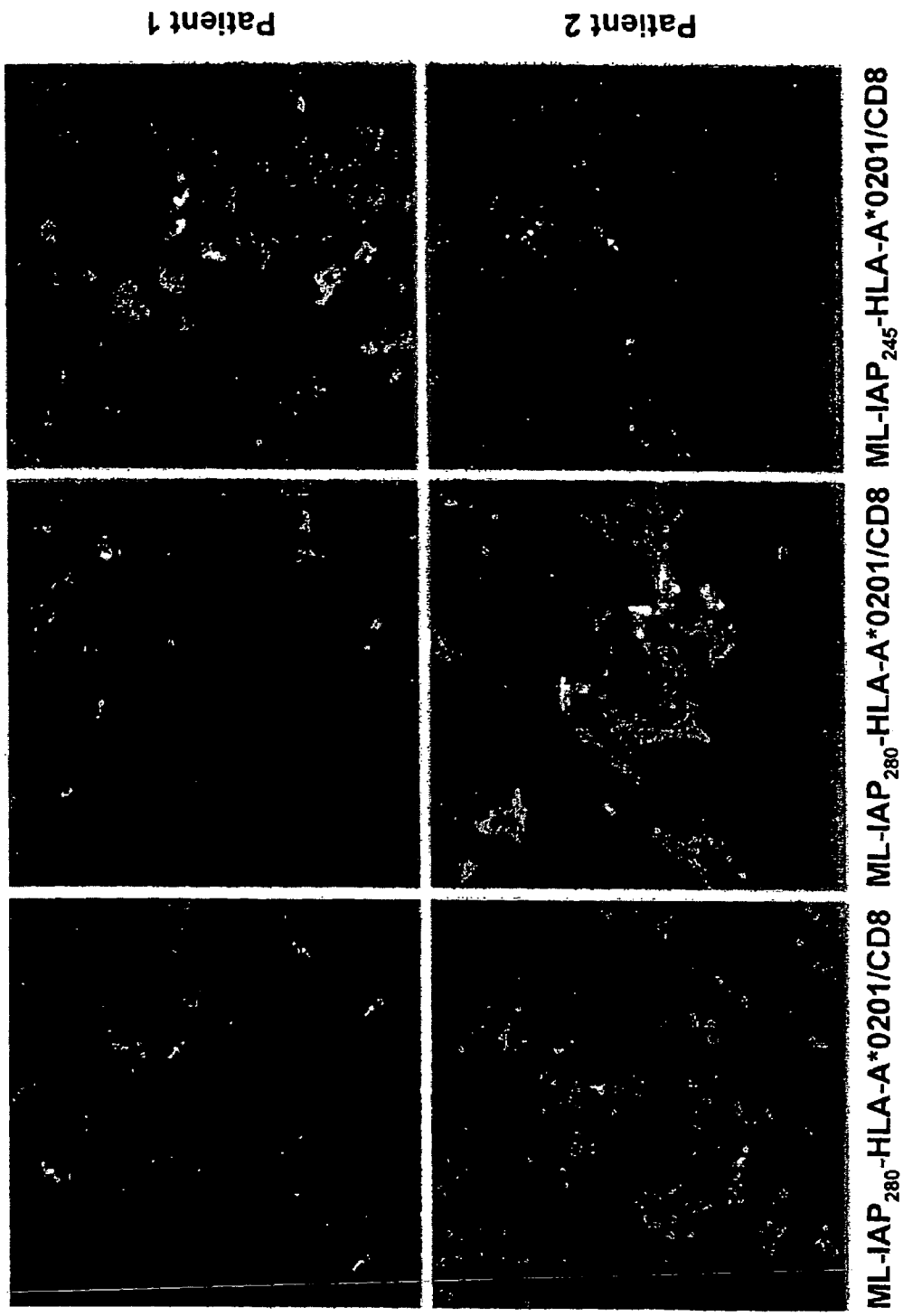

HLA-A2 and ML-IAP$_{245}$/HLA-A2-specific monomers were multimerized using dextran molecules, which were conjugated with both streptavidin and fluorescein isothiocyanate. Multimerized MHC complexes were used to stain acetone-fixed, frozen material as described previously[11,48] and antigen-specific cells were visualized using a confocal laser microscope. Sections of primary melanoma from six patients were analyzed, and ML-IAP$_{280}$- and ML-IAP$_{245}$-reactive CTL could readily be detected in situ in the tumor microenvironment in two of the patients (FIG. 4).

Example 5

To characterize the functional capacity of ML-IAP-reactive CTL, these cells were isolated by means of magnetic beads coated with HLA-A2/ML-IAP complexes in a manner similar to that described in Schrama et al., 2001[36]. ML-IAP$_{245}$-specific cells were directly isolated from PBL (FIG. 5A). ML-IAP$_{280}$-reactive cells were enriched from TIL of a melanoma infiltrated lymph node after being stimulated once in vitro with peptide. These cells lyzed T2-cells in a peptide-specific manner (FIG. 4B). Additionally, we tested the cytotoxicity of the ML-IAP$_{280}$-reactive CTL against the autologous melanoma line FM72, the HLA-A2-matched melanoma cell line FM93 and the HLA mismatched melanoma cell line FM56. This analysis revealed that the ML-IAP$_{280}$-reactive T cells efficiently lyzed both the autologous and the HLA-matched melanoma cell lines. In contrast, no cytotoxicity was observed against the HLA-A2-negative melanoma cell line FM56 or the natural killer target cell K562 (FIG. 4C).

The data presented herein above demonstrate that ML-IAP, which is of crucial importance for the survival of a cancer cell, represent a novel tumor antigen. IAPs such as ML-IAP can advantageously be used for vaccination purposes as downregulation or loss of the expression of such polypeptides (otherwise constituting a form of immune escape) would impair sustained tumor growth. Specific useful peptides are identified.

LIST OF REFERENCES

1. Van den Eynde, B. J. and Boon, T. (1997). Tumor antigens recognized by T lymphocytes. Int. J. Clin. Lab. Res. 27, 81-86.
2. Heslop, H. E. and Rooney, C. M. (1997). Adoptive cellular immunotherapy for EBV lymphoproliferative disease. Immunol Rev. 157, 217-222.
3. Rosenberg, S. A., Yang, J. C., Schwartzentruber, D. J., Hwu, P., Marincola, F. M., Topalian, S. L., Restifo, N. P., Dudley, M. E., Schwarz, S. L., Spiess, P. J., Wunderlich, J. R., Parkhurst, M. R., Kawakami, Y., Seipp, C. A., Einhorn, J. H., and White, D. E. (1998). Immunologic and therapeutic evaluation of a synthetic peptide vaccine for the treatment of patients with metastatic melanoma. Nat. Med. 4, 321-327.
4. Nestle, F. O., Alijagic, S., Gilliet, M., Sun, Y., Grabbe, S., Dummer, R., Burg, G., and Schadendorf, D. (1998). Vaccination of melanoma patients with peptide- or tumor lysate-pulsed dendritic cells. Nat. Med. 4, 328-332.
5. Thurner, B., Haendle, I., Roder, C., Dieckmann, D., Keikavoussi, P., Jonuleit, H., Bender, A., Maczek, C., Schreiner, D., von den Driesch, P., Brocker, E. B., Steinman, R. M., Enk, A., Kampgen, E., and Schuler, G. (1999). Vaccination with mage-3A1 peptide-pulsed mature, monocyte-derived dendritic cells expands specific cytotoxic T cells and induces regression of some metastases in advanced stage 1V melanoma. J. Exp. Med. 190, 1669-1678.
6. Rosenberg, S. A. (1996). Development of cancer immunotherapies based on identification of the genes encoding cancer regression antigens. J. Natl. Cancer Inst. 20, 1635-1644.
7. Marchand, M., van Baren, N., Weynants, P., Brichard, V., Dreno, B., Tessier, M. H., Rankin, E., Parmiani, G., Arienti, F., Humblet, Y., Bourlond, A., Vanwijck, R., Lienard, D., Beauduin, M., Dietrich, P. Y., Russo, V., Kerger, J., Masucci, G., Jager, E., De Greve, J., Atzpodien, J., Brasseur, F., Coulie, P. G., van der Bruggen, P., and Boon, T. (1999). Tumor regressions observed in patients with metastatic melanoma treated with an antigenic peptide encoded by gene MAGE-3 and presented by HLA-A1. Int. J. Cancer 80, 219-230.
8. Cormier, J. N., Abati, A., Fetsch, P., Hijazi, Y. M., Rosenberg, S. A., Marincola, F. M., and Topalian, S. L. (1998). Comparative analysis of the in vivo expression of tyrosinase, MART-1/Melan-A, and gp100 in metastatic melanoma lesions: implications for immunotherapy. J. Immunother. 21, 27-31.
9. Becker, J. C., Schwinn, A., Dummer, R., Burg, G., and Brocker, E. B. (1993). Lesion-specific activation of cloned human tumor-infiltrating lymphocytes by autologous tumor cells: induction of proliferation and cytokine production. J. Invest. Dermatol. 101, 15-21.
10. Andersen, M. H., Pedersen, L. O., Becker, J. C., and thor Straten, P. (2001). Identification of a Cytotoxic T Lymphocyte Response to the Apoptose Inhibitor Polypeptide Survivin in Cancer Patients. Cancer Res. 61, 869-872.
11. Andersen, M. H., Pedersen, L. O., Capeller, B., Brocker, E. B., Becker, J. C., and thor, S. P. (2001). Spontaneous cytotoxic T-cell responses against survivin-derived MHC class I-restricted T-cell epitopes in situ as well as ex vivo in cancer patients. Cancer Res. 61, 5964-5968.

12. Jaattela, M. (1999). Escaping cell death: survival polypeptides in cancer. Exp. Cell Res. 248, 30-43.
13. Kasof, G. M. and Gomes, B. C. (2001). Livin, a novel inhibitor of apoptosis polypeptide family member. J. Biol. Chem. 276, 3238-3246.
14. Vucic, D., Stennicke, H. R., Pisabarro, M. T., Salvesen, G. S., and Dixit, V. M. (2000). ML-IAP, a novel inhibitor of apoptosis that is preferentially expressed in human melanomas. Curr. Biol. 10, 1359-1366.
15. Andersen, M. H., Sondergaard, I., Zeuthen, J., Elliott, T., and Haurum, J. S. (1999). An assay for peptide binding to HLA-Cw*0102. Tissue Antigens. 54, 185-190.
16. Andersen, M. H., Bonfill, J. E., Neisig, A., Arsequell, G., Sondergaard, I., Neefjes, J., Zeuthen, J., Elliott, T., and Haurum, J. S. (1999). Phosphorylated Peptides Can Be Transported by TAP Molecules, Presented by Class I MHC Molecules, and Recognized by Phosphopeptide-Specific CTL. J. Immunol. 163, 3812-3818.
17. McCutcheon, M., Wehner, N., Wensky, A., Kushner, M., Doan, S., Hsiao, L., Calabresi, P., Ha, T., Tran, T. V., Tate, K. M., Winkelhake, J., and Spack, E. G. (1997). A sensitive ELISPOT assay to detect low-frequency human T lymphocytes. J. Immunol. Methods 210, 149-166.
18. Pass, H. A., Schwarz, S. L., Wunderlich, J. R., and Rosenberg, S. A. (1998). Immunization of patients with melanoma peptide vaccines: immunologic assessment using the ELISPOT assay [see comments]. Cancer J. Sci. Am. 4, 316-323.
19. Berke, Z., Andersen, M. H., Pedersen, M., Fugger, L., Zeuthen, J., and Haurum, J. S. (2000). Peptides spanning the junctional region of both the abl/bcr and the bcr/abl fusion polypeptides bind common HLA class 1 molecules. Leukemia 14, 419-426.
20. Andersen, M. H., Tan, L., Sondergaard, I., Zeuthen, J., Elliott, T., and Haurum, J. S. (2000). Poor correspondence between predicted and experimental binding of peptides to class I MHC molecules. Tissue Antigens 55, 519-531.
21. Scheibenbogen, C., Sun, Y., Keilholz, U., Song, M., Stepvanovic, S., Asemissen, A. M., Nagorsen, D., Thiel, E., Rammensee, H. G., and Schadendorf, D. (2002). Identification of known and novel immunogenic T-cell epitopes from tumor antigens recognized by peripheral blood T cells from patients responding to IL-2-based treatment. Int. J. Cancer 20, 409-414.
22. Herr, W., Ranieri, E., Gambotto, A., Kierstead, L. S., Amoscato, A. A., Gesualdo, L., and Storkus, W. J. (1999). Identification of naturally processed and HLA-presented Epstein-Barr virus peptides recognized by CD4(+) or CD8(+) T lymphocytes from human blood. Proc. Natl. Acad. Sci. U.S.A 96, 12033-12038.
23. Yewdell, J. W. and Bennink, J. R. (1999). Immunodominance in major histocompatibility complex class I-restricted T lymphocyte responses. Annu. Rev. Immunol. 17, 51-88.
24. Moudgil, K. D. and Sercarz, E. E. (1994). Can antitumor immune responses discriminate between self and nonself? Immunol. Today 15, 353-355.
25. Parkhurst, M. R., Salgaller, M. L., Southwood, S., Robbins, P. F., Sette, A., Rosenberg, S. A., and Kawakami, Y. (1996). Improved induction of melanoma-reactive CTL with peptides from the melanoma antigen gp100 modified at HLA-A*0201-binding residues. J. Immunol. 157, 2539-2548.
26. Ashhab, Y., Alian, A., Polliack, A., Panet, A., and Ben Yehuda, D. (2001). Two splicing variants of a new inhibitor of apoptosis gene with different biological properties and tissue distribution pattern. FEBS Lett. 20, 56-60.
27. Jager, E., Ringhoffer, M., Altmannsberger, M., Arand, M., Karbach, J., Jager, D., Oesch, F., and Knuth, A. (1997). Immunoselection in vivo: independent loss of MHC class I and melanocyte differentiation antigen expression in metastatic melanoma. Int. J. Cancer 71, 142-147.
28. Yee, C., Thompson, J. A., Roche, P., Byrd, D. R., Lee, P. P., Piepkorn, M., Kenyon, K., Davis, M. M., Riddell, S. R., and Greenberg, P. D. (2000). Melanocyte destruction after antigen-specific immunotherapy of melanoma: direct evidence of t cell-mediated vitiligo. J. Exp. Med. 192, 1637-1644.
29. Ennis, F. A., Yi-Hua, Q., and Schild, G. C. (1982). Antibody and cytotoxic T lymphocyte responses of humans to live and inactivated influenza vaccines. J. Gen. Virol. 58, 273-81.
30. Battegay, M., Moskophidis, D., Waldner, H., Brundler, M. A., Fung-Leung, W. P., Mak, T. W., Hengartner, H., Zinkernagel, R. M. (1993). Impairment and delay of neutralizing antiviral antibody responses by virus-specific cytotoxic T cells. J. Immunol. 15, 5408-15.
31. Elvin, J., Potter, C., Elliott, T., Cerundolo, V., and Townsend, A. (1993). A method to quentify binding of unlabeled peptides to class I MHC molecules and detect their allele specificity. J. Immunol. Methods. 158, 161-171.
32. Zeh, H. J. 3rd, Perry-Lalley, D., Dudley, M. E., Rosenberg, S. A., and Yang, J. C (1999). High avidity CTLs for two self-antigens demonstrate superior in vitro and in vivo antitumor efficacy. J. Immunol., 162, 989-94.
33. Kubo, R. T., Sette, A., Grey, H. M., Appella, E., Sakaguchi, K., Zhu, N. Z., Arnott, D., Sherman, N., Shabanowitz, J., Michel, H., et al. (1994). Definition of specific peptide motifs for four major HLA-A alleles. J. Immunol. 152, 3913-3924.
34. Kessler, J. H., Mommaas, B., Mutis, T., Hujibers, I., Vissers, D., Benckhuijsen, W. E., Schreuder, G. M., Offringa, R., Goulmy, E., Melief, C. J., van der Burg, S. H., and Drijfhout, J. W. (2003). Competition-based cellular peptide binding assays for 13 prevalent HLA class I alleles using fluorescein-labeled synthetic peptides. Hum. Immunol. 64, 245-255.
35. Vonderheide, R. H., Anderson, K. S., Hahn, W. C., Butler, M. O., Schultze, J. L., and Nadler, L. M. (2001). Characterization of HLA-A3-restricted cytotoxic T lymphocytes reactive against the widely expressed tumor antigen telomerase. Clin. Cancer Res. 7, 3343-3348.
36. Schrama, D., Andersen, M. H., Terheyden, P., Schroder, L., Pedersen, L. O., thor Straten, P., Becker, J. C. (2001). Oligoclonal T-cell receptor usage of melanocyte differentiation antigen-reactive T cells in stage IV melanoma patients. Cancer Res. 61, 493-496.
37. Lalvani, A., Brookes, R., Hambleton, S., Britton, W. J., Hill, A. V. S., and McMichael, A. J. (1997). Rapid effector function in CD8+ memory T cells. J. Exp. Med. 186, 859-865.
38. Scheibenbogen, C., Lee, K. H., Mayer, S., Stevanovic, S., Moebius, U., Herr, W., Rammensee, H. G., and Keilholz, U. (1997). A sensitive ELISPOT assay for detection of CD8+ T lymphocytes specific for HLA class I-binding peptide epitopes derived from influenza proteins in the blood of healthy donors and melanoma patients. Clin. Cancer Res. 3, 221-6.
39. Tan, L., Andersen, M. H., Elliott, T., and Haurum, J. S. (1997). An improved assembly assay for peptide binding to HLA-B*2705 and H-2K(k) class I MHC molecules, J. Immunol. Methods 209, 25.

40. Thurner, B., Roder, C., Dieckmann, D., Heuer, M., Kruse, M., Glaser, A., Keikavoussi, P., Kampgen, E., Bender, A., and Schuler, G. (1999) Generation of large numbers of fully mature and stable dendritic cells from leukopheresis products for clinical application J. Immunol. Methods 223, 1.

41. Oelke, M., Moehrle, U., Behringer, D., Lindemann, A., Mackensen, A. (2000). Activation and purification of Melan-A-specific human CD8+ T cells in vitro for adoptive transfer in tumor immunotherapy. Clin. Cancer Res. 6, 1997-2005.

42. Wang, F., Bade, E., Kuniyoshi, C., Spears, L., Jeffery, G., Marty, V., Groshen, S., and Weber, J. (1999). Phase I trial of a MART-1 peptide vaccine with incomplete Freund's adjuvant for resected high-risk melanoma. Clin. Cancer Res. 5, 2756.

43. Kensil, C. R., Patel, U., Lennick, M., Marciani, D. (1991). Separation and characterization of saponins with adjuvant activity from *Quillaja saponatria* Molina cortex. J. Immunol. 146, 431-437.

44. Kensil, C. R., Wu, J. Y., Soltysik, S. (1995). Structural and immunological characterization of the vaccine adjuvant QS-21. Pharmaceut. Biotechnol. 6, 525-541.

45. Cai, Z., Brunmark, A., Jackson, M. R., et al. (1996). Transfected *drosophila* cells as a probe for defining the minimal requirements for stimulating unprimed CD8+ T cells. Proc Natl Acad Sci USA 93, 14736-14741.

46. Sun, S., Cai, Z., Langlade-Demoyen, P., et al. (1996). Dual function of *Drosophila* cells as APCs for naive CD8+ T cells: Implications for tumor immunotherapy. Immunity 4, 555-564.

47. Luxembourg, A. T., Borrow, B., Teyton, L., et al. (1998). Biomagnetic isolation of antigen-specific CD8+ T cells usable in immunotherapy. Nat Biotechnol 16, 281-285.

48. Schrama, D., Pedersen, L. O., Keikavoussi, P., Andersen, M. H., thor Straten, P., Brocker, E. B., Kampgen, E., and Becker, J. C. (2002). Aggregation of antigen-specific T cells at the inoculation site of mature dendritic cells. J. Invest. Dermatol. 119, 1443-1448.

What is claimed is:

1. A method for raising a specific T-cell response against an epitope of ML-IAP (SEQ ID NO:1) in an individual, said method comprising the steps of administering to the individual a polypeptide capable of raising a specific T-cell response, said polypeptide comprising a peptide selected from the group consisting of: RLQEERTCK (SEQ ID NO:245), RLQEERTCKV {SEQ ID NO:297), QLCPICRAPV (SEQ ID NO:298), and VLEPPGARDV (SEQ ID NO:301); wherein said polypeptide comprises at the most 15 amino acids, and raising a specific T-cell response against an epitope of ML-IAP in the individual.

2. The method of claim 1, wherein said polypeptide comprises the peptide RLQEERTCK (SEQ ID NO: 245).

3. The method of claim 1, wherein said polypeptide comprises the peptide RLQEERTCKV (SEQ ID NO: 297).

4. The method of claim 1, wherein said polypeptide comprises the peptide QLCPICRAPV (SEQ ID NO: 298).

5. The method of claim 1, wherein said polypeptide comprises the peptide VLEPPGARDV (SEQ ID NO: 301).

6. The method of claim 1, further comprising administering an adjuvant to the individual.

7. The method of claim 1, wherein the adjuvant is Montanide IAS-51 or QS-21.

8. The method of claim 1, wherein said administering comprises administering to said individual at least one peptide capable of binding an HLA molecule expressed in the individual.

9. The method of claim 1, wherein the individual has at least one of tissue type HLA-A2 and HLA-A3.

* * * * *

UNITED STATES PATENT AND TRADEMARK OFFICE
CERTIFICATE OF CORRECTION

PATENT NO. : 7,687,465 B2  Page 1 of 1
APPLICATION NO. : 10/553078
DATED : March 30, 2010
INVENTOR(S) : Per Thor Straten and Mads Hald Andersen It is certified that error appears in the above-identified patent and that said Letters Patent is hereby corrected as shown below:

Title Page; item (73); Assignee on Cover Page; delete "Kraeftens Bekaempelse" and insert
-- Survac ApS --.

Signed and Sealed this

Twenty-eighth Day of September, 2010

David J. Kappos
*Director of the United States Patent and Trademark Office*

SEQUENCE LISTING

```
<160> NUMBER OF SEQ ID NOS: 318

<210> SEQ ID NO 1
<211> LENGTH: 297
<212> TYPE: PRT
<213> ORGANISM: Homo sapiens

<400> SEQUENCE: 1

Met Gly Pro Lys Asp Ser Ala Lys Cys Leu His Arg Gly Pro Gln Pro
1               5                   10                  15

Ser His Trp Ala Ala Gly Asp Gly Pro Thr Gln Glu Arg Cys Gly Pro
            20                  25                  30

Arg Ser Leu Gly Ser Pro Val Leu Gly Leu Asp Thr Cys Arg Ala Trp
        35                  40                  45

Asp His Val Asp Gly Gln Ile Leu Gly Gln Leu Arg Pro Leu Thr Glu
    50                  55                  60

Glu Glu Glu Glu Gly Ala Gly Ala Thr Leu Ser Arg Gly Pro Ala
65                  70                  75                  80

Phe Pro Gly Met Gly Ser Glu Glu Leu Arg Leu Ala Ser Phe Tyr Asp
                85                  90                  95

Trp Pro Leu Thr Ala Glu Val Pro Pro Glu Leu Leu Ala Ala Ala Gly
            100                 105                 110

Phe Phe His Thr Gly His Gln Asp Lys Val Arg Cys Phe Phe Cys Tyr
        115                 120                 125

Gly Gly Leu Gln Ser Trp Lys Arg Gly Asp Asp Pro Trp Thr His Ala
    130                 135                 140

Lys Trp Phe Pro Ser Cys Gln Phe Leu Leu Arg Ser Lys Gly Arg Asp
145                 150                 155                 160

Phe Val His Ser Val Gln Glu Thr His Ser Gln Leu Leu Gly Ser Trp
                165                 170                 175

Asp Pro Trp Glu Glu Pro Glu Asp Ala Ala Pro Val Ala Pro Ser Val
            180                 185                 190

Pro Ala Ser Gly Tyr Pro Glu Leu Pro Thr Pro Arg Arg Glu Val Gln
        195                 200                 205

Ser Glu Ser Ala Gln Glu Pro Gly Gly Val Ser Pro Ala Glu Ala Gln
    210                 215                 220
```

```
Arg Ala Trp Trp Val Leu Glu Pro Pro Gly Ala Arg Asp Val Glu Ala
225                 230                 235                 240

Gln Leu Arg Arg Leu Gln Glu Glu Arg Thr Cys Lys Val Cys Leu Asp
            245                 250                 255

Arg Ala Val Ser Ile Val Phe Val Pro Cys Gly His Leu Val Cys Ala
            260                 265                 270

Glu Cys Ala Pro Gly Leu Gln Leu Cys Pro Ile Cys Arg Ala Pro Val
        275                 280                 285

Arg Ser Arg Val Arg Thr Phe Leu Ser
    290                 295

<210> SEQ ID NO 2
<211> LENGTH: 9
<212> TYPE: PRT
<213> ORGANISM: Homo sapiens

<400> SEQUENCE: 2

Met Gly Pro Lys Asp Ser Ala Lys Cys
1               5

<210> SEQ ID NO 3
<211> LENGTH: 9
<212> TYPE: PRT
<213> ORGANISM: Homo sapiens

<400> SEQUENCE: 3

Gly Pro Lys Asp Ser Ala Lys Cys Leu
1               5

<210> SEQ ID NO 4
<211> LENGTH: 9
<212> TYPE: PRT
<213> ORGANISM: Homo sapiens

<400> SEQUENCE: 4

Pro Lys Asp Ser Ala Lys Cys Leu His
1               5

<210> SEQ ID NO 5
<211> LENGTH: 9
<212> TYPE: PRT
<213> ORGANISM: Homo sapiens

<400> SEQUENCE: 5

Lys Asp Ser Ala Lys Cys Leu His Arg
1               5

<210> SEQ ID NO 6
<211> LENGTH: 9
<212> TYPE: PRT
<213> ORGANISM: Homo sapiens

<400> SEQUENCE: 6

Asp Ser Ala Lys Cys Leu His Arg Gly
1               5

<210> SEQ ID NO 7
<211> LENGTH: 9
<212> TYPE: PRT
<213> ORGANISM: Homo sapiens

<400> SEQUENCE: 7
```

```
Ser Ala Lys Cys Leu His Arg Gly Pro
1               5

<210> SEQ ID NO 8
<211> LENGTH: 9
<212> TYPE: PRT
<213> ORGANISM: Homo sapiens

<400> SEQUENCE: 8

Ala Lys Cys Leu His Arg Gly Pro Gln
1               5

<210> SEQ ID NO 9
<211> LENGTH: 9
<212> TYPE: PRT
<213> ORGANISM: Homo sapiens

<400> SEQUENCE: 9

Lys Cys Leu His Arg Gly Pro Gln Pro
1               5

<210> SEQ ID NO 10
<211> LENGTH: 9
<212> TYPE: PRT
<213> ORGANISM: Homo sapiens

<400> SEQUENCE: 10

Cys Leu His Arg Gly Pro Gln Pro Ser
1               5

<210> SEQ ID NO 11
<211> LENGTH: 9
<212> TYPE: PRT
<213> ORGANISM: Homo sapiens

<400> SEQUENCE: 11

Leu His Arg Gly Pro Gln Pro Ser His
1               5

<210> SEQ ID NO 12
<211> LENGTH: 9
<212> TYPE: PRT
<213> ORGANISM: Homo sapiens

<400> SEQUENCE: 12

His Arg Gly Pro Gln Pro Ser His Trp
1               5

<210> SEQ ID NO 13
<211> LENGTH: 9
<212> TYPE: PRT
<213> ORGANISM: Homo sapiens

<400> SEQUENCE: 13

Arg Gly Pro Gln Pro Ser His Trp Ala
1               5

<210> SEQ ID NO 14
<211> LENGTH: 9
<212> TYPE: PRT
<213> ORGANISM: Homo sapiens

<400> SEQUENCE: 14

Gly Pro Gln Pro Ser His Trp Ala Ala
1               5
```

```
<210> SEQ ID NO 15
<211> LENGTH: 9
<212> TYPE: PRT
<213> ORGANISM: Homo sapiens

<400> SEQUENCE: 15

Pro Gln Pro Ser His Trp Ala Ala Gly
1               5

<210> SEQ ID NO 16
<211> LENGTH: 9
<212> TYPE: PRT
<213> ORGANISM: Homo sapiens

<400> SEQUENCE: 16

Gln Pro Ser His Trp Ala Ala Gly Asp
1               5

<210> SEQ ID NO 17
<211> LENGTH: 9
<212> TYPE: PRT
<213> ORGANISM: Homo sapiens

<400> SEQUENCE: 17

Pro Ser His Trp Ala Ala Gly Asp Gly
1               5

<210> SEQ ID NO 18
<211> LENGTH: 9
<212> TYPE: PRT
<213> ORGANISM: Homo sapiens

<400> SEQUENCE: 18

Ser His Trp Ala Ala Gly Asp Gly Pro
1               5

<210> SEQ ID NO 19
<211> LENGTH: 9
<212> TYPE: PRT
<213> ORGANISM: Homo sapiens

<400> SEQUENCE: 19

His Trp Ala Ala Gly Asp Gly Pro Thr
1               5

<210> SEQ ID NO 20
<211> LENGTH: 9
<212> TYPE: PRT
<213> ORGANISM: Homo sapiens

<400> SEQUENCE: 20

Trp Ala Ala Gly Asp Gly Pro Thr Gln
1               5

<210> SEQ ID NO 21
<211> LENGTH: 9
<212> TYPE: PRT
<213> ORGANISM: Homo sapiens

<400> SEQUENCE: 21

Ala Ala Gly Asp Gly Pro Thr Gln Glu
1               5
```

<210> SEQ ID NO 22
<211> LENGTH: 9
<212> TYPE: PRT
<213> ORGANISM: Homo sapiens

<400> SEQUENCE: 22

Ala Gly Asp Gly Pro Thr Gln Glu Arg
1               5

<210> SEQ ID NO 23
<211> LENGTH: 9
<212> TYPE: PRT
<213> ORGANISM: Homo sapiens

<400> SEQUENCE: 23

Gly Asp Gly Pro Thr Gln Glu Arg Cys
1               5

<210> SEQ ID NO 24
<211> LENGTH: 9
<212> TYPE: PRT
<213> ORGANISM: Homo sapiens

<400> SEQUENCE: 24

Asp Gly Pro Thr Gln Glu Arg Cys Gly
1               5

<210> SEQ ID NO 25
<211> LENGTH: 9
<212> TYPE: PRT
<213> ORGANISM: Homo sapiens

<400> SEQUENCE: 25

Gly Pro Thr Gln Glu Arg Cys Gly Pro
1               5

<210> SEQ ID NO 26
<211> LENGTH: 9
<212> TYPE: PRT
<213> ORGANISM: Homo sapiens

<400> SEQUENCE: 26

Pro Thr Gln Glu Arg Cys Gly Pro Arg
1               5

<210> SEQ ID NO 27
<211> LENGTH: 9
<212> TYPE: PRT
<213> ORGANISM: Homo sapiens

<400> SEQUENCE: 27

Thr Gln Glu Arg Cys Gly Pro Arg Ser
1               5

<210> SEQ ID NO 28
<211> LENGTH: 9
<212> TYPE: PRT
<213> ORGANISM: Homo sapiens

<400> SEQUENCE: 28

Gln Glu Arg Cys Gly Pro Arg Ser Leu
1               5

<210> SEQ ID NO 29
<211> LENGTH: 9

```
<212> TYPE: PRT
<213> ORGANISM: Homo sapiens

<400> SEQUENCE: 29

Glu Arg Cys Gly Pro Arg Ser Leu Gly
1               5

<210> SEQ ID NO 30
<211> LENGTH: 9
<212> TYPE: PRT
<213> ORGANISM: Homo sapiens

<400> SEQUENCE: 30

Arg Cys Gly Pro Arg Ser Leu Gly Ser
1               5

<210> SEQ ID NO 31
<211> LENGTH: 9
<212> TYPE: PRT
<213> ORGANISM: Homo sapiens

<400> SEQUENCE: 31

Cys Gly Pro Arg Ser Leu Gly Ser Pro
1               5

<210> SEQ ID NO 32
<211> LENGTH: 9
<212> TYPE: PRT
<213> ORGANISM: Homo sapiens

<400> SEQUENCE: 32

Gly Pro Arg Ser Leu Gly Ser Pro Val
1               5

<210> SEQ ID NO 33
<211> LENGTH: 9
<212> TYPE: PRT
<213> ORGANISM: Homo sapiens

<400> SEQUENCE: 33

Pro Arg Ser Leu Gly Ser Pro Val Leu
1               5

<210> SEQ ID NO 34
<211> LENGTH: 9
<212> TYPE: PRT
<213> ORGANISM: Homo sapiens

<400> SEQUENCE: 34

Arg Ser Leu Gly Ser Pro Val Leu Gly
1               5

<210> SEQ ID NO 35
<211> LENGTH: 9
<212> TYPE: PRT
<213> ORGANISM: Homo sapiens

<400> SEQUENCE: 35

Ser Leu Gly Ser Pro Val Leu Gly Leu
1               5

<210> SEQ ID NO 36
<211> LENGTH: 9
<212> TYPE: PRT
<213> ORGANISM: Homo sapiens
```

```
<400> SEQUENCE: 36

Leu Gly Ser Pro Val Leu Gly Leu Asp
1               5

<210> SEQ ID NO 37
<211> LENGTH: 9
<212> TYPE: PRT
<213> ORGANISM: Homo sapiens

<400> SEQUENCE: 37

Gly Ser Pro Val Leu Gly Leu Asp Thr
1               5

<210> SEQ ID NO 38
<211> LENGTH: 9
<212> TYPE: PRT
<213> ORGANISM: Homo sapiens

<400> SEQUENCE: 38

Ser Pro Val Leu Gly Leu Asp Thr Cys
1               5

<210> SEQ ID NO 39
<211> LENGTH: 9
<212> TYPE: PRT
<213> ORGANISM: Homo sapiens

<400> SEQUENCE: 39

Pro Val Leu Gly Leu Asp Thr Cys Arg
1               5

<210> SEQ ID NO 40
<211> LENGTH: 9
<212> TYPE: PRT
<213> ORGANISM: Homo sapiens

<400> SEQUENCE: 40

Val Leu Gly Leu Asp Thr Cys Arg Ala
1               5

<210> SEQ ID NO 41
<211> LENGTH: 9
<212> TYPE: PRT
<213> ORGANISM: Homo sapiens

<400> SEQUENCE: 41

Leu Gly Leu Asp Thr Cys Arg Ala Trp
1               5

<210> SEQ ID NO 42
<211> LENGTH: 9
<212> TYPE: PRT
<213> ORGANISM: Homo sapiens

<400> SEQUENCE: 42

Gly Leu Asp Thr Cys Arg Ala Trp Asp
1               5

<210> SEQ ID NO 43
<211> LENGTH: 9
<212> TYPE: PRT
<213> ORGANISM: Homo sapiens

<400> SEQUENCE: 43
```

```
Leu Asp Thr Cys Arg Ala Trp Asp His
1               5
```

<210> SEQ ID NO 44
<211> LENGTH: 9
<212> TYPE: PRT
<213> ORGANISM: Homo sapiens

<400> SEQUENCE: 44

```
Asp Thr Cys Arg Ala Trp Asp His Val
1               5
```

<210> SEQ ID NO 45
<211> LENGTH: 9
<212> TYPE: PRT
<213> ORGANISM: Homo sapiens

<400> SEQUENCE: 45

```
Thr Cys Arg Ala Trp Asp His Val Asp
1               5
```

<210> SEQ ID NO 46
<211> LENGTH: 9
<212> TYPE: PRT
<213> ORGANISM: Homo sapiens

<400> SEQUENCE: 46

```
Cys Arg Ala Trp Asp His Val Asp Gly
1               5
```

<210> SEQ ID NO 47
<211> LENGTH: 9
<212> TYPE: PRT
<213> ORGANISM: Homo sapiens

<400> SEQUENCE: 47

```
Arg Ala Trp Asp His Val Asp Gly Gln
1               5
```

<210> SEQ ID NO 48
<211> LENGTH: 9
<212> TYPE: PRT
<213> ORGANISM: Homo sapiens

<400> SEQUENCE: 48

```
Ala Trp Asp His Val Asp Gly Gln Ile
1               5
```

<210> SEQ ID NO 49
<211> LENGTH: 9
<212> TYPE: PRT
<213> ORGANISM: Homo sapiens

<400> SEQUENCE: 49

```
Trp Asp His Val Asp Gly Gln Ile Leu
1               5
```

<210> SEQ ID NO 50
<211> LENGTH: 9
<212> TYPE: PRT
<213> ORGANISM: Homo sapiens

<400> SEQUENCE: 50

```
Asp His Val Asp Gly Gln Ile Leu Gly
```

```
1               5
```

<210> SEQ ID NO 51
<211> LENGTH: 9
<212> TYPE: PRT
<213> ORGANISM: Homo sapiens

<400> SEQUENCE: 51

```
His Val Asp Gly Gln Ile Leu Gly Gln
1               5
```

<210> SEQ ID NO 52
<211> LENGTH: 9
<212> TYPE: PRT
<213> ORGANISM: Homo sapiens

<400> SEQUENCE: 52

```
Val Asp Gly Gln Ile Leu Gly Gln Leu
1               5
```

<210> SEQ ID NO 53
<211> LENGTH: 9
<212> TYPE: PRT
<213> ORGANISM: Homo sapiens

<400> SEQUENCE: 53

```
Asp Gly Gln Ile Leu Gly Gln Leu Arg
1               5
```

<210> SEQ ID NO 54
<211> LENGTH: 9
<212> TYPE: PRT
<213> ORGANISM: Homo sapiens

<400> SEQUENCE: 54

```
Gly Gln Ile Leu Gly Gln Leu Arg Pro
1               5
```

<210> SEQ ID NO 55
<211> LENGTH: 9
<212> TYPE: PRT
<213> ORGANISM: Homo sapiens

<400> SEQUENCE: 55

```
Gln Ile Leu Gly Gln Leu Arg Pro Leu
1               5
```

<210> SEQ ID NO 56
<211> LENGTH: 9
<212> TYPE: PRT
<213> ORGANISM: Homo sapiens

<400> SEQUENCE: 56

```
Ile Leu Gly Gln Leu Arg Pro Leu Thr
1               5
```

<210> SEQ ID NO 57
<211> LENGTH: 9
<212> TYPE: PRT
<213> ORGANISM: Homo sapiens

<400> SEQUENCE: 57

```
Leu Gly Gln Leu Arg Pro Leu Thr Glu
1               5
```

<210> SEQ ID NO 58
<211> LENGTH: 9
<212> TYPE: PRT
<213> ORGANISM: Homo sapiens

<400> SEQUENCE: 58

Gly Gln Leu Arg Pro Leu Thr Glu Glu
1               5

<210> SEQ ID NO 59
<211> LENGTH: 9
<212> TYPE: PRT
<213> ORGANISM: Homo sapiens

<400> SEQUENCE: 59

Gln Leu Arg Pro Leu Thr Glu Glu Glu
1               5

<210> SEQ ID NO 60
<211> LENGTH: 9
<212> TYPE: PRT
<213> ORGANISM: Homo sapiens

<400> SEQUENCE: 60

Leu Arg Pro Leu Thr Glu Glu Glu Glu
1               5

<210> SEQ ID NO 61
<211> LENGTH: 9
<212> TYPE: PRT
<213> ORGANISM: Homo sapiens

<400> SEQUENCE: 61

Arg Pro Leu Thr Glu Glu Glu Glu Glu
1               5

<210> SEQ ID NO 62
<211> LENGTH: 9
<212> TYPE: PRT
<213> ORGANISM: Homo sapiens

<400> SEQUENCE: 62

Pro Leu Thr Glu Glu Glu Glu Glu Glu
1               5

<210> SEQ ID NO 63
<211> LENGTH: 9
<212> TYPE: PRT
<213> ORGANISM: Homo sapiens

<400> SEQUENCE: 63

Leu Thr Glu Glu Glu Glu Glu Glu Gly
1               5

<210> SEQ ID NO 64
<211> LENGTH: 9
<212> TYPE: PRT
<213> ORGANISM: Homo sapiens

<400> SEQUENCE: 64

Thr Glu Glu Glu Glu Glu Glu Gly Ala
1               5

<210> SEQ ID NO 65

```
<211> LENGTH: 9
<212> TYPE: PRT
<213> ORGANISM: Homo sapiens

<400> SEQUENCE: 65

Glu Glu Glu Glu Glu Gly Ala Gly
1               5

<210> SEQ ID NO 66
<211> LENGTH: 9
<212> TYPE: PRT
<213> ORGANISM: Homo sapiens

<400> SEQUENCE: 66

Glu Glu Glu Glu Gly Ala Gly Ala
1               5

<210> SEQ ID NO 67
<211> LENGTH: 9
<212> TYPE: PRT
<213> ORGANISM: Homo sapiens

<400> SEQUENCE: 67

Glu Glu Glu Gly Ala Gly Ala Thr
1               5

<210> SEQ ID NO 68
<211> LENGTH: 9
<212> TYPE: PRT
<213> ORGANISM: Homo sapiens

<400> SEQUENCE: 68

Glu Glu Gly Ala Gly Ala Thr Leu
1               5

<210> SEQ ID NO 69
<211> LENGTH: 9
<212> TYPE: PRT
<213> ORGANISM: Homo sapiens

<400> SEQUENCE: 69

Glu Gly Ala Gly Ala Thr Leu Ser
1               5

<210> SEQ ID NO 70
<211> LENGTH: 9
<212> TYPE: PRT
<213> ORGANISM: Homo sapiens

<400> SEQUENCE: 70

Glu Gly Ala Gly Ala Thr Leu Ser Arg
1               5

<210> SEQ ID NO 71
<211> LENGTH: 9
<212> TYPE: PRT
<213> ORGANISM: Homo sapiens

<400> SEQUENCE: 71

Gly Ala Gly Ala Thr Leu Ser Arg Gly
1               5

<210> SEQ ID NO 72
<211> LENGTH: 9
<212> TYPE: PRT
```

<213> ORGANISM: Homo sapiens

<400> SEQUENCE: 72

Ala Gly Ala Thr Leu Ser Arg Gly Pro
1               5

<210> SEQ ID NO 73
<211> LENGTH: 9
<212> TYPE: PRT
<213> ORGANISM: Homo sapiens

<400> SEQUENCE: 73

Gly Ala Thr Leu Ser Arg Gly Pro Ala
1               5

<210> SEQ ID NO 74
<211> LENGTH: 9
<212> TYPE: PRT
<213> ORGANISM: Homo sapiens

<400> SEQUENCE: 74

Ala Thr Leu Ser Arg Gly Pro Ala Phe
1               5

<210> SEQ ID NO 75
<211> LENGTH: 9
<212> TYPE: PRT
<213> ORGANISM: Homo sapiens

<400> SEQUENCE: 75

Thr Leu Ser Arg Gly Pro Ala Phe Pro
1               5

<210> SEQ ID NO 76
<211> LENGTH: 9
<212> TYPE: PRT
<213> ORGANISM: Homo sapiens

<400> SEQUENCE: 76

Leu Ser Arg Gly Pro Ala Phe Pro Gly
1               5

<210> SEQ ID NO 77
<211> LENGTH: 9
<212> TYPE: PRT
<213> ORGANISM: Homo sapiens

<400> SEQUENCE: 77

Ser Arg Gly Pro Ala Phe Pro Gly Met
1               5

<210> SEQ ID NO 78
<211> LENGTH: 9
<212> TYPE: PRT
<213> ORGANISM: Homo sapiens

<400> SEQUENCE: 78

Arg Gly Pro Ala Phe Pro Gly Met Gly
1               5

<210> SEQ ID NO 79
<211> LENGTH: 9
<212> TYPE: PRT
<213> ORGANISM: Homo sapiens

```
<400> SEQUENCE: 79

Gly Pro Ala Phe Pro Gly Met Gly Ser
1               5

<210> SEQ ID NO 80
<211> LENGTH: 9
<212> TYPE: PRT
<213> ORGANISM: Homo sapiens

<400> SEQUENCE: 80

Pro Ala Phe Pro Gly Met Gly Ser Glu
1               5

<210> SEQ ID NO 81
<211> LENGTH: 9
<212> TYPE: PRT
<213> ORGANISM: Homo sapiens

<400> SEQUENCE: 81

Ala Phe Pro Gly Met Gly Ser Glu Glu
1               5

<210> SEQ ID NO 82
<211> LENGTH: 9
<212> TYPE: PRT
<213> ORGANISM: Homo sapiens

<400> SEQUENCE: 82

Phe Pro Gly Met Gly Ser Glu Glu Leu
1               5

<210> SEQ ID NO 83
<211> LENGTH: 9
<212> TYPE: PRT
<213> ORGANISM: Homo sapiens

<400> SEQUENCE: 83

Pro Gly Met Gly Ser Glu Glu Leu Arg
1               5

<210> SEQ ID NO 84
<211> LENGTH: 9
<212> TYPE: PRT
<213> ORGANISM: Homo sapiens

<400> SEQUENCE: 84

Gly Met Gly Ser Glu Glu Leu Arg Leu
1               5

<210> SEQ ID NO 85
<211> LENGTH: 9
<212> TYPE: PRT
<213> ORGANISM: Homo sapiens

<400> SEQUENCE: 85

Met Gly Ser Glu Glu Leu Arg Leu Ala
1               5

<210> SEQ ID NO 86
<211> LENGTH: 9
<212> TYPE: PRT
<213> ORGANISM: Homo sapiens

<400> SEQUENCE: 86
```

Gly Ser Glu Glu Leu Arg Leu Ala Ser
1               5

<210> SEQ ID NO 87
<211> LENGTH: 9
<212> TYPE: PRT
<213> ORGANISM: Homo sapiens

<400> SEQUENCE: 87

Ser Glu Glu Leu Arg Leu Ala Ser Phe
1               5

<210> SEQ ID NO 88
<211> LENGTH: 9
<212> TYPE: PRT
<213> ORGANISM: Homo sapiens

<400> SEQUENCE: 88

Glu Glu Leu Arg Leu Ala Ser Phe Tyr
1               5

<210> SEQ ID NO 89
<211> LENGTH: 9
<212> TYPE: PRT
<213> ORGANISM: Homo sapiens

<400> SEQUENCE: 89

Glu Leu Arg Leu Ala Ser Phe Tyr Asp
1               5

<210> SEQ ID NO 90
<211> LENGTH: 9
<212> TYPE: PRT
<213> ORGANISM: Homo sapiens

<400> SEQUENCE: 90

Leu Arg Leu Ala Ser Phe Tyr Asp Trp
1               5

<210> SEQ ID NO 91
<211> LENGTH: 9
<212> TYPE: PRT
<213> ORGANISM: Homo sapiens

<400> SEQUENCE: 91

Arg Leu Ala Ser Phe Tyr Asp Trp Pro
1               5

<210> SEQ ID NO 92
<211> LENGTH: 9
<212> TYPE: PRT
<213> ORGANISM: Homo sapiens

<400> SEQUENCE: 92

Leu Ala Ser Phe Tyr Asp Trp Pro Leu
1               5

<210> SEQ ID NO 93
<211> LENGTH: 9
<212> TYPE: PRT
<213> ORGANISM: Homo sapiens

<400> SEQUENCE: 93

Ala Ser Phe Tyr Asp Trp Pro Leu Thr
1               5

-continued

<210> SEQ ID NO 94
<211> LENGTH: 9
<212> TYPE: PRT
<213> ORGANISM: Homo sapiens

<400> SEQUENCE: 94

Ser Phe Tyr Asp Trp Pro Leu Thr Ala
1               5

<210> SEQ ID NO 95
<211> LENGTH: 9
<212> TYPE: PRT
<213> ORGANISM: Homo sapiens

<400> SEQUENCE: 95

Phe Tyr Asp Trp Pro Leu Thr Ala Glu
1               5

<210> SEQ ID NO 96
<211> LENGTH: 9
<212> TYPE: PRT
<213> ORGANISM: Homo sapiens

<400> SEQUENCE: 96

Tyr Asp Trp Pro Leu Thr Ala Glu Val
1               5

<210> SEQ ID NO 97
<211> LENGTH: 9
<212> TYPE: PRT
<213> ORGANISM: Homo sapiens

<400> SEQUENCE: 97

Asp Trp Pro Leu Thr Ala Glu Val Pro
1               5

<210> SEQ ID NO 98
<211> LENGTH: 9
<212> TYPE: PRT
<213> ORGANISM: Homo sapiens

<400> SEQUENCE: 98

Trp Pro Leu Thr Ala Glu Val Pro Pro
1               5

<210> SEQ ID NO 99
<211> LENGTH: 9
<212> TYPE: PRT
<213> ORGANISM: Homo sapiens

<400> SEQUENCE: 99

Pro Leu Thr Ala Glu Val Pro Pro Glu
1               5

<210> SEQ ID NO 100
<211> LENGTH: 9
<212> TYPE: PRT
<213> ORGANISM: Homo sapiens

<400> SEQUENCE: 100

Leu Thr Ala Glu Val Pro Pro Glu Leu
1               5

```
<210> SEQ ID NO 101
<211> LENGTH: 9
<212> TYPE: PRT
<213> ORGANISM: Homo sapiens

<400> SEQUENCE: 101

Thr Ala Glu Val Pro Pro Glu Leu Leu
1               5

<210> SEQ ID NO 102
<211> LENGTH: 9
<212> TYPE: PRT
<213> ORGANISM: Homo sapiens

<400> SEQUENCE: 102

Ala Glu Val Pro Pro Glu Leu Leu Ala
1               5

<210> SEQ ID NO 103
<211> LENGTH: 9
<212> TYPE: PRT
<213> ORGANISM: Homo sapiens

<400> SEQUENCE: 103

Glu Val Pro Pro Glu Leu Leu Ala Ala
1               5

<210> SEQ ID NO 104
<211> LENGTH: 9
<212> TYPE: PRT
<213> ORGANISM: Homo sapiens

<400> SEQUENCE: 104

Val Pro Pro Glu Leu Leu Ala Ala Ala
1               5

<210> SEQ ID NO 105
<211> LENGTH: 9
<212> TYPE: PRT
<213> ORGANISM: Homo sapiens

<400> SEQUENCE: 105

Pro Pro Glu Leu Leu Ala Ala Ala Gly
1               5

<210> SEQ ID NO 106
<211> LENGTH: 8
<212> TYPE: PRT
<213> ORGANISM: Homo sapiens

<400> SEQUENCE: 106

Pro Glu Leu Ala Ala Ala Gly Phe
1               5

<210> SEQ ID NO 107
<211> LENGTH: 9
<212> TYPE: PRT
<213> ORGANISM: Homo sapiens

<400> SEQUENCE: 107

Glu Leu Leu Ala Ala Ala Gly Phe Phe
1               5

<210> SEQ ID NO 108
<211> LENGTH: 9
```

```
<212> TYPE: PRT
<213> ORGANISM: Homo sapiens

<400> SEQUENCE: 108

Leu Leu Ala Ala Ala Gly Phe Phe His
1               5

<210> SEQ ID NO 109
<211> LENGTH: 9
<212> TYPE: PRT
<213> ORGANISM: Homo sapiens

<400> SEQUENCE: 109

Leu Ala Ala Ala Gly Phe Phe His Thr
1               5

<210> SEQ ID NO 110
<211> LENGTH: 9
<212> TYPE: PRT
<213> ORGANISM: Homo sapiens

<400> SEQUENCE: 110

Ala Ala Ala Gly Phe Phe His Thr Gly
1               5

<210> SEQ ID NO 111
<211> LENGTH: 9
<212> TYPE: PRT
<213> ORGANISM: Homo sapiens

<400> SEQUENCE: 111

Ala Ala Gly Phe Phe His Thr Gly His
1               5

<210> SEQ ID NO 112
<211> LENGTH: 9
<212> TYPE: PRT
<213> ORGANISM: Homo sapiens

<400> SEQUENCE: 112

Ala Gly Phe Phe His Thr Gly His Gln
1               5

<210> SEQ ID NO 113
<211> LENGTH: 9
<212> TYPE: PRT
<213> ORGANISM: Homo sapiens

<400> SEQUENCE: 113

Gly Phe Phe His Thr Gly His Gln Asp
1               5

<210> SEQ ID NO 114
<211> LENGTH: 9
<212> TYPE: PRT
<213> ORGANISM: Homo sapiens

<400> SEQUENCE: 114

Phe Phe His Thr Gly His Gln Asp Lys
1               5

<210> SEQ ID NO 115
<211> LENGTH: 9
<212> TYPE: PRT
<213> ORGANISM: Homo sapiens
```

```
<400> SEQUENCE: 115

Phe His Thr Gly His Gln Asp Lys Val
1               5

<210> SEQ ID NO 116
<211> LENGTH: 9
<212> TYPE: PRT
<213> ORGANISM: Homo sapiens

<400> SEQUENCE: 116

His Thr Gly His Gln Asp Lys Val Arg
1               5

<210> SEQ ID NO 117
<211> LENGTH: 9
<212> TYPE: PRT
<213> ORGANISM: Homo sapiens

<400> SEQUENCE: 117

Thr Gly His Gln Asp Lys Val Arg Cys
1               5

<210> SEQ ID NO 118
<211> LENGTH: 9
<212> TYPE: PRT
<213> ORGANISM: Homo sapiens

<400> SEQUENCE: 118

Gly His Gln Asp Lys Val Arg Cys Phe
1               5

<210> SEQ ID NO 119
<211> LENGTH: 9
<212> TYPE: PRT
<213> ORGANISM: Homo sapiens

<400> SEQUENCE: 119

His Gln Asp Lys Val Arg Cys Phe Phe
1               5

<210> SEQ ID NO 120
<211> LENGTH: 9
<212> TYPE: PRT
<213> ORGANISM: Homo sapiens

<400> SEQUENCE: 120

Gln Asp Lys Val Arg Cys Phe Phe Cys
1               5

<210> SEQ ID NO 121
<211> LENGTH: 9
<212> TYPE: PRT
<213> ORGANISM: Homo sapiens

<400> SEQUENCE: 121

Asp Lys Val Arg Cys Phe Phe Cys Tyr
1               5

<210> SEQ ID NO 122
<211> LENGTH: 9
<212> TYPE: PRT
<213> ORGANISM: Homo sapiens

<400> SEQUENCE: 122
```

```
Lys Val Arg Cys Phe Phe Cys Tyr Gly
1               5
```

<210> SEQ ID NO 123
<211> LENGTH: 9
<212> TYPE: PRT
<213> ORGANISM: Homo sapiens

<400> SEQUENCE: 123

```
Val Arg Cys Phe Phe Cys Tyr Gly Gly
1               5
```

<210> SEQ ID NO 124
<211> LENGTH: 9
<212> TYPE: PRT
<213> ORGANISM: Homo sapiens

<400> SEQUENCE: 124

```
Arg Cys Phe Phe Cys Tyr Gly Gly Leu
1               5
```

<210> SEQ ID NO 125
<211> LENGTH: 9
<212> TYPE: PRT
<213> ORGANISM: Homo sapiens

<400> SEQUENCE: 125

```
Cys Phe Phe Cys Tyr Gly Gly Leu Gln
1               5
```

<210> SEQ ID NO 126
<211> LENGTH: 9
<212> TYPE: PRT
<213> ORGANISM: Homo sapiens

<400> SEQUENCE: 126

```
Phe Phe Cys Tyr Gly Gly Leu Gln Ser
1               5
```

<210> SEQ ID NO 127
<211> LENGTH: 9
<212> TYPE: PRT
<213> ORGANISM: Homo sapiens

<400> SEQUENCE: 127

```
Phe Cys Tyr Gly Gly Leu Gln Ser Trp
1               5
```

<210> SEQ ID NO 128
<211> LENGTH: 9
<212> TYPE: PRT
<213> ORGANISM: Homo sapiens

<400> SEQUENCE: 128

```
Cys Tyr Gly Gly Leu Gln Ser Trp Lys
1               5
```

<210> SEQ ID NO 129
<211> LENGTH: 9
<212> TYPE: PRT
<213> ORGANISM: Homo sapiens

<400> SEQUENCE: 129

```
Tyr Gly Gly Leu Gln Ser Trp Lys Arg
```

<210> SEQ ID NO 130
<211> LENGTH: 9
<212> TYPE: PRT
<213> ORGANISM: Homo sapiens

<400> SEQUENCE: 130

Gly Gly Leu Gln Ser Trp Lys Arg Gly
1               5

<210> SEQ ID NO 131
<211> LENGTH: 9
<212> TYPE: PRT
<213> ORGANISM: Homo sapiens

<400> SEQUENCE: 131

Gly Leu Gln Ser Trp Lys Arg Gly Asp
1               5

<210> SEQ ID NO 132
<211> LENGTH: 9
<212> TYPE: PRT
<213> ORGANISM: Homo sapiens

<400> SEQUENCE: 132

Leu Gln Ser Trp Lys Arg Gly Asp Asp
1               5

<210> SEQ ID NO 133
<211> LENGTH: 9
<212> TYPE: PRT
<213> ORGANISM: Homo sapiens

<400> SEQUENCE: 133

Gln Ser Trp Lys Arg Gly Asp Asp Pro
1               5

<210> SEQ ID NO 134
<211> LENGTH: 9
<212> TYPE: PRT
<213> ORGANISM: Homo sapiens

<400> SEQUENCE: 134

Ser Trp Lys Arg Gly Asp Asp Pro Trp
1               5

<210> SEQ ID NO 135
<211> LENGTH: 9
<212> TYPE: PRT
<213> ORGANISM: Homo sapiens

<400> SEQUENCE: 135

Trp Lys Arg Gly Asp Asp Pro Trp Thr
1               5

<210> SEQ ID NO 136
<211> LENGTH: 9
<212> TYPE: PRT
<213> ORGANISM: Homo sapiens

<400> SEQUENCE: 136

Lys Arg Gly Asp Asp Pro Trp Thr His
1               5

```
<210> SEQ ID NO 137
<211> LENGTH: 9
<212> TYPE: PRT
<213> ORGANISM: Homo sapiens

<400> SEQUENCE: 137

Arg Gly Asp Asp Pro Trp Thr His Ala
1               5

<210> SEQ ID NO 138
<211> LENGTH: 9
<212> TYPE: PRT
<213> ORGANISM: Homo sapiens

<400> SEQUENCE: 138

Gly Asp Asp Pro Trp Thr His Ala Lys
1               5

<210> SEQ ID NO 139
<211> LENGTH: 9
<212> TYPE: PRT
<213> ORGANISM: Homo sapiens

<400> SEQUENCE: 139

Asp Asp Pro Trp Thr His Ala Lys Trp
1               5

<210> SEQ ID NO 140
<211> LENGTH: 9
<212> TYPE: PRT
<213> ORGANISM: Homo sapiens

<400> SEQUENCE: 140

Asp Pro Trp Thr His Ala Lys Trp Phe
1               5

<210> SEQ ID NO 141
<211> LENGTH: 9
<212> TYPE: PRT
<213> ORGANISM: Homo sapiens

<400> SEQUENCE: 141

Pro Trp Thr His Ala Lys Trp Phe Pro
1               5

<210> SEQ ID NO 142
<211> LENGTH: 9
<212> TYPE: PRT
<213> ORGANISM: Homo sapiens

<400> SEQUENCE: 142

Trp Thr His Ala Lys Trp Phe Pro Ser
1               5

<210> SEQ ID NO 143
<211> LENGTH: 9
<212> TYPE: PRT
<213> ORGANISM: Homo sapiens

<400> SEQUENCE: 143

Thr His Ala Lys Trp Phe Pro Ser Cys
1               5

<210> SEQ ID NO 144
```

```
<211> LENGTH: 9
<212> TYPE: PRT
<213> ORGANISM: Homo sapiens

<400> SEQUENCE: 144

His Ala Lys Trp Phe Pro Ser Cys Gln
1               5

<210> SEQ ID NO 145
<211> LENGTH: 9
<212> TYPE: PRT
<213> ORGANISM: Homo sapiens

<400> SEQUENCE: 145

Ala Lys Trp Phe Pro Ser Cys Gln Phe
1               5

<210> SEQ ID NO 146
<211> LENGTH: 9
<212> TYPE: PRT
<213> ORGANISM: Homo sapiens

<400> SEQUENCE: 146

Lys Trp Phe Pro Ser Cys Gln Phe Leu
1               5

<210> SEQ ID NO 147
<211> LENGTH: 9
<212> TYPE: PRT
<213> ORGANISM: Homo sapiens

<400> SEQUENCE: 147

Trp Phe Pro Ser Cys Gln Phe Leu Leu
1               5

<210> SEQ ID NO 148
<211> LENGTH: 9
<212> TYPE: PRT
<213> ORGANISM: Homo sapiens

<400> SEQUENCE: 148

Phe Pro Ser Cys Gln Phe Leu Leu Arg
1               5

<210> SEQ ID NO 149
<211> LENGTH: 9
<212> TYPE: PRT
<213> ORGANISM: Homo sapiens

<400> SEQUENCE: 149

Pro Ser Cys Gln Phe Leu Leu Arg Ser
1               5

<210> SEQ ID NO 150
<211> LENGTH: 9
<212> TYPE: PRT
<213> ORGANISM: Homo sapiens

<400> SEQUENCE: 150

Ser Cys Gln Phe Leu Leu Arg Ser Lys
1               5

<210> SEQ ID NO 151
<211> LENGTH: 9
<212> TYPE: PRT
```

<213> ORGANISM: Homo sapiens

<400> SEQUENCE: 151

Cys Gln Phe Leu Leu Arg Ser Lys Gly
1               5

<210> SEQ ID NO 152
<211> LENGTH: 9
<212> TYPE: PRT
<213> ORGANISM: Homo sapiens

<400> SEQUENCE: 152

Gln Phe Leu Leu Arg Ser Lys Gly Arg
1               5

<210> SEQ ID NO 153
<211> LENGTH: 9
<212> TYPE: PRT
<213> ORGANISM: Homo sapiens

<400> SEQUENCE: 153

Phe Leu Leu Arg Ser Lys Gly Arg Asp
1               5

<210> SEQ ID NO 154
<211> LENGTH: 9
<212> TYPE: PRT
<213> ORGANISM: Homo sapiens

<400> SEQUENCE: 154

Leu Leu Arg Ser Lys Gly Arg Asp Phe
1               5

<210> SEQ ID NO 155
<211> LENGTH: 9
<212> TYPE: PRT
<213> ORGANISM: Homo sapiens

<400> SEQUENCE: 155

Leu Arg Ser Lys Gly Arg Asp Phe Val
1               5

<210> SEQ ID NO 156
<211> LENGTH: 9
<212> TYPE: PRT
<213> ORGANISM: Homo sapiens

<400> SEQUENCE: 156

Arg Ser Lys Gly Arg Asp Phe Val His
1               5

<210> SEQ ID NO 157
<211> LENGTH: 9
<212> TYPE: PRT
<213> ORGANISM: Homo sapiens

<400> SEQUENCE: 157

Ser Lys Gly Arg Asp Phe Val His Ser
1               5

<210> SEQ ID NO 158
<211> LENGTH: 9
<212> TYPE: PRT
<213> ORGANISM: Homo sapiens

<400> SEQUENCE: 158

Lys Gly Arg Asp Phe Val His Ser Val
1               5

<210> SEQ ID NO 159
<211> LENGTH: 9
<212> TYPE: PRT
<213> ORGANISM: Homo sapiens

<400> SEQUENCE: 159

Gly Arg Asp Phe Val His Ser Val Gln
1               5

<210> SEQ ID NO 160
<211> LENGTH: 9
<212> TYPE: PRT
<213> ORGANISM: Homo sapiens

<400> SEQUENCE: 160

Arg Asp Phe Val His Ser Val Gln Glu
1               5

<210> SEQ ID NO 161
<211> LENGTH: 9
<212> TYPE: PRT
<213> ORGANISM: Homo sapiens

<400> SEQUENCE: 161

Asp Phe Val His Ser Val Gln Glu Thr
1               5

<210> SEQ ID NO 162
<211> LENGTH: 9
<212> TYPE: PRT
<213> ORGANISM: Homo sapiens

<400> SEQUENCE: 162

Phe Val His Ser Val Gln Glu Thr His
1               5

<210> SEQ ID NO 163
<211> LENGTH: 9
<212> TYPE: PRT
<213> ORGANISM: Homo sapiens

<400> SEQUENCE: 163

Val His Ser Val Gln Glu Thr His Ser
1               5

<210> SEQ ID NO 164
<211> LENGTH: 9
<212> TYPE: PRT
<213> ORGANISM: Homo sapiens

<400> SEQUENCE: 164

His Ser Val Gln Glu Thr His Ser Gln
1               5

<210> SEQ ID NO 165
<211> LENGTH: 9
<212> TYPE: PRT
<213> ORGANISM: Homo sapiens

<400> SEQUENCE: 165

```
Ser Val Gln Glu Thr His Ser Gln Leu
1               5
```

```
<210> SEQ ID NO 166
<211> LENGTH: 9
<212> TYPE: PRT
<213> ORGANISM: Homo sapiens

<400> SEQUENCE: 166

Val Gln Glu Thr His Ser Gln Leu Leu
1               5
```

```
<210> SEQ ID NO 167
<211> LENGTH: 9
<212> TYPE: PRT
<213> ORGANISM: Homo sapiens

<400> SEQUENCE: 167

Gln Glu Thr His Ser Gln Leu Leu Gly
1               5
```

```
<210> SEQ ID NO 168
<211> LENGTH: 9
<212> TYPE: PRT
<213> ORGANISM: Homo sapiens

<400> SEQUENCE: 168

Glu Thr His Ser Gln Leu Leu Gly Ser
1               5
```

```
<210> SEQ ID NO 169
<211> LENGTH: 9
<212> TYPE: PRT
<213> ORGANISM: Homo sapiens

<400> SEQUENCE: 169

Thr His Ser Gln Leu Leu Gly Ser Trp
1               5
```

```
<210> SEQ ID NO 170
<211> LENGTH: 9
<212> TYPE: PRT
<213> ORGANISM: Homo sapiens

<400> SEQUENCE: 170

His Ser Gln Leu Leu Gly Ser Trp Asp
1               5
```

```
<210> SEQ ID NO 171
<211> LENGTH: 9
<212> TYPE: PRT
<213> ORGANISM: Homo sapiens

<400> SEQUENCE: 171

Ser Gln Leu Leu Gly Ser Trp Asp Pro
1               5
```

```
<210> SEQ ID NO 172
<211> LENGTH: 9
<212> TYPE: PRT
<213> ORGANISM: Homo sapiens

<400> SEQUENCE: 172

Gln Leu Leu Gly Ser Trp Asp Pro Trp
1               5
```

<210> SEQ ID NO 173
<211> LENGTH: 9
<212> TYPE: PRT
<213> ORGANISM: Homo sapiens

<400> SEQUENCE: 173

Leu Leu Gly Ser Trp Asp Pro Trp Glu
1               5

<210> SEQ ID NO 174
<211> LENGTH: 9
<212> TYPE: PRT
<213> ORGANISM: Homo sapiens

<400> SEQUENCE: 174

Leu Gly Ser Trp Asp Pro Trp Glu Glu
1               5

<210> SEQ ID NO 175
<211> LENGTH: 9
<212> TYPE: PRT
<213> ORGANISM: Homo sapiens

<400> SEQUENCE: 175

Gly Ser Trp Asp Pro Trp Glu Glu Pro
1               5

<210> SEQ ID NO 176
<211> LENGTH: 9
<212> TYPE: PRT
<213> ORGANISM: Homo sapiens

<400> SEQUENCE: 176

Ser Trp Asp Pro Trp Glu Glu Pro Glu
1               5

<210> SEQ ID NO 177
<211> LENGTH: 9
<212> TYPE: PRT
<213> ORGANISM: Homo sapiens

<400> SEQUENCE: 177

Trp Asp Pro Trp Glu Glu Pro Glu Asp
1               5

<210> SEQ ID NO 178
<211> LENGTH: 9
<212> TYPE: PRT
<213> ORGANISM: Homo sapiens

<400> SEQUENCE: 178

Asp Pro Trp Glu Glu Pro Glu Asp Ala
1               5

<210> SEQ ID NO 179
<211> LENGTH: 9
<212> TYPE: PRT
<213> ORGANISM: Homo sapiens

<400> SEQUENCE: 179

Pro Trp Glu Glu Pro Glu Asp Ala Ala
1               5

```
<210> SEQ ID NO 180
<211> LENGTH: 9
<212> TYPE: PRT
<213> ORGANISM: Homo sapiens

<400> SEQUENCE: 180

Trp Glu Glu Pro Glu Asp Ala Ala Pro
1               5

<210> SEQ ID NO 181
<211> LENGTH: 9
<212> TYPE: PRT
<213> ORGANISM: Homo sapiens

<400> SEQUENCE: 181

Glu Glu Pro Glu Asp Ala Ala Pro Val
1               5

<210> SEQ ID NO 182
<211> LENGTH: 9
<212> TYPE: PRT
<213> ORGANISM: Homo sapiens

<400> SEQUENCE: 182

Glu Pro Glu Asp Ala Ala Pro Val Ala
1               5

<210> SEQ ID NO 183
<211> LENGTH: 9
<212> TYPE: PRT
<213> ORGANISM: Homo sapiens

<400> SEQUENCE: 183

Pro Glu Asp Ala Ala Pro Val Ala Pro
1               5

<210> SEQ ID NO 184
<211> LENGTH: 9
<212> TYPE: PRT
<213> ORGANISM: Homo sapiens

<400> SEQUENCE: 184

Glu Asp Ala Ala Pro Val Ala Pro Ser
1               5

<210> SEQ ID NO 185
<211> LENGTH: 9
<212> TYPE: PRT
<213> ORGANISM: Homo sapiens

<400> SEQUENCE: 185

Asp Ala Ala Pro Val Ala Pro Ser Val
1               5

<210> SEQ ID NO 186
<211> LENGTH: 9
<212> TYPE: PRT
<213> ORGANISM: Homo sapiens

<400> SEQUENCE: 186

Ala Ala Pro Val Ala Pro Ser Val Pro
1               5

<210> SEQ ID NO 187
<211> LENGTH: 9
```

```
<212> TYPE: PRT
<213> ORGANISM: Homo sapiens

<400> SEQUENCE: 187

Ala Pro Val Ala Pro Ser Val Pro Ala
1               5

<210> SEQ ID NO 188
<211> LENGTH: 9
<212> TYPE: PRT
<213> ORGANISM: Homo sapiens

<400> SEQUENCE: 188

Pro Val Ala Pro Ser Val Pro Ala Ser
1               5

<210> SEQ ID NO 189
<211> LENGTH: 9
<212> TYPE: PRT
<213> ORGANISM: Homo sapiens

<400> SEQUENCE: 189

Val Ala Pro Ser Val Pro Ala Ser Gly
1               5

<210> SEQ ID NO 190
<211> LENGTH: 9
<212> TYPE: PRT
<213> ORGANISM: Homo sapiens

<400> SEQUENCE: 190

Ala Pro Ser Val Pro Ala Ser Gly Tyr
1               5

<210> SEQ ID NO 191
<211> LENGTH: 9
<212> TYPE: PRT
<213> ORGANISM: Homo sapiens

<400> SEQUENCE: 191

Pro Ser Val Pro Ala Ser Gly Tyr Pro
1               5

<210> SEQ ID NO 192
<211> LENGTH: 9
<212> TYPE: PRT
<213> ORGANISM: Homo sapiens

<400> SEQUENCE: 192

Ser Val Pro Ala Ser Gly Tyr Pro Glu
1               5

<210> SEQ ID NO 193
<211> LENGTH: 9
<212> TYPE: PRT
<213> ORGANISM: Homo sapiens

<400> SEQUENCE: 193

Val Pro Ala Ser Gly Tyr Pro Glu Leu
1               5

<210> SEQ ID NO 194
<211> LENGTH: 9
<212> TYPE: PRT
<213> ORGANISM: Homo sapiens
```

```
<400> SEQUENCE: 194

Pro Ala Ser Gly Tyr Pro Glu Leu Pro
1               5

<210> SEQ ID NO 195
<211> LENGTH: 9
<212> TYPE: PRT
<213> ORGANISM: Homo sapiens

<400> SEQUENCE: 195

Ala Ser Gly Tyr Pro Glu Leu Pro Thr
1               5

<210> SEQ ID NO 196
<211> LENGTH: 9
<212> TYPE: PRT
<213> ORGANISM: Homo sapiens

<400> SEQUENCE: 196

Ser Gly Tyr Pro Glu Leu Pro Thr Pro
1               5

<210> SEQ ID NO 197
<211> LENGTH: 9
<212> TYPE: PRT
<213> ORGANISM: Homo sapiens

<400> SEQUENCE: 197

Gly Tyr Pro Glu Leu Pro Thr Pro Arg
1               5

<210> SEQ ID NO 198
<211> LENGTH: 9
<212> TYPE: PRT
<213> ORGANISM: Homo sapiens

<400> SEQUENCE: 198

Tyr Pro Glu Leu Pro Thr Pro Arg Arg
1               5

<210> SEQ ID NO 199
<211> LENGTH: 9
<212> TYPE: PRT
<213> ORGANISM: Homo sapiens

<400> SEQUENCE: 199

Pro Glu Leu Pro Thr Pro Arg Arg Glu
1               5

<210> SEQ ID NO 200
<211> LENGTH: 9
<212> TYPE: PRT
<213> ORGANISM: Homo sapiens

<400> SEQUENCE: 200

Glu Leu Pro Thr Pro Arg Arg Glu Val
1               5

<210> SEQ ID NO 201
<211> LENGTH: 9
<212> TYPE: PRT
<213> ORGANISM: Homo sapiens

<400> SEQUENCE: 201
```

```
Leu Pro Thr Pro Arg Arg Glu Val Gln
1               5
```

<210> SEQ ID NO 202
<211> LENGTH: 9
<212> TYPE: PRT
<213> ORGANISM: Homo sapiens

<400> SEQUENCE: 202

```
Pro Thr Pro Arg Arg Glu Val Gln Ser
1               5
```

<210> SEQ ID NO 203
<211> LENGTH: 9
<212> TYPE: PRT
<213> ORGANISM: Homo sapiens

<400> SEQUENCE: 203

```
Thr Pro Arg Arg Glu Val Gln Ser Glu
1               5
```

<210> SEQ ID NO 204
<211> LENGTH: 9
<212> TYPE: PRT
<213> ORGANISM: Homo sapiens

<400> SEQUENCE: 204

```
Pro Arg Arg Glu Val Gln Ser Glu Ser
1               5
```

<210> SEQ ID NO 205
<211> LENGTH: 9
<212> TYPE: PRT
<213> ORGANISM: Homo sapiens

<400> SEQUENCE: 205

```
Arg Arg Glu Val Gln Ser Glu Ser Ala
1               5
```

<210> SEQ ID NO 206
<211> LENGTH: 9
<212> TYPE: PRT
<213> ORGANISM: Homo sapiens

<400> SEQUENCE: 206

```
Arg Glu Val Gln Ser Glu Ser Ala Gln
1               5
```

<210> SEQ ID NO 207
<211> LENGTH: 9
<212> TYPE: PRT
<213> ORGANISM: Homo sapiens

<400> SEQUENCE: 207

```
Glu Val Gln Ser Glu Ser Ala Gln Glu
1               5
```

<210> SEQ ID NO 208
<211> LENGTH: 9
<212> TYPE: PRT
<213> ORGANISM: Homo sapiens

<400> SEQUENCE: 208

```
Val Gln Ser Glu Ser Ala Gln Glu Pro
```

```
1               5
```

<210> SEQ ID NO 209
<211> LENGTH: 9
<212> TYPE: PRT
<213> ORGANISM: Homo sapiens

<400> SEQUENCE: 209

```
Gln Ser Glu Ser Ala Gln Glu Pro Gly
1               5
```

<210> SEQ ID NO 210
<211> LENGTH: 9
<212> TYPE: PRT
<213> ORGANISM: Homo sapiens

<400> SEQUENCE: 210

```
Ser Glu Ser Ala Gln Glu Pro Gly Gly
1               5
```

<210> SEQ ID NO 211
<211> LENGTH: 9
<212> TYPE: PRT
<213> ORGANISM: Homo sapiens

<400> SEQUENCE: 211

```
Glu Ser Ala Gln Glu Pro Gly Gly Val
1               5
```

<210> SEQ ID NO 212
<211> LENGTH: 9
<212> TYPE: PRT
<213> ORGANISM: Homo sapiens

<400> SEQUENCE: 212

```
Ser Ala Gln Glu Pro Gly Gly Val Ser
1               5
```

<210> SEQ ID NO 213
<211> LENGTH: 9
<212> TYPE: PRT
<213> ORGANISM: Homo sapiens

<400> SEQUENCE: 213

```
Ala Gln Glu Pro Gly Gly Val Ser Pro
1               5
```

<210> SEQ ID NO 214
<211> LENGTH: 9
<212> TYPE: PRT
<213> ORGANISM: Homo sapiens

<400> SEQUENCE: 214

```
Gln Glu Pro Gly Gly Val Ser Pro Ala
1               5
```

<210> SEQ ID NO 215
<211> LENGTH: 9
<212> TYPE: PRT
<213> ORGANISM: Homo sapiens

<400> SEQUENCE: 215

```
Glu Pro Gly Gly Val Ser Pro Ala Glu
1               5
```

```
<210> SEQ ID NO 216
<211> LENGTH: 9
<212> TYPE: PRT
<213> ORGANISM: Homo sapiens

<400> SEQUENCE: 216

Pro Gly Gly Val Ser Pro Ala Glu Ala
1               5

<210> SEQ ID NO 217
<211> LENGTH: 9
<212> TYPE: PRT
<213> ORGANISM: Homo sapiens

<400> SEQUENCE: 217

Gly Gly Val Ser Pro Ala Glu Ala Gln
1               5

<210> SEQ ID NO 218
<211> LENGTH: 9
<212> TYPE: PRT
<213> ORGANISM: Homo sapiens

<400> SEQUENCE: 218

Gly Val Ser Pro Ala Glu Ala Gln Arg
1               5

<210> SEQ ID NO 219
<211> LENGTH: 9
<212> TYPE: PRT
<213> ORGANISM: Homo sapiens

<400> SEQUENCE: 219

Val Ser Pro Ala Glu Ala Gln Arg Ala
1               5

<210> SEQ ID NO 220
<211> LENGTH: 9
<212> TYPE: PRT
<213> ORGANISM: Homo sapiens

<400> SEQUENCE: 220

Ser Pro Ala Glu Ala Gln Arg Ala Trp
1               5

<210> SEQ ID NO 221
<211> LENGTH: 9
<212> TYPE: PRT
<213> ORGANISM: Homo sapiens

<400> SEQUENCE: 221

Pro Ala Glu Ala Gln Arg Ala Trp Trp
1               5

<210> SEQ ID NO 222
<211> LENGTH: 9
<212> TYPE: PRT
<213> ORGANISM: Homo sapiens

<400> SEQUENCE: 222

Ala Glu Ala Gln Arg Ala Trp Trp Val
1               5

<210> SEQ ID NO 223
```

```
<211> LENGTH: 9
<212> TYPE: PRT
<213> ORGANISM: Homo sapiens

<400> SEQUENCE: 223

Glu Ala Gln Arg Ala Trp Trp Val Leu
1               5

<210> SEQ ID NO 224
<211> LENGTH: 9
<212> TYPE: PRT
<213> ORGANISM: Homo sapiens

<400> SEQUENCE: 224

Ala Gln Arg Ala Trp Trp Val Leu Glu
1               5

<210> SEQ ID NO 225
<211> LENGTH: 9
<212> TYPE: PRT
<213> ORGANISM: Homo sapiens

<400> SEQUENCE: 225

Gln Arg Ala Trp Trp Val Leu Glu Pro
1               5

<210> SEQ ID NO 226
<211> LENGTH: 9
<212> TYPE: PRT
<213> ORGANISM: Homo sapiens

<400> SEQUENCE: 226

Arg Ala Trp Trp Val Leu Glu Pro Pro
1               5

<210> SEQ ID NO 227
<211> LENGTH: 9
<212> TYPE: PRT
<213> ORGANISM: Homo sapiens

<400> SEQUENCE: 227

Ala Trp Trp Val Leu Glu Pro Pro Gly
1               5

<210> SEQ ID NO 228
<211> LENGTH: 9
<212> TYPE: PRT
<213> ORGANISM: Homo sapiens

<400> SEQUENCE: 228

Trp Trp Val Leu Glu Pro Pro Gly Ala
1               5

<210> SEQ ID NO 229
<211> LENGTH: 9
<212> TYPE: PRT
<213> ORGANISM: Homo sapiens

<400> SEQUENCE: 229

Trp Val Leu Glu Pro Pro Gly Ala Arg
1               5

<210> SEQ ID NO 230
<211> LENGTH: 9
<212> TYPE: PRT
```

<213> ORGANISM: Homo sapiens

<400> SEQUENCE: 230

Val Leu Glu Pro Pro Gly Ala Arg Asp
1               5

<210> SEQ ID NO 231
<211> LENGTH: 9
<212> TYPE: PRT
<213> ORGANISM: Homo sapiens

<400> SEQUENCE: 231

Leu Glu Pro Pro Gly Ala Arg Asp Val
1               5

<210> SEQ ID NO 232
<211> LENGTH: 9
<212> TYPE: PRT
<213> ORGANISM: Homo sapiens

<400> SEQUENCE: 232

Glu Pro Pro Gly Ala Arg Asp Val Glu
1               5

<210> SEQ ID NO 233
<211> LENGTH: 9
<212> TYPE: PRT
<213> ORGANISM: Homo sapiens

<400> SEQUENCE: 233

Pro Pro Gly Ala Arg Asp Val Glu Ala
1               5

<210> SEQ ID NO 234
<211> LENGTH: 9
<212> TYPE: PRT
<213> ORGANISM: Homo sapiens

<400> SEQUENCE: 234

Pro Gly Ala Arg Asp Val Glu Ala Gln
1               5

<210> SEQ ID NO 235
<211> LENGTH: 9
<212> TYPE: PRT
<213> ORGANISM: Homo sapiens

<400> SEQUENCE: 235

Gly Ala Arg Asp Val Glu Ala Gln Leu
1               5

<210> SEQ ID NO 236
<211> LENGTH: 9
<212> TYPE: PRT
<213> ORGANISM: Homo sapiens

<400> SEQUENCE: 236

Ala Arg Asp Val Glu Ala Gln Leu Arg
1               5

<210> SEQ ID NO 237
<211> LENGTH: 9
<212> TYPE: PRT
<213> ORGANISM: Homo sapiens

<400> SEQUENCE: 237

Arg Asp Val Glu Ala Gln Leu Arg Arg
1               5

<210> SEQ ID NO 238
<211> LENGTH: 9
<212> TYPE: PRT
<213> ORGANISM: Homo sapiens

<400> SEQUENCE: 238

Asp Val Glu Ala Gln Leu Arg Arg Leu
1               5

<210> SEQ ID NO 239
<211> LENGTH: 9
<212> TYPE: PRT
<213> ORGANISM: Homo sapiens

<400> SEQUENCE: 239

Val Glu Ala Gln Leu Arg Arg Leu Gln
1               5

<210> SEQ ID NO 240
<211> LENGTH: 9
<212> TYPE: PRT
<213> ORGANISM: Homo sapiens

<400> SEQUENCE: 240

Glu Ala Gln Leu Arg Arg Leu Gln Glu
1               5

<210> SEQ ID NO 241
<211> LENGTH: 9
<212> TYPE: PRT
<213> ORGANISM: Homo sapiens

<400> SEQUENCE: 241

Ala Gln Leu Arg Arg Leu Gln Glu Glu
1               5

<210> SEQ ID NO 242
<211> LENGTH: 9
<212> TYPE: PRT
<213> ORGANISM: Homo sapiens

<400> SEQUENCE: 242

Gln Leu Arg Arg Leu Gln Glu Glu Arg
1               5

<210> SEQ ID NO 243
<211> LENGTH: 9
<212> TYPE: PRT
<213> ORGANISM: Homo sapiens

<400> SEQUENCE: 243

Leu Arg Arg Leu Gln Glu Glu Arg Thr
1               5

<210> SEQ ID NO 244
<211> LENGTH: 9
<212> TYPE: PRT
<213> ORGANISM: Homo sapiens

<400> SEQUENCE: 244

```
Arg Arg Leu Gln Glu Glu Arg Thr Cys
1               5

<210> SEQ ID NO 245
<211> LENGTH: 9
<212> TYPE: PRT
<213> ORGANISM: Homo sapiens

<400> SEQUENCE: 245

Arg Leu Gln Glu Glu Arg Thr Cys Lys
1               5

<210> SEQ ID NO 246
<211> LENGTH: 9
<212> TYPE: PRT
<213> ORGANISM: Homo sapiens

<400> SEQUENCE: 246

Leu Gln Glu Glu Arg Thr Cys Lys Val
1               5

<210> SEQ ID NO 247
<211> LENGTH: 9
<212> TYPE: PRT
<213> ORGANISM: Homo sapiens

<400> SEQUENCE: 247

Gln Glu Glu Arg Thr Cys Lys Val Cys
1               5

<210> SEQ ID NO 248
<211> LENGTH: 9
<212> TYPE: PRT
<213> ORGANISM: Homo sapiens

<400> SEQUENCE: 248

Glu Glu Arg Thr Cys Lys Val Cys Leu
1               5

<210> SEQ ID NO 249
<211> LENGTH: 9
<212> TYPE: PRT
<213> ORGANISM: Homo sapiens

<400> SEQUENCE: 249

Glu Arg Thr Cys Lys Val Cys Leu Asp
1               5

<210> SEQ ID NO 250
<211> LENGTH: 9
<212> TYPE: PRT
<213> ORGANISM: Homo sapiens

<400> SEQUENCE: 250

Arg Thr Cys Lys Val Cys Leu Asp Arg
1               5

<210> SEQ ID NO 251
<211> LENGTH: 9
<212> TYPE: PRT
<213> ORGANISM: Homo sapiens

<400> SEQUENCE: 251

Thr Cys Lys Val Cys Leu Asp Arg Ala
1               5
```

<210> SEQ ID NO 252
<211> LENGTH: 9
<212> TYPE: PRT
<213> ORGANISM: Homo sapiens

<400> SEQUENCE: 252

Cys Lys Val Cys Leu Asp Arg Ala Val
1               5

<210> SEQ ID NO 253
<211> LENGTH: 9
<212> TYPE: PRT
<213> ORGANISM: Homo sapiens

<400> SEQUENCE: 253

Lys Val Cys Leu Asp Arg Ala Val Ser
1               5

<210> SEQ ID NO 254
<211> LENGTH: 9
<212> TYPE: PRT
<213> ORGANISM: Homo sapiens

<400> SEQUENCE: 254

Val Cys Leu Asp Arg Ala Val Ser Ile
1               5

<210> SEQ ID NO 255
<211> LENGTH: 9
<212> TYPE: PRT
<213> ORGANISM: Homo sapiens

<400> SEQUENCE: 255

Cys Leu Asp Arg Ala Val Ser Ile Val
1               5

<210> SEQ ID NO 256
<211> LENGTH: 9
<212> TYPE: PRT
<213> ORGANISM: Homo sapiens

<400> SEQUENCE: 256

Leu Asp Arg Ala Val Ser Ile Val Phe
1               5

<210> SEQ ID NO 257
<211> LENGTH: 9
<212> TYPE: PRT
<213> ORGANISM: Homo sapiens

<400> SEQUENCE: 257

Asp Arg Ala Val Ser Ile Val Phe Val
1               5

<210> SEQ ID NO 258
<211> LENGTH: 9
<212> TYPE: PRT
<213> ORGANISM: Homo sapiens

<400> SEQUENCE: 258

Arg Ala Val Ser Ile Val Phe Val Pro
1               5

```
<210> SEQ ID NO 259
<211> LENGTH: 9
<212> TYPE: PRT
<213> ORGANISM: Homo sapiens

<400> SEQUENCE: 259

Ala Val Ser Ile Val Phe Val Pro Cys
1               5

<210> SEQ ID NO 260
<211> LENGTH: 9
<212> TYPE: PRT
<213> ORGANISM: Homo sapiens

<400> SEQUENCE: 260

Val Ser Ile Val Phe Val Pro Cys Gly
1               5

<210> SEQ ID NO 261
<211> LENGTH: 9
<212> TYPE: PRT
<213> ORGANISM: Homo sapiens

<400> SEQUENCE: 261

Ser Ile Val Phe Val Pro Cys Gly His
1               5

<210> SEQ ID NO 262
<211> LENGTH: 9
<212> TYPE: PRT
<213> ORGANISM: Homo sapiens

<400> SEQUENCE: 262

Ile Val Phe Val Pro Cys Gly His Leu
1               5

<210> SEQ ID NO 263
<211> LENGTH: 9
<212> TYPE: PRT
<213> ORGANISM: Homo sapiens

<400> SEQUENCE: 263

Val Phe Val Pro Cys Gly His Leu Val
1               5

<210> SEQ ID NO 264
<211> LENGTH: 9
<212> TYPE: PRT
<213> ORGANISM: Homo sapiens

<400> SEQUENCE: 264

Phe Val Pro Cys Gly His Leu Val Cys
1               5

<210> SEQ ID NO 265
<211> LENGTH: 9
<212> TYPE: PRT
<213> ORGANISM: Homo sapiens

<400> SEQUENCE: 265

Val Pro Cys Gly His Leu Val Cys Ala
1               5

<210> SEQ ID NO 266
<211> LENGTH: 9
```

```
<212> TYPE: PRT
<213> ORGANISM: Homo sapiens

<400> SEQUENCE: 266

Pro Cys Gly His Leu Val Cys Ala Glu
1               5

<210> SEQ ID NO 267
<211> LENGTH: 9
<212> TYPE: PRT
<213> ORGANISM: Homo sapiens

<400> SEQUENCE: 267

Cys Gly His Leu Val Cys Ala Glu Cys
1               5

<210> SEQ ID NO 268
<211> LENGTH: 9
<212> TYPE: PRT
<213> ORGANISM: Homo sapiens

<400> SEQUENCE: 268

Gly His Leu Val Cys Ala Glu Cys Ala
1               5

<210> SEQ ID NO 269
<211> LENGTH: 9
<212> TYPE: PRT
<213> ORGANISM: Homo sapiens

<400> SEQUENCE: 269

His Leu Val Cys Ala Glu Cys Ala Pro
1               5

<210> SEQ ID NO 270
<211> LENGTH: 9
<212> TYPE: PRT
<213> ORGANISM: Homo sapiens

<400> SEQUENCE: 270

Leu Val Cys Ala Glu Cys Ala Pro Gly
1               5

<210> SEQ ID NO 271
<211> LENGTH: 9
<212> TYPE: PRT
<213> ORGANISM: Homo sapiens

<400> SEQUENCE: 271

Val Cys Ala Glu Cys Ala Pro Gly Leu
1               5

<210> SEQ ID NO 272
<211> LENGTH: 9
<212> TYPE: PRT
<213> ORGANISM: Homo sapiens

<400> SEQUENCE: 272

Cys Ala Glu Cys Ala Pro Gly Leu Gln
1               5

<210> SEQ ID NO 273
<211> LENGTH: 9
<212> TYPE: PRT
<213> ORGANISM: Homo sapiens
```

<400> SEQUENCE: 273

Ala Glu Cys Ala Pro Gly Leu Gln Leu
1               5

<210> SEQ ID NO 274
<211> LENGTH: 9
<212> TYPE: PRT
<213> ORGANISM: Homo sapiens

<400> SEQUENCE: 274

Glu Cys Ala Pro Gly Leu Gln Leu Cys
1               5

<210> SEQ ID NO 275
<211> LENGTH: 9
<212> TYPE: PRT
<213> ORGANISM: Homo sapiens

<400> SEQUENCE: 275

Cys Ala Pro Gly Leu Gln Leu Cys Pro
1               5

<210> SEQ ID NO 276
<211> LENGTH: 9
<212> TYPE: PRT
<213> ORGANISM: Homo sapiens

<400> SEQUENCE: 276

Ala Pro Gly Leu Gln Leu Cys Pro Ile
1               5

<210> SEQ ID NO 277
<211> LENGTH: 9
<212> TYPE: PRT
<213> ORGANISM: Homo sapiens

<400> SEQUENCE: 277

Pro Gly Leu Gln Leu Cys Pro Ile Cys
1               5

<210> SEQ ID NO 278
<211> LENGTH: 9
<212> TYPE: PRT
<213> ORGANISM: Homo sapiens

<400> SEQUENCE: 278

Gly Leu Gln Leu Cys Pro Ile Cys Arg
1               5

<210> SEQ ID NO 279
<211> LENGTH: 9
<212> TYPE: PRT
<213> ORGANISM: Homo sapiens

<400> SEQUENCE: 279

Leu Gln Leu Cys Pro Ile Cys Arg Ala
1               5

<210> SEQ ID NO 280
<211> LENGTH: 9
<212> TYPE: PRT
<213> ORGANISM: Homo sapiens

<400> SEQUENCE: 280

```
Gln Leu Cys Pro Ile Cys Arg Ala Pro
1               5

<210> SEQ ID NO 281
<211> LENGTH: 9
<212> TYPE: PRT
<213> ORGANISM: Homo sapiens

<400> SEQUENCE: 281

Leu Cys Pro Ile Cys Arg Ala Pro Val
1               5

<210> SEQ ID NO 282
<211> LENGTH: 9
<212> TYPE: PRT
<213> ORGANISM: Homo sapiens

<400> SEQUENCE: 282

Cys Pro Ile Cys Arg Ala Pro Val Arg
1               5

<210> SEQ ID NO 283
<211> LENGTH: 9
<212> TYPE: PRT
<213> ORGANISM: Homo sapiens

<400> SEQUENCE: 283

Pro Ile Cys Arg Ala Pro Val Arg Ser
1               5

<210> SEQ ID NO 284
<211> LENGTH: 9
<212> TYPE: PRT
<213> ORGANISM: Homo sapiens

<400> SEQUENCE: 284

Ile Cys Arg Ala Pro Val Arg Ser Arg
1               5

<210> SEQ ID NO 285
<211> LENGTH: 9
<212> TYPE: PRT
<213> ORGANISM: Homo sapiens

<400> SEQUENCE: 285

Cys Arg Ala Pro Val Arg Ser Arg Val
1               5

<210> SEQ ID NO 286
<211> LENGTH: 9
<212> TYPE: PRT
<213> ORGANISM: Homo sapiens

<400> SEQUENCE: 286

Arg Ala Pro Val Arg Ser Arg Val Arg
1               5

<210> SEQ ID NO 287
<211> LENGTH: 9
<212> TYPE: PRT
<213> ORGANISM: Homo sapiens

<400> SEQUENCE: 287

Ala Pro Val Arg Ser Arg Val Arg Thr
```

```
1               5

<210> SEQ ID NO 288
<211> LENGTH: 9
<212> TYPE: PRT
<213> ORGANISM: Homo sapiens

<400> SEQUENCE: 288

Pro Val Arg Ser Arg Val Arg Thr Phe
1               5

<210> SEQ ID NO 289
<211> LENGTH: 9
<212> TYPE: PRT
<213> ORGANISM: Homo sapiens

<400> SEQUENCE: 289

Val Arg Ser Arg Val Arg Thr Phe Leu
1               5

<210> SEQ ID NO 290
<211> LENGTH: 9
<212> TYPE: PRT
<213> ORGANISM: Homo sapiens

<400> SEQUENCE: 290

Arg Ser Arg Val Arg Thr Phe Leu Ser
1               5

<210> SEQ ID NO 291
<211> LENGTH: 10
<212> TYPE: PRT
<213> ORGANISM: Homo sapiens

<400> SEQUENCE: 291

Met Gly Pro Lys Asp Ser Ala Lys Cys Leu
1               5                   10

<210> SEQ ID NO 292
<211> LENGTH: 11
<212> TYPE: PRT
<213> ORGANISM: Homo sapiens

<400> SEQUENCE: 292

Met Gly Pro Lys Asp Ser Ala Lys Cys Leu His
1               5                   10

<210> SEQ ID NO 293
<211> LENGTH: 12
<212> TYPE: PRT
<213> ORGANISM: Homo sapiens

<400> SEQUENCE: 293

Met Gly Pro Lys Asp Ser Ala Lys Cys Leu His Arg
1               5                   10

<210> SEQ ID NO 294
<211> LENGTH: 13
<212> TYPE: PRT
<213> ORGANISM: Homo sapiens

<400> SEQUENCE: 294

Met Gly Pro Lys Asp Ser Ala Lys Cys Leu His Arg Gly
1               5                   10
```

```
<210> SEQ ID NO 295
<211> LENGTH: 14
<212> TYPE: PRT
<213> ORGANISM: Homo sapiens

<400> SEQUENCE: 295

Met Gly Pro Lys Asp Ser Ala Lys Cys Leu His Arg Gly Pro
1               5                   10

<210> SEQ ID NO 296
<211> LENGTH: 15
<212> TYPE: PRT
<213> ORGANISM: Homo sapiens

<400> SEQUENCE: 296

Met Gly Pro Lys Asp Ser Ala Lys Cys Leu His Arg Gly Pro Gln
1               5                   10                  15

<210> SEQ ID NO 297
<211> LENGTH: 10
<212> TYPE: PRT
<213> ORGANISM: Homo sapiens

<400> SEQUENCE: 297

Arg Leu Gln Glu Glu Arg Thr Cys Lys Val
1               5                   10

<210> SEQ ID NO 298
<211> LENGTH: 10
<212> TYPE: PRT
<213> ORGANISM: Homo sapiens

<400> SEQUENCE: 298

Gln Leu Cys Pro Ile Cys Arg Ala Pro Val
1               5                   10

<210> SEQ ID NO 299
<211> LENGTH: 10
<212> TYPE: PRT
<213> ORGANISM: Homo sapiens

<400> SEQUENCE: 299

Arg Leu Ala Ser Phe Tyr Asp Trp Pro Leu
1               5                   10

<210> SEQ ID NO 300
<211> LENGTH: 10
<212> TYPE: PRT
<213> ORGANISM: Homo sapiens

<400> SEQUENCE: 300

Leu Leu Arg Ser Lys Gly Arg Asp Phe Val
1               5                   10

<210> SEQ ID NO 301
<211> LENGTH: 10
<212> TYPE: PRT
<213> ORGANISM: Homo sapiens

<400> SEQUENCE: 301

Val Leu Glu Pro Pro Gly Ala Arg Asp Val
1               5                   10

<210> SEQ ID NO 302
```

<211> LENGTH: 10
<212> TYPE: PRT
<213> ORGANISM: Homo sapiens

<400> SEQUENCE: 302

Pro Leu Thr Ala Glu Val Pro Pro Glu Leu
1               5                   10

<210> SEQ ID NO 303
<211> LENGTH: 10
<212> TYPE: PRT
<213> ORGANISM: Homo sapiens

<400> SEQUENCE: 303

Ser Glu Glu Leu Arg Leu Ala Ser Phe Tyr
1               5                   10

<210> SEQ ID NO 304
<211> LENGTH: 10
<212> TYPE: PRT
<213> ORGANISM: Homo sapiens

<400> SEQUENCE: 304

Val Gln Glu Thr His Ser Gln Leu Leu Gly
1               5                   10

<210> SEQ ID NO 305
<211> LENGTH: 10
<212> TYPE: PRT
<213> ORGANISM: Homo sapiens

<400> SEQUENCE: 305

Thr Ala Glu Val Pro Pro Glu Leu Leu Ala
1               5                   10

<210> SEQ ID NO 306
<211> LENGTH: 10
<212> TYPE: PRT
<213> ORGANISM: Homo sapiens

<400> SEQUENCE: 306

Gln Asp Lys Val Arg Cys Phe Phe Cys Tyr
1               5                   10

<210> SEQ ID NO 307
<211> LENGTH: 10
<212> TYPE: PRT
<213> ORGANISM: Homo sapiens

<400> SEQUENCE: 307

Lys Val Cys Leu Asp Arg Ala Val Ser Ile
1               5                   10

<210> SEQ ID NO 308
<211> LENGTH: 10
<212> TYPE: PRT
<213> ORGANISM: Homo sapiens

<400> SEQUENCE: 308

Arg Arg Leu Gln Glu Glu Arg Thr Cys Lys
1               5                   10

<210> SEQ ID NO 309
<211> LENGTH: 10
<212> TYPE: PRT

<213> ORGANISM: Homo sapiens

<400> SEQUENCE: 309

Phe Leu Leu Arg Ser Lys Gly Arg Asp Phe
1               5                   10

<210> SEQ ID NO 310
<211> LENGTH: 10
<212> TYPE: PRT
<213> ORGANISM: Homo sapiens

<400> SEQUENCE: 310

Glu Leu Leu Ala Ala Ala Gly Phe Phe His
1               5                   10

<210> SEQ ID NO 311
<211> LENGTH: 10
<212> TYPE: PRT
<213> ORGANISM: Homo sapiens

<400> SEQUENCE: 311

Cys Leu Asp Arg Ala Val Ser Ile Val Phe
1               5                   10

<210> SEQ ID NO 312
<211> LENGTH: 10
<212> TYPE: PRT
<213> ORGANISM: Homo sapiens

<400> SEQUENCE: 312

Ile Leu Gly Gln Leu Arg Pro Leu Thr Glu
1               5                   10

<210> SEQ ID NO 313
<211> LENGTH: 10
<212> TYPE: PRT
<213> ORGANISM: Homo sapiens

<400> SEQUENCE: 313

Phe Cys Tyr Gly Gly Leu Gln Ser Trp Lys
1               5                   10

<210> SEQ ID NO 314
<211> LENGTH: 10
<212> TYPE: PRT
<213> ORGANISM: Homo sapiens

<400> SEQUENCE: 314

Ala Phe Pro Gly Met Gly Ser Glu Glu Leu
1               5                   10

<210> SEQ ID NO 315
<211> LENGTH: 10
<212> TYPE: PRT
<213> ORGANISM: Homo sapiens

<400> SEQUENCE: 315

Gly Pro Arg Ser Leu Gly Ser Pro Val Leu
1               5                   10

<210> SEQ ID NO 316
<211> LENGTH: 10
<212> TYPE: PRT
<213> ORGANISM: Homo sapiens

```
-continued

<400> SEQUENCE: 316

Val Arg Cys Phe Phe Cys Tyr Gly Gly Leu
1               5                   10

<210> SEQ ID NO 317
<211> LENGTH: 10
<212> TYPE: PRT
<213> ORGANISM: Homo sapiens

<400> SEQUENCE: 317

Arg Arg Leu Gln Glu Glu Arg Thr Cys Lys
1               5                   10

<210> SEQ ID NO 318
<211> LENGTH: 10
<212> TYPE: PRT
<213> ORGANISM: Homo sapiens

<400> SEQUENCE: 318

Glu Arg Thr Cys Lys Val Cys Leu Asp Arg
1               5                   10
```